US008268809B2

(12) United States Patent
Kalman et al.

(10) Patent No.: US 8,268,809 B2
(45) Date of Patent: Sep. 18, 2012

(54) KINASE INHIBITORS FOR PREVENTING OR TREATING PATHOGEN INFECTION AND METHOD OF USE THEREOF

(75) Inventors: Daniel Kalman, Atlanta, GA (US); William Bornmann, Missouri City, TX (US)

(73) Assignees: Emory University, Atlanta, GA (US); M.D. Anderson Cancer Center, Houston, TX (US)

( * ) Notice: Subject to any disclaimer, the term of this patent is extended or adjusted under 35 U.S.C. 154(b) by 399 days.

(21) Appl. No.: 12/439,961

(22) PCT Filed: Sep. 5, 2007

(86) PCT No.: PCT/US2007/077578
§ 371 (c)(1),
(2), (4) Date: Oct. 1, 2009

(87) PCT Pub. No.: WO2008/079460
PCT Pub. Date: Jul. 3, 2008

(65) Prior Publication Data
US 2010/0249122 A1      Sep. 30, 2010

Related U.S. Application Data

(60) Provisional application No. 60/824,540, filed on Sep. 5, 2006.

(51) Int. Cl.
*A01N 43/00* (2006.01)
*A01N 43/54* (2006.01)
*A61K 31/33* (2006.01)
*A61K 31/50* (2006.01)
*A61K 31/505* (2006.01)
*C07D 239/42* (2006.01)
*C07D 401/04* (2006.01)
*C07D 239/00* (2006.01)
*C07D 239/02* (2006.01)
*C07D 401/00* (2006.01)
*C07D 403/00* (2006.01)
*C07D 405/00* (2006.01)
*C07D 409/00* (2006.01)
*C07D 411/00* (2006.01)
*C07D 413/00* (2006.01)
*C07D 417/00* (2006.01)
*C07D 419/00* (2006.01)

(52) U.S. Cl. .................... 514/183; 514/252.01; 514/256; 514/272; 544/242; 544/331

(58) Field of Classification Search .................... None
See application file for complete search history.

(56) References Cited

U.S. PATENT DOCUMENTS 5,369,108 A    11/1994  Breslow
2003/0032596 A1  2/2003  Schneider et al.
2005/0063903 A1  3/2005  Zeligs

FOREIGN PATENT DOCUMENTS

WO     2002/22597     3/2002
WO  WO 2005/070900   8/2005
WO  WO 2005/072826   8/2005
WO     2006/021458   3/2006
WO     2008/024829   2/2008

OTHER PUBLICATIONS

Daibata et al. "Effect of Genistein, a Tyrosine Kinase Inhibitor, on Latent EBV activation induced by cross-linkage of membrane IgG in Akata B cells" The Journal of Immunology, vol. 147, 292-297, No. 1, Jul. 1, 1991.*
Reeves et al., "Disabling poxvirus pathogenesis by inhibition of Ab-family tyrosine kinases", Nature Medicine, vol. 11, No. 7 (Jul. 2005), pp. 731-739.*
Yura et al., "Inhibition of herpes simplex virus replication by Genistein, an inhibitor of protein-tyrosine kinase." Arch Virol. 1993;132(3-4):451-6 (abstract only).*
Bot and Bona, Genetic immunization of neonates, *Microbes Infect.*, 4:511-520 (2002).
Carter et al., Vaccinia virus cores are transported on microtubules, *J. Gen. Virol.*, 84:2443-2458 (2003).
Cudmore et al., Vaccinia virus: a model system for actin-membrane interactions, *J. Cell. Sci.*, 109:1739-1747 (1996).
Cudmore et al., Viral manipulations of the actin cytoskeleton, *Trends Microbiol.*, 5(4):142-148 (1997).
Frischknecht et al., Actin-based motility of vaccinia virus mimics receptor tyrosine kinase signaling, *Nature*, 401(6756): 926-929 (1999).
Frischknecht and Way, Surfing pathogens and the lessons learned for actin polymerization, *Trends Cell Biol.*, 11(1):30-38 (2001).
Goosney et al., Enteropathogenic *Escherichia coli* Inhibits Phagocytosis, *Infect. Immun.*, 67(2):490-495 (1999). Goosney et al., Gut Feelings: Enteropathogenic *E. coli* (EPEC) Interactions with the Host, *Annu. Rev. Cell Dev. Biol.*, 16:173-179 (2000).
Gruenheid et al., Enteropathogenic *E. coli* Tir binds Nck to initiate actin pedestal formation in host cells, *Nat. Cell. Biol.*, 3: 856-859 (2001).
Hollinshead et al., Vaccinia virus utilizes microtubules for movement to the cell surface, *J. Cell. Biol.*, 154:389-402 (2001).
Jerse et al., A genetic locus of enteropathogenic *Escherichia coli* necessary for the production of attaching and effacing lesions on tissue culture cells, *Proc. Natl. Acad. Sci. USA*, 87:7839 (1990).
Kalman et al., Enteropathogenic *E. coli* acts through WASP and Arp2/3 complex to form actin pedestals, *Nat. Cell. Biol.*, 1:389-391 (1999).
Kenny et al., Enteropathogenic *E. coli* (EPEC) Transfers Its Receptor for Intimate Adherence into Mammalian Cells, *Cell*, 91:511-520 (1997).
Kenny, Phosphorylation of tyrosine 474 of the enteropathogenic *Escherichia coli* (EPEC) Tir receptor molecule is essential for actin nucleating activity and is preceded by additional host modifications, *Mol. Microbiol.*, 31(4):1229-1241 (1999).
Kerkela et al., Cardiotoxicity of the cancer therapeutic agent imatinib mesylate, *Nat. Med.*, 12(8): 908-916 (2006).

(Continued)

*Primary Examiner* — Jeffrey S. Lundgren
*Assistant Examiner* — William Lee
(74) *Attorney, Agent, or Firm* — McKeon, Meunier, Carlin & Curfman, LLC

(57) ABSTRACT

The present invention provides compositions and methods of use thereof to prevent and/or treat pathogenic infection. In particular, the present invention provides the use of kinase inhibitors to inhibit kinases that involve in pathogen-host cell interactions that are associated with or cause pathogenic infections, therefore, to effectively prevent and/or treat pathogenic infections with far less likely to engender resistance as compared to conventional antibiotics and anti-viral drugs. The present invention further provides the use of kinase inhibitors for the treatment of acute pathogenic infections for a short period of time to avoid toxicities that may caused by long term use of these kinase inhibitors.

10 Claims, 4 Drawing Sheets

OTHER PUBLICATIONS

Knutton et al., Diagnosis of Enteropathogenic *Escherichia coli*, *Lancet*, 2:218 (1989).

Lommel et al., Actin pedestal formation by enteropathogenic *Escherichia coli* and intracellular motility of *Shigella flexneri* are abolished in N-WASP-defective cells, *EMBO Rep.*, 2(9): 850-857 (2001).

McDaniel et al., A cloned pathogenicity island from enteropathogenic *Escherichia coli* confers the attaching and effacing phenotype on *E. coli* K-12, *Mol. Microbiol.*, 23(2):399-407 (1997).

Moreau et al., A complex of N-WASP and WIP integrates signaling cascades that lead to actin polymerization, *Nat. Cell. Biol.*, 2:441-448 (2000).

Newsome et al., Scr Mediates a Switch from Microtubule- to Actin-Based Motility of Vaccinia Virus, *Science*, 306:124-128 (2004).

Parkinson and Smith, Vaccinia Virus Gene Encodes a $M_r$ 43-50 K Protein on the Surface of Extracellular Enveloped Virus, *Virology*, 204:376-390 (1994).

Perna et al., Genome sequence of enterohaemorrhagic *Escherichia coli* O157:H7, *Nature*, 409(6819):529-533 (2001).

Ploubidou et al., Vaccinia virus infection disrupts microtubule organization and centrosome function, *EMBO J.*, 19(15): p. 3932-3944 (2000).

Reeves et al., Disabling poxvirus pathogenesis by inhibition of Abl-family tyrosine kinases, *Nat. Med.*, 11:731-738 (2005).

Rietdorf et al., Kinesin-dependent movement on microtubules precedes actin-based motility of vaccinia virus, *Nat. Cell. Biol.*, 3(11):992-1000 (2001).

Rempel and Traktman, Vaccinia Virus B1 Kinase: Phenotypic Analysis of Temperature-Sensitive Mutants and Enzymatic Characterization of Recombinant Proteins, *J. Virol.*, 66(7):4413-4426 (1992).

Rohatgi et al., The Interaction between N-WASP and the Arp2/3 Complex Links Cdc42-Dependent Signals to Actin Assembly, *Cell*, 97:221-231 (1999).

Scaplehorn et al., Grb2 and Nck Act Cooperatively to Promote Actin-Based Motility of Vaccinia Virus, *Curr. Biol.*, pp. 740-745 (2002).

Smith et al., The formation and function of extracellular enveloped vaccinia virus, *J. Gen. Virol.*, 83:2915-2931 (2002).

Smith et al., Vaccinia Virus Motility, *Ann. Rev. Microbiol.*, 57:323-342 (2003).

Swimm et al., Enteropathogenic *Escherichia coli* Use Redundant Tyrosine Kinases to Form Actin Pedestals, *Molecular Biology of the Cell*, 15:3520-3529 (2004).

Traktman et al., Vaccinia Virus Encodes an Essential Gene with Strong Homology to Protein Kinases, *J. Biol. Chem.*, 264(36): 21458-21461 (1989).

Traktman et al., Temperature-Sensitive Mutants with Lesions in the Vaccinia Virus F10 Kinase Undergo Arrest at the Earliest Stage of Virion Morphogenesis, *J. Virol.*, 69(10): 6581-6587 (1995).

Ward and Moss, Visualization of Intracellular Movement of Vaccinia Virus Virions Containing a Green Fluorescent Protein-B5R Membrane Protein Chimera, *J. Virol.*, 75(10):4802-13 (2001).

Ward and Moss, Vaccinia Virus Intracellular Movement is Associated with Microtubules and Independent of Actin Tails, *J. Virol.*, 75(23):11651-11663 (2001).

Welsh, Assessing CD8 T Cell Number and Dysfunction in the Presence of Antigen, *J. Exp. Med.*, 193(5):F19-F22 (2001).

Wolffe et al., Role for the Vaccinia Virus A36R Outer Envelope Protein in the Formation of Virus-Tipped Actin-Containing Microvilli and Cell-to-Cell Virus Spread, *Virology*, 244: 20-26 (1998).

International Search Report mailed Aug. 5, 2008 in counterpart International Application No. PCT/US2007/077578.

Peng et al., "Identification of Novel Inhibitors of BCR-ABL Tyrosine Kinase via Virtual Screening." *Bioorganic and Medicinal Chemistry Letters*, 13(21):3693-3699 (2003).

Tanis et al., "Two distinct phosphorylation pathways have additive effects on Abl family kinase activation," *Molecular and Cellular Biology*, 23(11): 3884-3896 (2003).

Weisberg et al., "AMN107 (nilotinib): a novel and selective inhibitor of BCR-ABL," British Journal of Cancer, 94(12): 1765-1769 (2006).

Partial European Search Report mailed Jul. 28, 2011 in counterpart application European Application No. EP11000914.9, 8 pages.

Demonte, et al., "Administration of HDAC inhibitors to reactivate HIV-1 expression in latent cellular reservoirs: implications for the development of therapeutic strategies", Biochemical Pharmacology 68(6):1231-1238 (2004).

Nimmanapalli, et al., "Cotreatment with the histone deacetylase inhibitor suberoylanilide hyroxamic acid (SAHA) enhances imatinib-induced apoptosis of Bcr-Abl-positive human acute leukemia cells", Blood, American Society of Hematology, U.S. 101(8):3236-3239 (2003).

Sankaranarayanapillai, et al., "Detection of histone deacetylas inhibition by noninvasive magnetic resonance spectroscopy" Molecular Cancer Therapeutics, 5(5):1325-1334 (2006) [abstract].

Partial European Search Report for EP 12162339.1, mailed May 24, 2012.

* cited by examiner

Plaque Differences due to Drug Treatment:

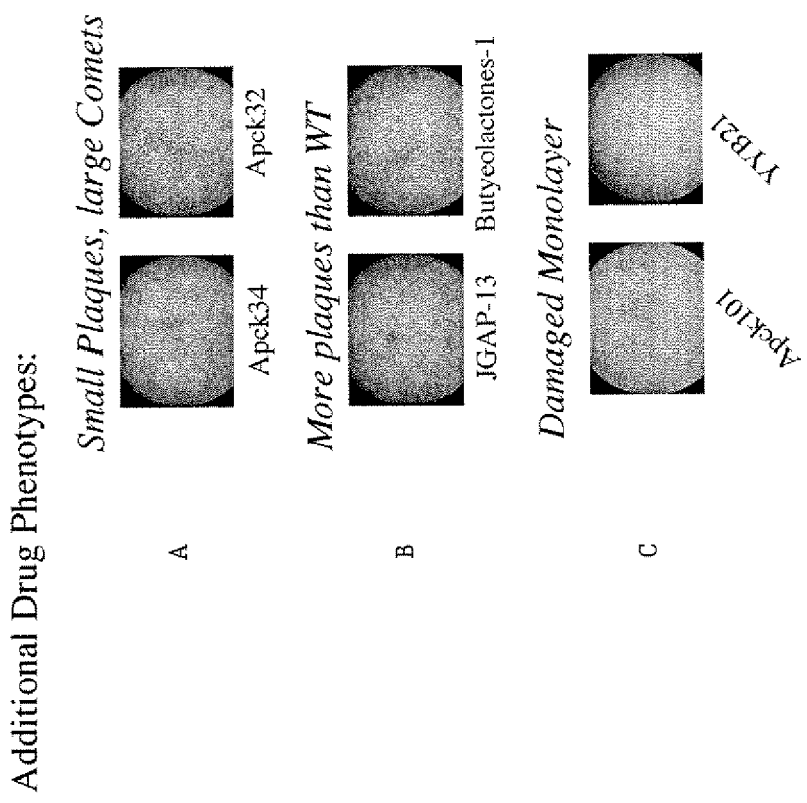

KINASE INHIBITORS FOR PREVENTING OR TREATING PATHOGEN INFECTION AND METHOD OF USE THEREOF

CROSS-REFERENCE TO RELATED APPLICATION

This application claims benefit of U.S. Provisional Application No. 60/824,540, filed Sep. 5, 2006. The application is incorporated herein by reference.

ACKNOWLEDGMENT OF FEDERAL RESEARCH SUPPORT

This invention was made, at least in part, with funding from National Institutes of Health (NIH Grant Number 1R01A105667-01). Accordingly, the United States Government has certain rights in this invention.

FIELD OF THE INVENTION

The invention relates to compositions and methods of use thereof to prevent and/or treat pathogenic infection. In particular, the present invention relates to a development and identification of compounds that alter the way in which diverse bacterial and viral pathogens interact with the host, so as to block or limit disease caused by these pathogens and permit the host immune system to clear the pathogens.

BACKGROUND OF THE INVENTION

The last several decades have witnessed an onslaught of deadly bacterial and viral pathogens around the globe. A broad array of human pathogens exists, including various microbes such as bacteria, protozoa, viruses, algae, and fungi. The innate capacity to respond to selective pressures has driven the evolution of microbes and enabled them to adapt to complex and variable environments. It is perhaps no surprise, then, that infectious microbes have readily evolved mechanisms to evade our attempts to destroy them with synthetic or natural anti-microbial compounds.

The fact that microbes develop resistance at a rate that far exceeds development of new therapeutics arguably poses the single most serious public health threat in this century in both developing and developed nations. There is no denying that anti-microbial strategies have met with spectacular success over the last century.

For example, antibacterial and antiviral drugs directed at targets within the pathogen have been used to save countless lives. But it is becoming increasingly evident that such success is not sustainable. To counter these drugs, bacterial and viral pathogens have evolved sophisticated mechanisms to inactivate these compounds. Examples include the pan-drug resistant strains of *Staphylococcus aureus, Klebsiella pneumoniae, Pseudomonas aeruginosa*, and *Mycobacterium tuberculosis* (TB) among bacteria and human immunodeficiency virus (HIV) among viruses.

More worrisome still is the lack of effort on the part of pharmaceutical companies (big or small) to pursue development of new antimicrobials. Efforts to develop new antibiotics by the pharmaceutical industry by large-scale screens of chemical libraries that inhibit growth have largely failed, and new tetracycline and sulfanilamide analogs will likely engender resistance and will quickly be rendered useless. The resistance problem is compounded further by indiscriminate and inappropriate use of antibiotics and antiviral compounds without compliance measures or public health policies to reduce disease burden. With the astounding costs of clinical trials, the failure to control generic sales, and the capacity to generate substantial revenues from medications for chronic illnesses there is little if any financial incentive for big pharmaceutical companies to even develop new antibiotics, and small biotechnology companies simply do not have the resources.

Even with the current level of effort there is cause for concern. Of the new drugs under development, most, if not all, will likely engender resistance quickly upon release (e.g., folate biosynthesis inhibitor Iclaprim). The search for novel antiviral compounds has been somewhat more successful and largely motivated by the HIV pandemic, but drugs have been developed principally against viral targets, and mutation rates among viruses still outpaces new development. One positive development has been vaccines, which are promising for some bacterial and viral illnesses. But vaccines are not successful in all cases (e.g., in young children), and adequate resources have not been made available.

There is therefore an urgent need to develop compounds and methods effective for the prevention and treatment of pathogenic infection.

SUMMARY OF THE INVENTION

The present invention provides compounds that alter the way in which diverse bacterial and viral pathogens interact with the host. The compounds provided by the present invention interact with host proteins required by microbes for pathogenesis. As such, the compounds provided by the present invention are far less likely to engender resistance compared to conventional antibiotics or anti-viral drugs because the pathogen cannot easily evolve novel pathogenesis strategies. Therefore, the compounds provided by the present invention have the capacity to limit disease and permit the host immune system to clear the pathogen. In one preferred embodiment, the present invention provides compounds that inhibit kinases involved in pathogen-host cell interactions that are associated with or cause pathogenic infection. The kinase inhibitors of the present invention include, but are not limited, to the compounds listed in Table A below. In yet another preferred embodiment, the kinase inhibitors of the present invention are used for the treatment of acute pathogenic infections for a short period of time, preferably, less than 3 weeks, to avoid toxicity issues.

In yet another preferred embodiment, the present invention provides compositions comprising compounds including those listed in Table A below in preventing or treating infections caused by diverse bacterial and viral pathogens. The bacterial and viral pathogens include, but are not limited to pathogenic *Escherichia coli* (enteropathogenic *Escherichia coli* (EPEC), enterohemorrhagic *Escherichia coli* (EHEC), uropathogenic *Escherichia coli* (UPEC), and enteroinvasive *Escherichia coli* (EIEC)), *Mycobacterium tuberculosis* (mTB), *Pseudomonas aeruginosa, Chlamydia trachomatis*, Pox viruses (including Vaccinia and variola viruses), polyoma viruses (including JC and BK viruses), human immunodeficiency viruses (for example, HIV-1), Herpes viruses (including Herpes Simplex virus, Epstein Barr virus, and Gamma Herpes virus), influenza virus, *Shigella flexneri*, Coxsackie virus, *Helicobacter pylori*, West Nile virus, *Listeria monocytogenes, Salmonella typhimurium*, cytomegalovirus (CMV), and other pathogens that are described in the literature.

In yet another preferred embodiment, the present invention provides compositions comprising compounds including those listed in Table A below that inhibit kinases involved in pathogen-host cell interactions that are associated with or cause pathogenic infection. In one of the preferred embodiments, the kinase is tyrosine kinase. In yet another preferred embodiment, the present invention provides compositions comprising inhibitors to tyrosine kinase, preferably, Ableson (Abl) and/or Src-family tyrosine kinase, or pharmaceutically acceptable salts, enantiomers, analogs, esters, amides, prodrugs, metabolites, or derivatives thereof.

In yet another preferred embodiment, the present invention provides methods of preventing or treating pathogenic infections. Such methods comprise administering the compositions comprising kinase inhibitors of the present invention in therapeutically effective amounts to a patient in need thereof for treating infection by a broad array of pathogens, including microbial pathogens such as bacteria, protozoa, viruses, algae, and fungi. In particular, the present invention provides the use of these compositions to treat disease associated with the pathogens including *Escherichia coli* (enteropathogenic *Escherichia coli* (EPEC), enterohemorrhagic *Escherichia coli* (EHEC), uropathogenic *Escherichia coli* (UPEC), and enteroinvasive *Escherichia coli* (EIEC)), *Mycobacterium tuberculosis* (mTB), *Pseudomonas aeruginosa*, *Chlamydia trachomatis*, Pox viruses (including Vaccinia and variola viruses), polyoma viruses (including JC and BK viruses), human immunodeficiency viruses (for example, HIV-1), Herpes viruses (including Herpes Simplex virus, Epstein Barr virus, and Gamma Herpes virus), influenza virus, *Shigella flexneri*, Coxsackie virus, *Helicobacter pylori*, West Nile virus, *Listeria monocytogenes*, *Salmonella typhimurium*, cytomegalovirus (CMV), and other pathogens that are described in the literature. In one of the preferred embodiments, the present invention provides the use of these compositions to treat acute pathogenic infections for a short period of time, preferably, less than three weeks, to avoid toxicity. The compositions may be administered by any means of administration as long as a therapeutically effective amount for the treatment of pathogenic infection is delivered.

BRIEF DESCRIPTION OF THE DRAWINGS

FIG. 1A shows plaque formation with vaccinia virus in the absence of any kinase inhibitors in 3T3 cells, strain WR (left: Positive Control), and in the absence of virus and any kinase inhibitors (Right: Negative Control); FIG. 1B shows formations of small plaques with comets with compounds Eph_2wbz_105, Eph_2wbz_203, Eph_2wbz_206 and LG2-71, respectively; and FIG. 1C shows formations of small plaques with no comets with compounds DM-I-187 and DM-I-196, respectively.

FIG. 2A shows pinpoint plaque formations by compounds Eph_2wbz_100, Apck108, Apck111, Apck26 and Apck27, respectively; FIG. 2B shows no pinpoint plaque formed with compounds Apck105, LG2-91 and LG2-96, respectively; and FIG. 2C shows positive (left) and negative (right) controls.

FIGS. 4A-C illustrate additional drug phenotypes in Plaque Assays. FIG. 4A shows small plaque and large comets for compounds Apck34 (left) and Apck32 (right); FIG. 4B shows more plaque formations than wild type (WT, with only the virus infection) for compounds JGAP-13 (left) and Butyeolactones-1 (right); and FIG. 4C shows damaged monolayer for compounds Apck101 (left) and YYB21 (right).

DETAILED DESCRIPTION OF THE INVENTION

Figure 1:
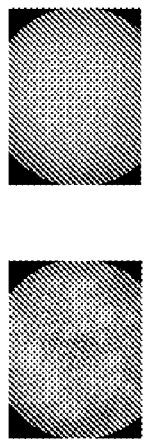
FIGS. 1A-C illustrate small plaque formations due to drug treatment in Plaque Assays.
Figure 1:
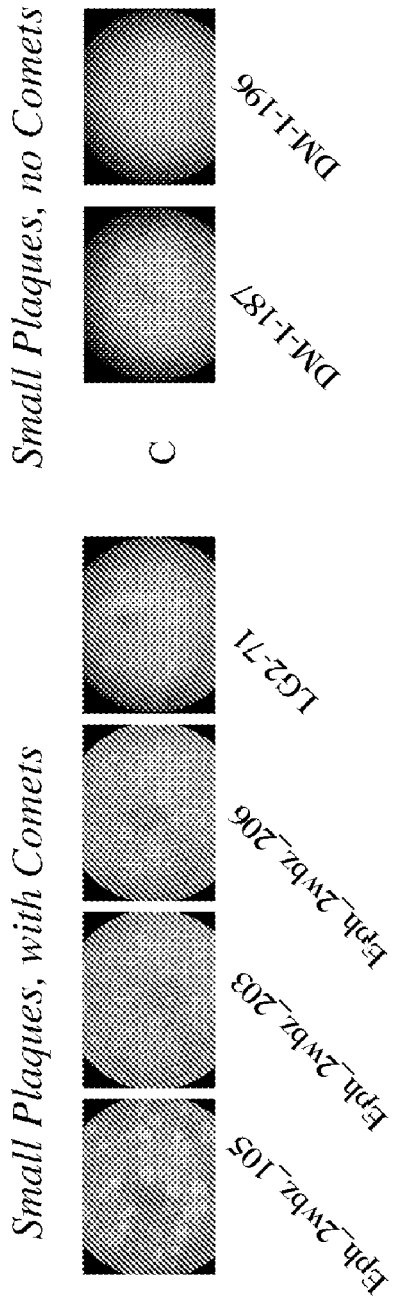
Figure 1:
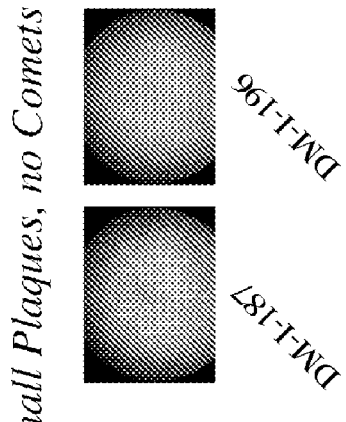
Figure 1:
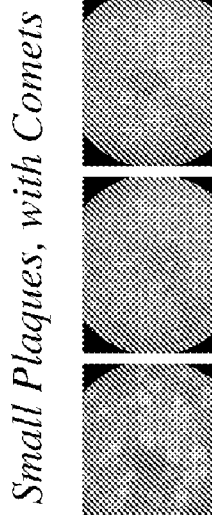

The present invention provides compositions comprising compounds that inhibit kinases involved in pathogen-host cell interactions that are associated with or cause pathogenic infection and methods of using such compositions. The compounds of the present invention include, but are not limited to those listed in the following Table A. As used herein, the terms "compounds" and "kinase inhibitors" are used interchangeably, referring to chemicals that are capable of interacting with kinases involved in pathogen-host cell interactions that are associated with or cause pathogen infections, including but not limited to those chemicals with the structures shown in the following Table A.

TABLE A

| Name of the Compound | Structure and M.F. and Molecular Weight |
|---|---|
| Eph2_wbz 101 | (489.55) |

TABLE A-continued
| Name of the Compound | Structure and M.F. and Molecular Weight |
|---|---|
| Eph2_wbz 102 | 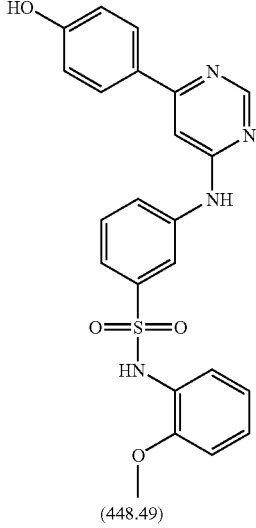<br>(448.49) |
| Eph2_wbz 103 | 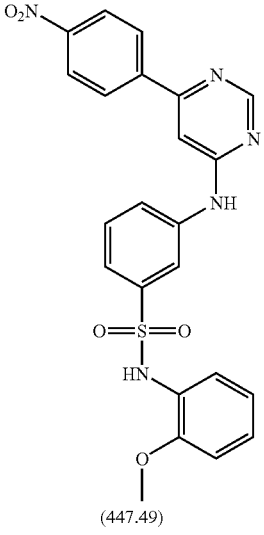<br>(447.49) |

TABLE A-continued
| Name of the Compound | Structure and M.F. and Molecular Weight |
|---|---|
| Eph2__wbz 104 | 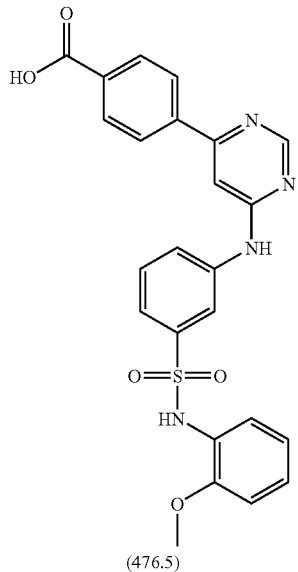<br>(476.5) |
| Eph2__wbz 105 | 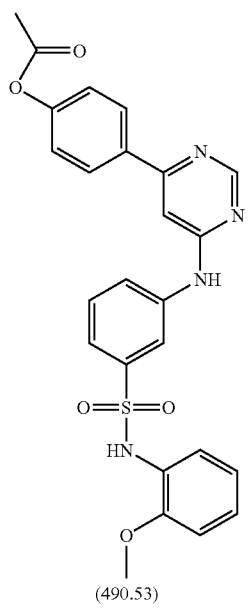<br>(490.53) |

TABLE A-continued
| Name of the Compound | Structure and M.F. and Molecular Weight |
|---|---|
| Eph2_wbz 106 | 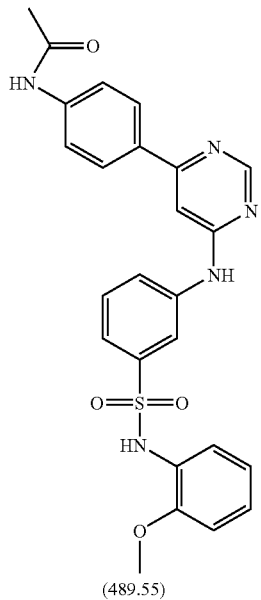<br>(489.55) |
| Eph2_wbz 107 | 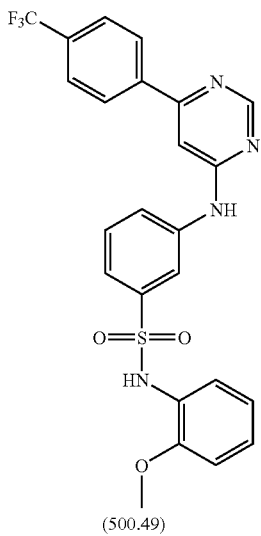<br>(500.49) |

TABLE A-continued
| Name of the Compound | Structure and M.F. and Molecular Weight |
|---|---|
| Eph2_wbz 108 | 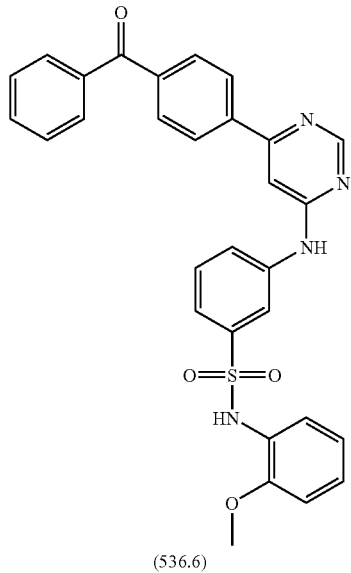<br>(536.6) |
| Eph2_wbz 109 | 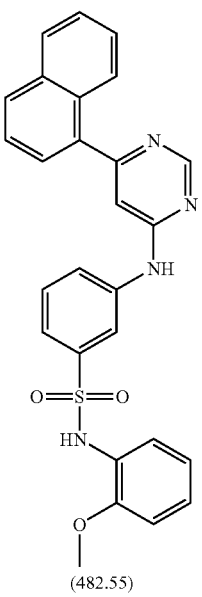<br>(482.55) |

TABLE A-continued
| Name of the Compound | Structure and M.F. and Molecular Weight |
|---|---|
| Eph2_wbz 110 | 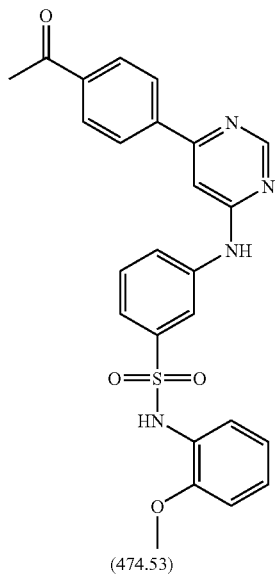 (474.53) |
| Eph2_wbz 111 | 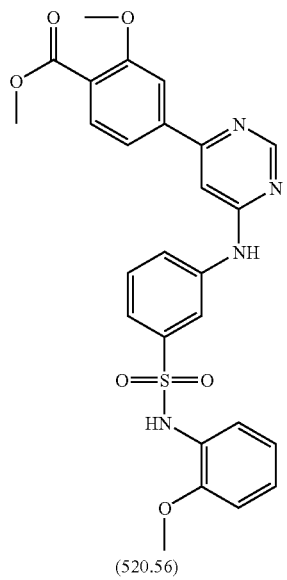 (520.56) |

TABLE A-continued
| Name of the Compound | Structure and M.F. and Molecular Weight |
|---|---|
| Eph2_wbz 112 | 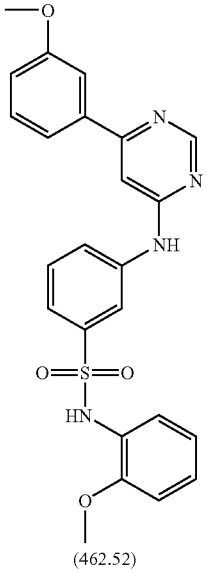 (462.52) |
| Eph2-wbz 115 | 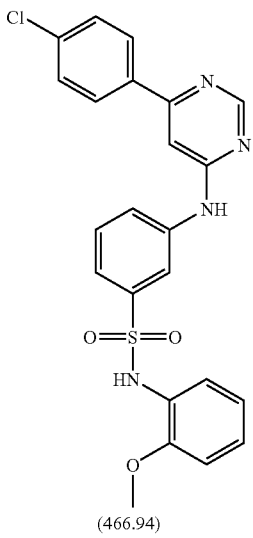 (466.94) |

TABLE A-continued
| Name of the Compound | Structure and M.F. and Molecular Weight |
|---|---|
| Eph2-wbz 116 | 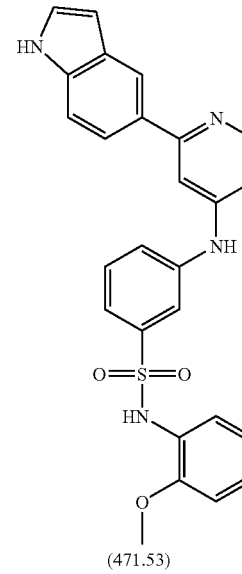 (471.53) |
| Eph2-wbz 117 | 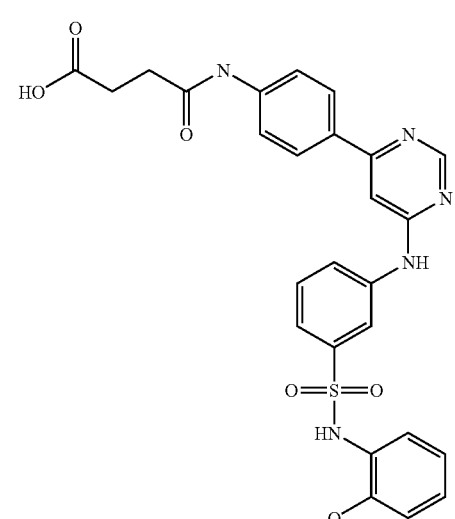 (546.57) |
| Wbzj-I | 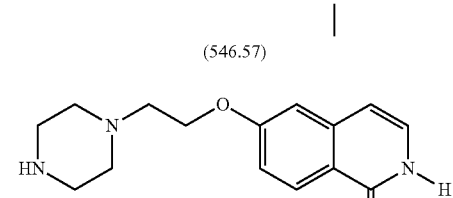 CH$_3$SO$_3$H<br>C$_{16}$H$_{23}$N$_3$O$_5$S<br>Exact Mass: 369.14<br>Mol. Wt.: 369.44<br>Z.H. Peng wbzjk2_1<br>(369) |

TABLE A-continued

| Name of the Compound | Structure and M.F. and Molecular Weight |
|---|---|
| Jak2F-2 | (493) |
| WBZ-6 | C₃₄H₃₄N₈O<br>Exact Mass: 570.29<br>Zhenghong Peng WBZ_6 |
| ANIN10T | Mol. Wt.: 529.52<br>AMN107<br>Zhenghong Peng |
| STI-OH | STI-OH<br>C₃₀H₃₃N₇O₂<br>Mol. Wt.: 523.63 |

TABLE A-continued

| Name of the Compound | Structure and M.F. and Molecular Weight |
|---|---|
| STI-F | STI_F_1<br>C$_{35}$H$_{34}$FN$_7$O<br>Exact Mass: 587.28 |
| STI_I_3 | STI_I_3<br>C$_{35}$H$_{34}$IN$_7$O<br>Exact Mass: 695.19 |
| StiAF3-iAr | C$_{34}$H$_{34}$N$_8$O<br>Exact Mass: 570.29<br>Zhenghong Peng WBZ_6 |
| StiAF3_Ue | C$_{30}$H$_{33}$N$_7$O<br>Exact Mass: 507.27<br>WBZ1 Zhenghong Peng |

TABLE A-continued
| Name of the Compound | Structure and M.F. and Molecular Weight |
|---|---|
| CGP-2-sti571 | 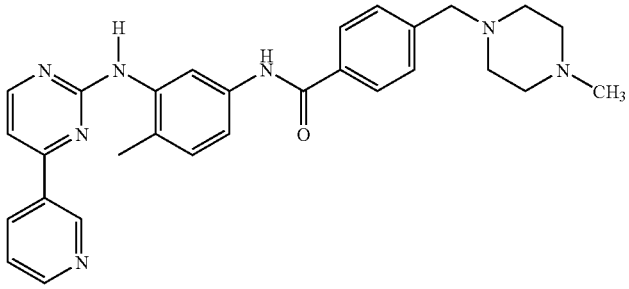<br>$C_{29}H_{31}N_7O$<br>Mol. Wt.: 493.6 |
| CGP51148 | 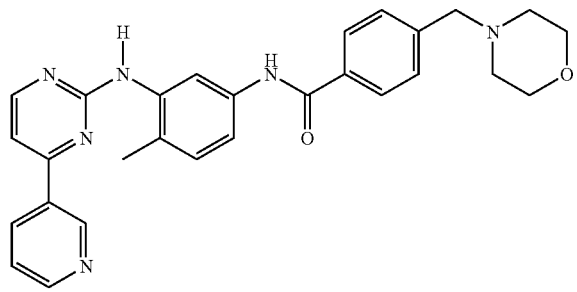<br>$C_{28}H_{28}N_6O_2$<br>Mol. Wt.: 480.56 |
| STLF2 | 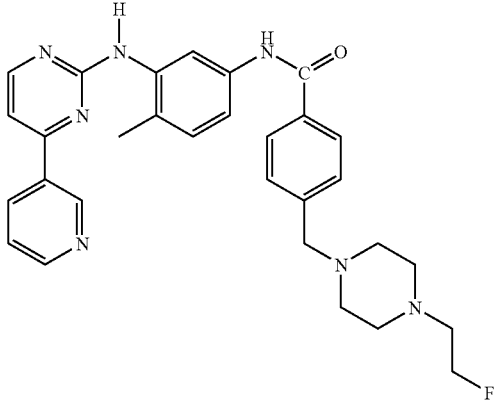<br>STI_F2<br>$C_{30}H_{32}FN_7O$<br>Mol. Wt.: 525.62<br>Zhenghong Peng |
| WBZ-4 | 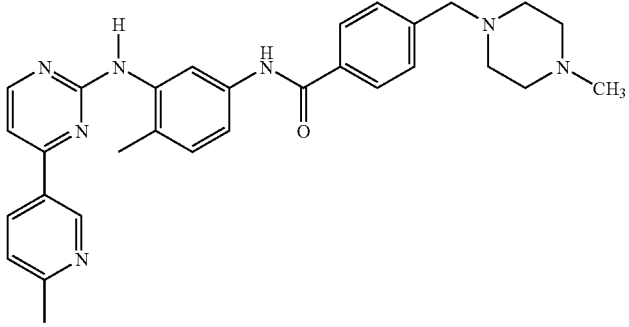<br>$C_{30}H_{33}N_7O$<br>Exact Mass.: 507.27<br>Zhenghong Peng WBZ_4 |

TABLE A-continued
| Name of the Compound | Structure and M.F. and Molecular Weight |
|---|---|
| CP2011 | 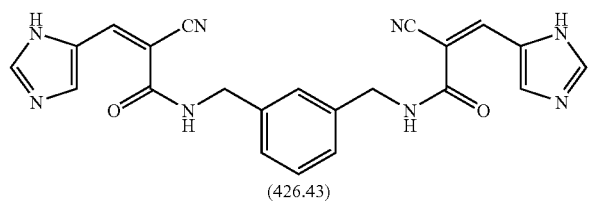<br>(426.43) |
| CP2012 | 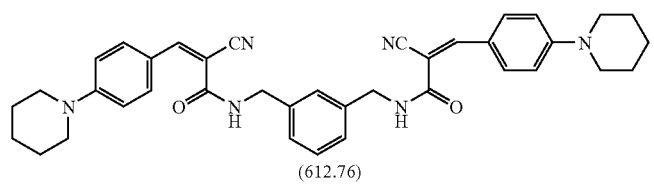<br>(612.76) |
| CP2013 | 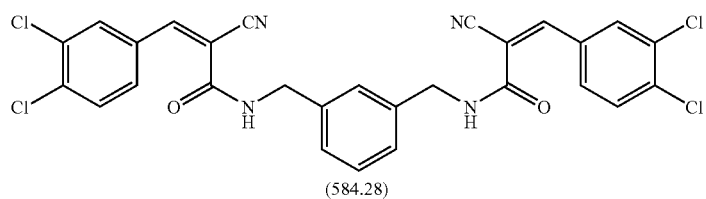<br>(584.28) |
| CP2014 | 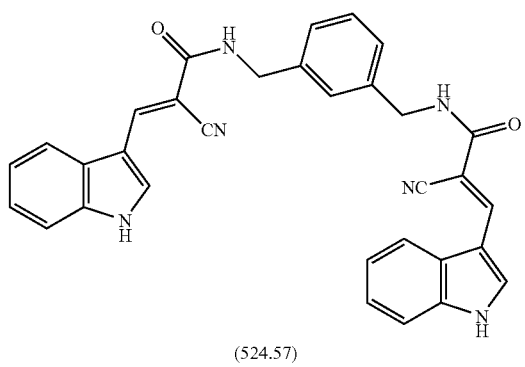<br>(524.57) |
| CP2016 | 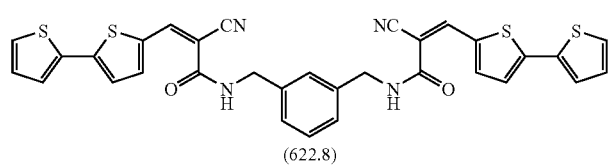<br>(622.8) |
| CP2022 | 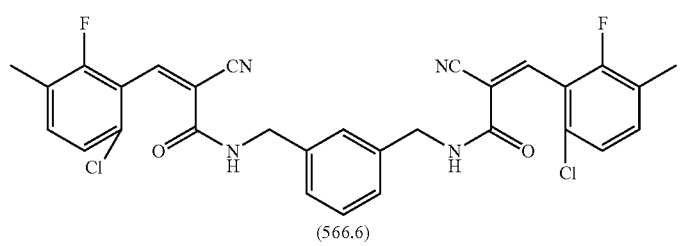<br>(566.6) |
| CP2028 | 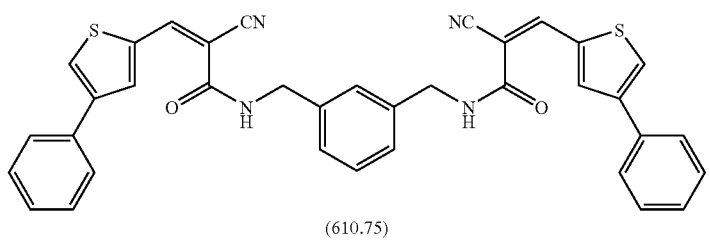<br>(610.75) |

TABLE A-continued

| Name of the Compound | Structure and M.F. and Molecular Weight |
|---|---|
| CP2030 | (568.49) |
| CP2024 | (558.67) |
| CP2025 | (527.57) |
| CP2015 | (508.13) |
| CP2026 | (636.29) |
| CP2029 | (646.82) |
| CP2031 | (445.48) |

TABLE A-continued

| Name of the Compound | Structure and M.F. and Molecular Weight |
|---|---|
| CP2021 | (536.5) |
| CP2034 | (736.26) |
| CP2023 | (682.68) |
| CP2035 | (566.6) |
| CP2037 | (426.43) |
| CP2025 | (524.51 |

TABLE A-continued
| Name of the Compound | Structure and M.F. and Molecular Weight |
|---|---|
| CP2032 | 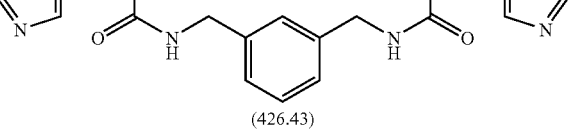<br>(426.43) |
| CP2031 | 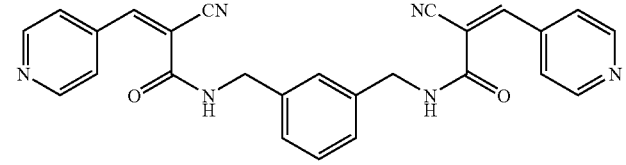<br>(448.48) |
| CP2036 | 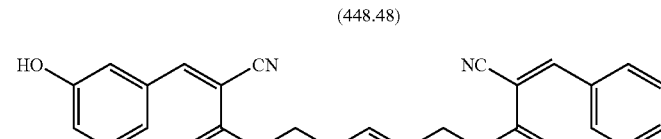<br>(478.5) |
| CP2016 | 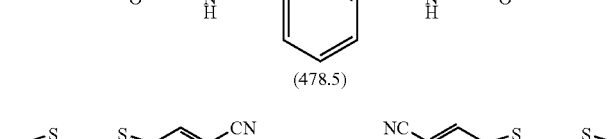<br>(622.8) |
| Eph2_wbz 202 | 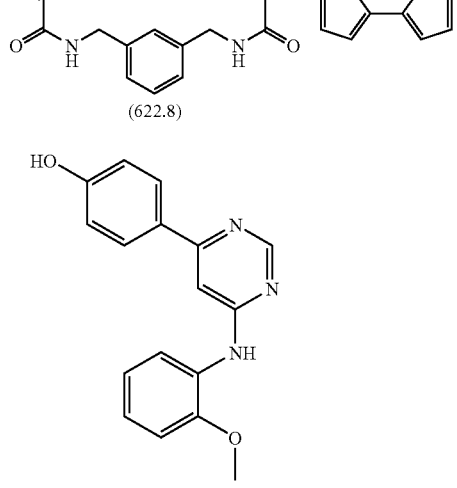<br>(293.32) |
| Eph2_wbz 203 | 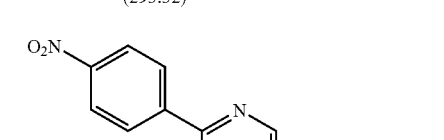<br>(322.32) |

TABLE A-continued
| Name of the Compound | Structure and M.F. and Molecular Weight |
|---|---|
| Eph2_wbz 204 | 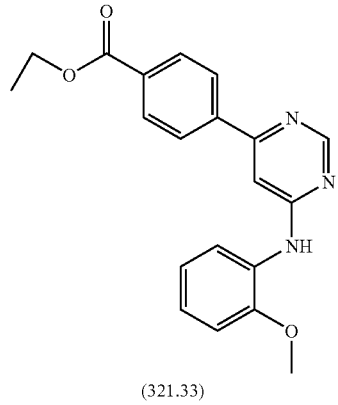<br>(321.33) |
| Eph2-wbz 206 | 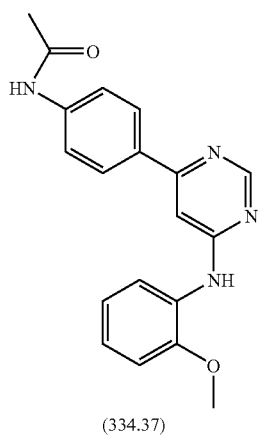<br>(334.37) |
| Eph2-wbz 207 | 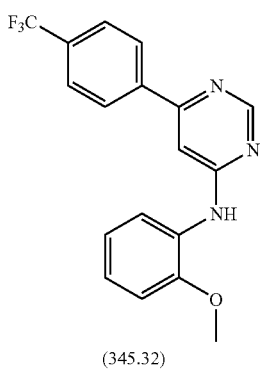<br>(345.32) |
| Eph2-wbz 208 | 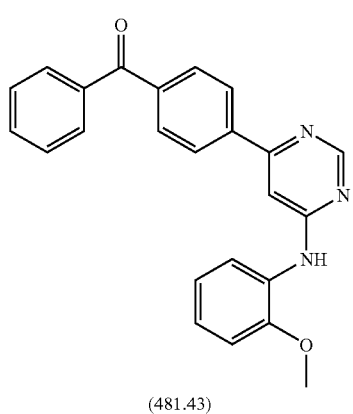<br>(481.43) |

TABLE A-continued
| Name of the Compound | Structure and M.F. and Molecular Weight |
|---|---|
| Eph2-wbz 210 | 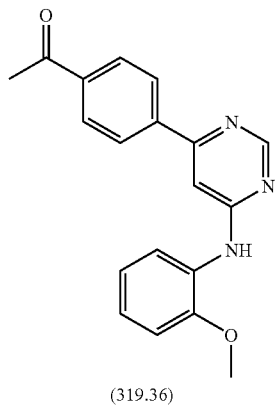<br>(319.36) |
| Eph2-wbz 211 | 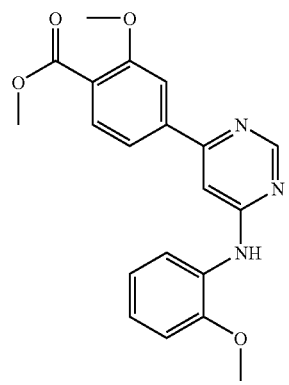<br>(365.38) |
| Eph2-wbz 212 | 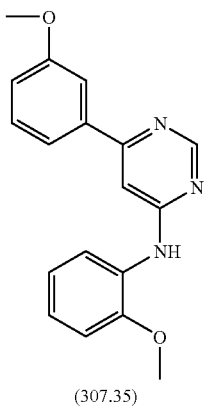<br>(307.35) |

TABLE A-continued
| Name of the Compound | Structure and M.F. and Molecular Weight |
|---|---|
| Eph2_wbz 216 | 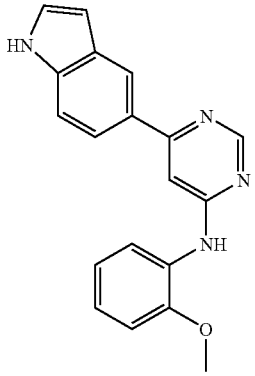 (316.36) |
| Eph2_wbz 217 | 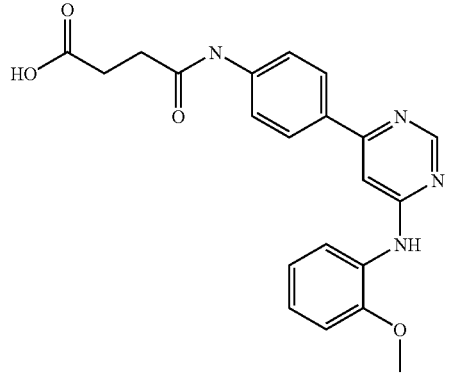 (391.4) |
| C-met Compounds | |
| dm-I-164 | 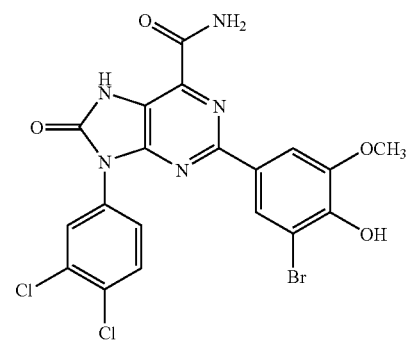 $C_{19}H_{12}BrCl_2N_5O_4$<br>Exact Mass: 522.945<br>Mol. Wt.: 525.1397 |

TABLE A-continued
| Name of the Compound | Structure and M.F. and Molecular Weight |
|---|---|
| dm-I-165 | 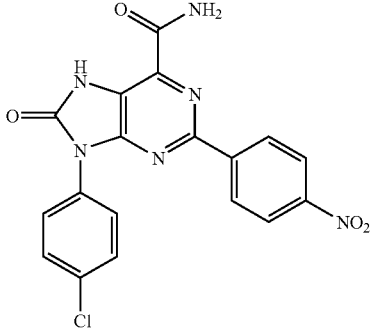<br>C₁₈H₁₁ClN₆O₄<br>Exact Mass: 410.053<br>Mol. Wt.: 410.7707 |
| dm-I-166 | 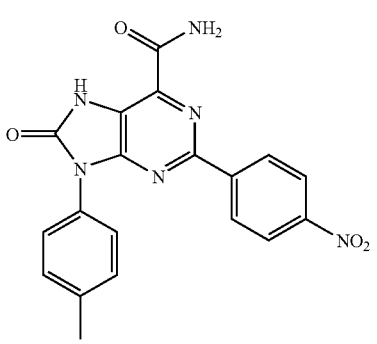<br>C₁₉H₁₄N₆O₄<br>Exact Mass: 390.1077<br>Mol. Wt.: 390.3523 |
| dm-I-173 | 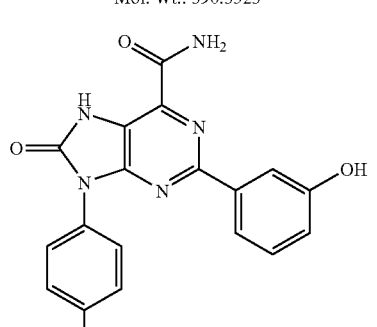<br>C₁₉H₁₅N₅O₃<br>Exact Mass: 361.1175<br>Mol. Wt.: 361.3541 |
| dm-I-174 | 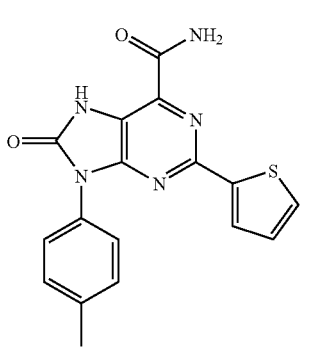<br>C₁₇H₁₃N₅O₂S<br>Exact Mass: 351.079<br>Mol. Wt.: 351.3824 |

TABLE A-continued
| Name of the Compound | Structure and M.F. and Molecular Weight |
| --- | --- |
| dm-I-175 | 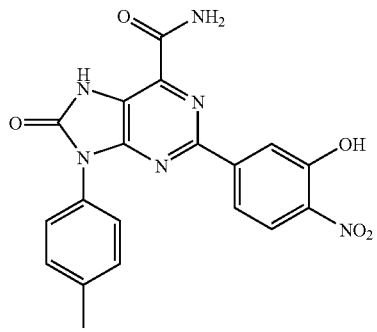<br>$C_{19}H_{14}N_6O_5$<br>Exact Mass: 406.1026<br>Mol. Wt.: 406.3517 |
| dm-I-176 | 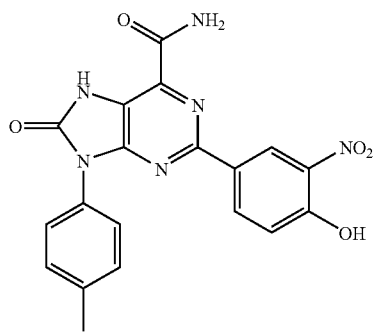<br>$C_{19}H_{14}N_6O_5$<br>Exact Mass: 406.1026<br>Mol. Wt.: 406.3517 |
| dm-I-177 | 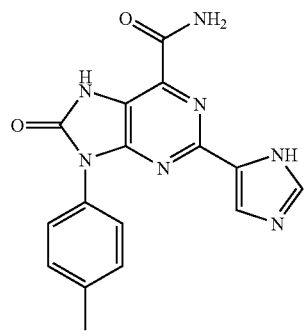<br>$C_{16}H_{13}N_7O_2$<br>Exact Mass: 335.1131<br>Mol. Wt.: 335.3201 |

TABLE A-continued
| Name of the Compound | Structure and M.F. and Molecular Weight |
|---|---|
| dm-I-178 | 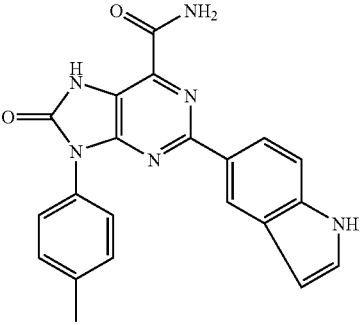<br>$C_{21}H_{15}N_6O_2$<br>Exact Mass: 384.1335<br>Mol. Wt.: 384.3907 |
| dm-I-179 | 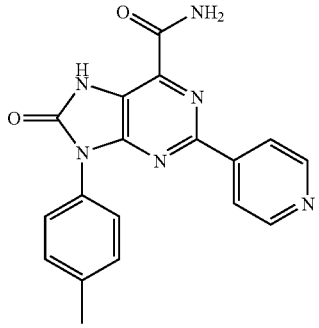<br>$C_{18}H_{14}N_6O_2$<br>Exact Mass: 346.1178<br>Mol. Wt.: 346.3428 |
| dm-I-180 | 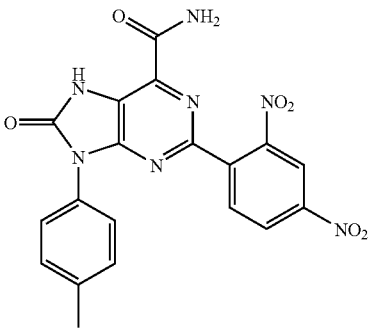<br>$C_{19}H_{13}N_7O_6$<br>Exact Mass: 435.0927<br>Mol. Wt.: 435.3498 |

TABLE A-continued
| Name of the Compound | Structure and M.F. and Molecular Weight |
|---|---|
| dm-I-183 | 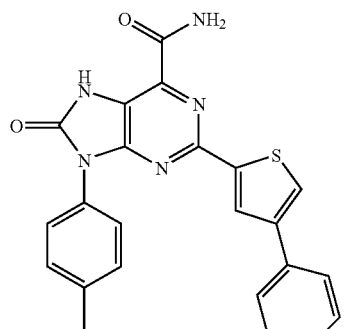<br>C$_{23}$H$_{17}$N$_5$O$_2$S<br>Exact Mass: 427.1103<br>Mol. Wt.: 427.4784 |
| dm-I-184 | 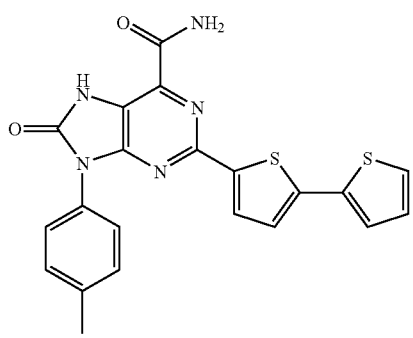<br>C$_{21}$H$_{15}$N$_5$O$_2$S$_2$<br>Exact Mass: 433.0667<br>Mol. Wt.: 433.5061 |
| dm-I-185 | 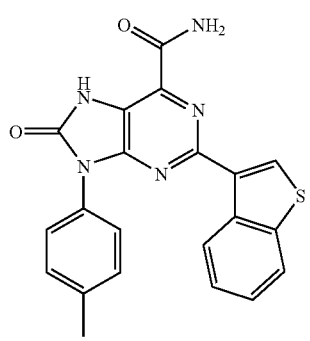<br>C$_{21}$H$_{15}$N$_5$O$_2$S<br>Exact Mass: 401.0946<br>Mol. Wt.: 401.4411 |

TABLE A-continued
| Name of the Compound | Structure and M.F. and Molecular Weight |
|---|---|
| dm-I-186 | 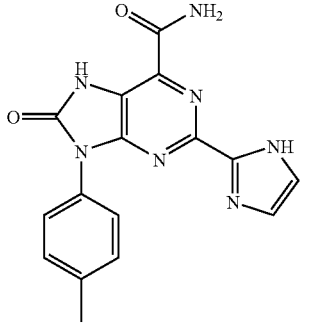<br>C₁₆H₁₃N₇O₂<br>Exact Mass: 335.1131<br>Mol. Wt.: 335.3201 |
| dm-I-187 | 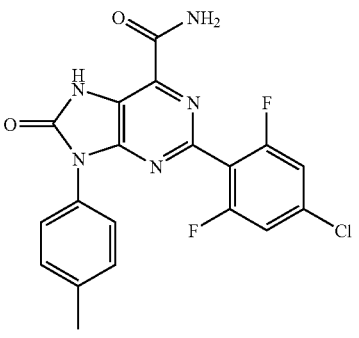<br>C₁₉H₁₂ClF₂N₅O₂<br>Exact Mass: 415.0648<br>Mol. Wt.: 415.7807 |
| dm-I-189 | 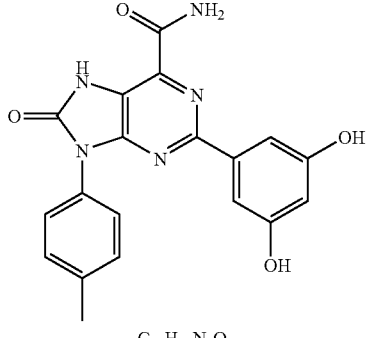<br>C₁₉H₁₅N₅O₄<br>Exact Mass: 377.1124<br>Mol. Wt.: 377.3535 |
| dm-I-190 | 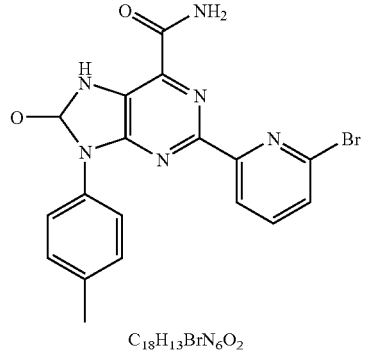<br>C₁₈H₁₃BrN₆O₂<br>Exact Mass: 424.0283<br>Mol. Wt.: 425.2388 |

TABLE A-continued
| Name of the Compound | Structure and M.F. and Molecular Weight |
|---|---|
| dm-I-192 | 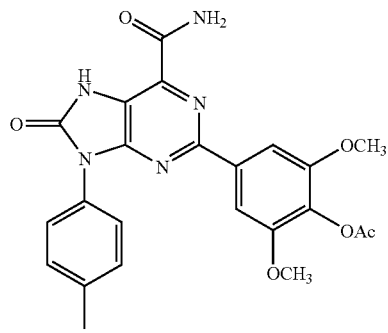<br>C$_{23}$H$_{21}$N$_5$O$_6$<br>Exact Mass: 463.1492<br>Mol. Wt.: 463.4427 |
| dm-I-193 | 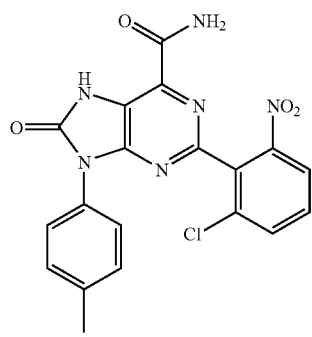<br>C$_{19}$H$_{13}$ClN$_6$O$_4$<br>Exact Mass: 424.0687<br>Mol. Wt.: 424.7973 |
| dm-I-194 | 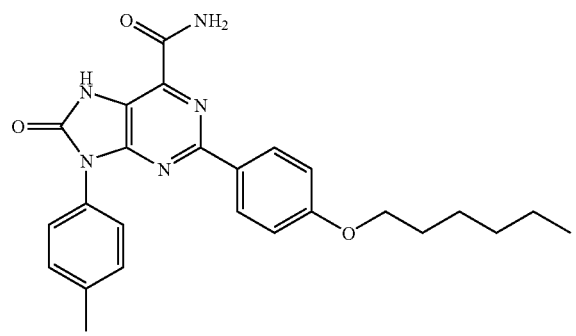<br>C$_{25}$H$_{27}$N$_5$O$_3$<br>Exact Mass: 445.2114<br>Mol. Wt.: 445.5136 |

TABLE A-continued
| Name of the Compound | Structure and M.F. and Molecular Weight |
|---|---|
| dm-I-195 | 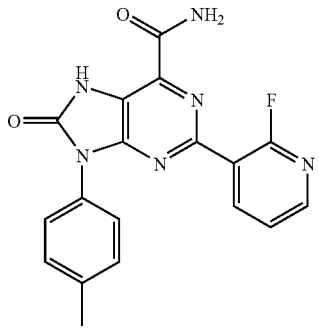<br>C₁₈H₁₃FN₆O₂<br>Exact Mass: 364.1084<br>Mol. Wt.: 364.3332 |
| dm-I-196 | 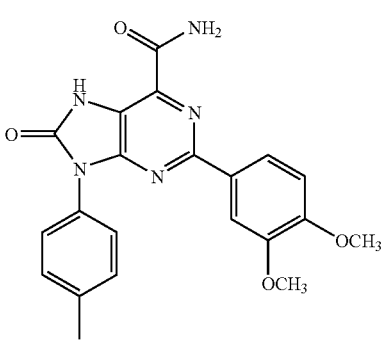<br>C₂₁H₁₉N₅O₄<br>Exact Mass: 405.1437<br>Mol. Wt.: 405.4067 |
| dm-I-197 | 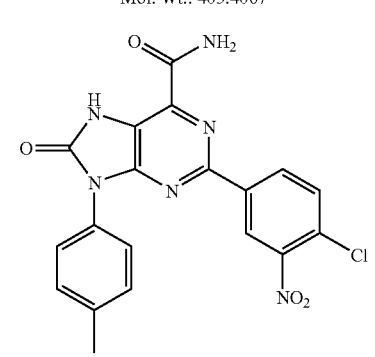<br>C₁₉H₁₃ClN₆O₄<br>Exact Mass: 424.0687<br>Mol. Wt.: 424.7973 |
| dm-I-198 | 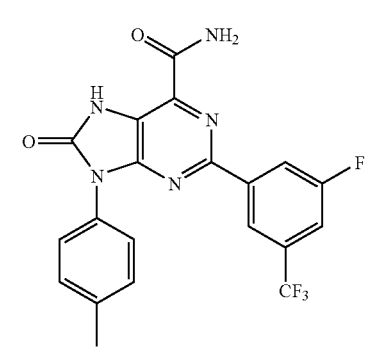<br>C₂₀H₁₃F₄N₅O₂<br>Exact Mass: 431.1005<br>Mol. Wt.: 431.3431 |

TABLE A-continued
| Name of the Compound | Structure and M.F. and Molecular Weight |
|---|---|
| dm-I-199 | 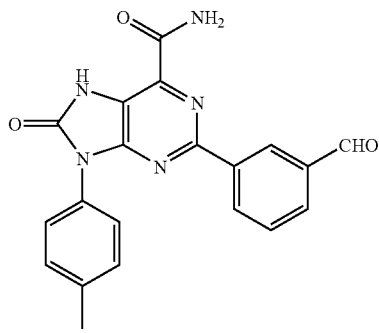 C$_{20}$H$_{15}$N$_5$O$_3$<br>Exact Mass: 373.1175<br>Mol. Wt.: 373.3648 |
| dm-I-200 | 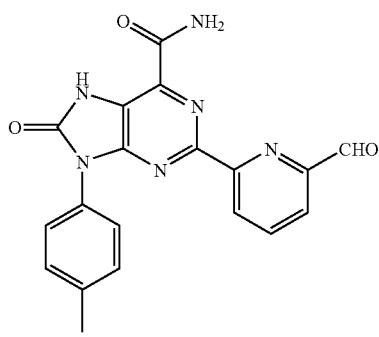 C$_{19}$H$_{14}$N$_6$O$_3$<br>Exact Mass: 374.1127<br>Mol. Wt.: 374.3529 |
| dm-I-201 | 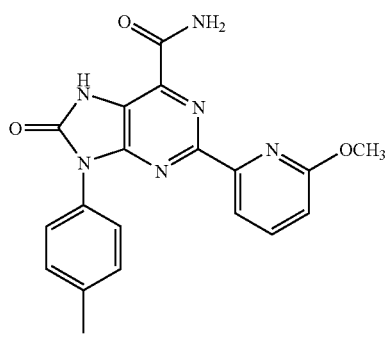 C$_{19}$H$_{16}$N$_6$O$_3$<br>Exact Mass: 376.1284<br>Mol. Wt.: 376.3687 |

TABLE A-continued
| Name of the Compound | Structure and M.F. and Molecular Weight |
|---|---|
| dm-I-202 | 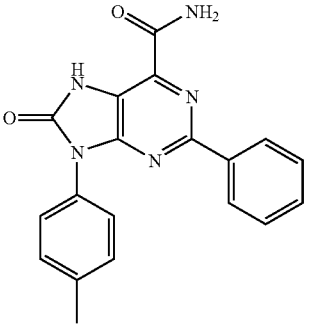<br>C₁₉H₁₅N₅O₂<br>Exact Mass: 345.1226<br>Mol. Wt.: 345.3547 |
| dm-I-203 | 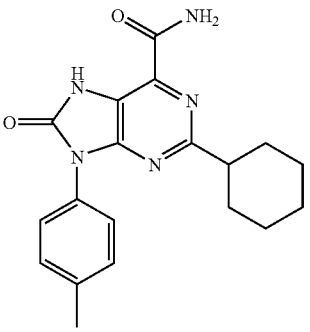<br>C₁₉H₂₁N₅O₂<br>Exact Mass: 351.1695<br>Mol. Wt.: 351.4023 |
| dm-I-205 | 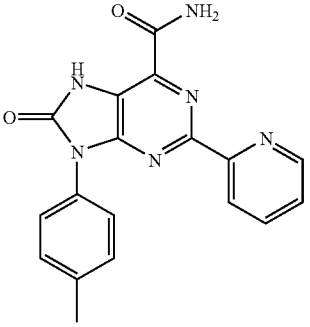<br>C₁₈H₁₄N₆O₂<br>Exact Mass: 346.1178<br>Mol. Wt.: 346.3428 |
| SAHA-1 | 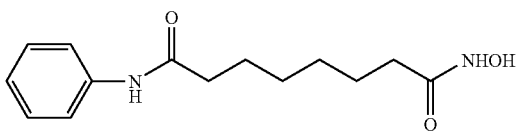<br>C₁₄H₂₀N₂O₃<br>Exact Mass: 264.1474<br>Mol. Wt.: 264.3202 |

TABLE A-continued
| Name of the Compound | Structure and M.F. and Molecular Weight |
|---|---|
| 2F-SAHA | 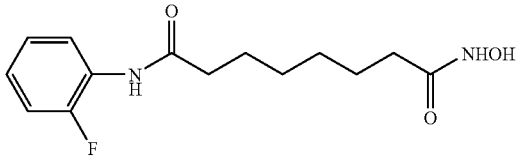<br>$C_{14}H_{19}FN_2O_3$<br>Exact Mass: 282.138<br>Mol. Wt.: 282.3107 |
| 3F-SAHA | 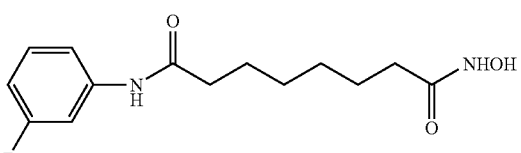<br>$C_{14}H_{19}FN_2O_3$<br>Exact Mass: 282.138<br>Mol. Wt.: 282.3107 |
| 4F-SAHA | 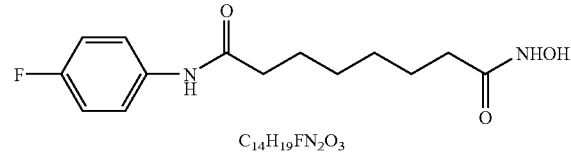<br>$C_{14}H_{19}FN_2O_3$<br>Exact Mass: 282.138<br>Mol. Wt.: 282.3107 |
| 3I-SAHA | 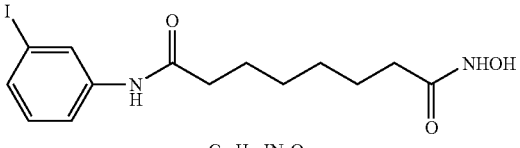<br>$C_{14}H_{19}IN_2O_3$<br>Exact Mass: 390.044<br>Mol. Wt.: 390.2167 |
| AS-605091 | 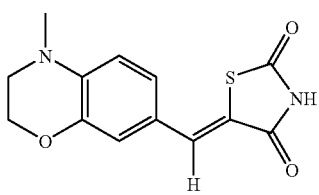<br>$C_{13}H_{12}N_2O_3S$<br>Exact Mass: 276.0569<br>Mol. Wt.: 276.311 |
| AS-604850 | 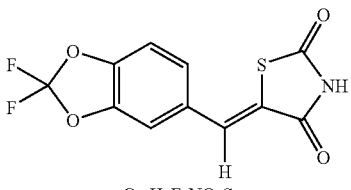<br>$C_{11}H_5F_2NO_4S$<br>Exact Mass: 284.9907<br>Mol. Wt.: 285.2235 |

TABLE A-continued
| Name of the Compound | Structure and M.F. and Molecular Weight |
|---|---|
| AS-605240 | 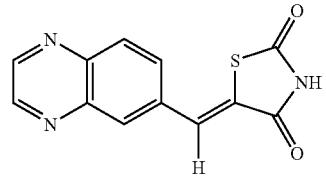<br>$C_{12}H_7N_3O_2S$<br>Exact Mass: 257.0259<br>Mol. Wt.: 257.2679 |
| JGAP-11 | 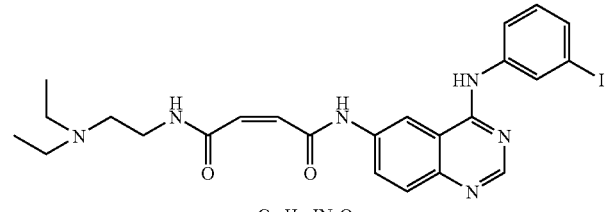<br>$C_{24}H_{27}IN_6O_2$<br>Exact Mass: 558.124<br>Mol. Wt.: 558.4146 |
| JGAP-13 | 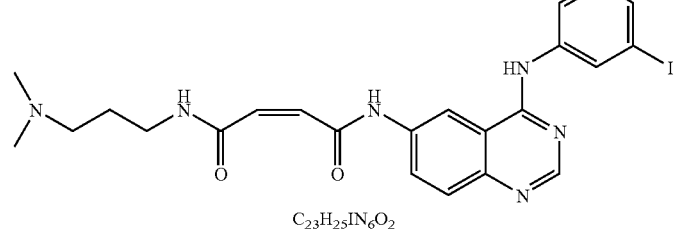<br>$C_{23}H_{25}IN_6O_2$<br>Exact Mass: 544.1084<br>Mol. Wt.: 544.3881 |
| JGAP-5 | 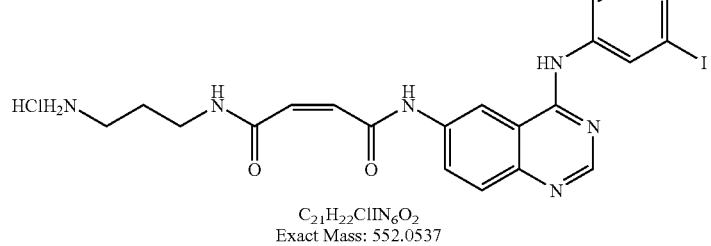<br>$C_{21}H_{22}ClIN_6O_2$<br>Exact Mass: 552.0537<br>Mol. Wt.: 552.7958 |
| JGAP-7 | 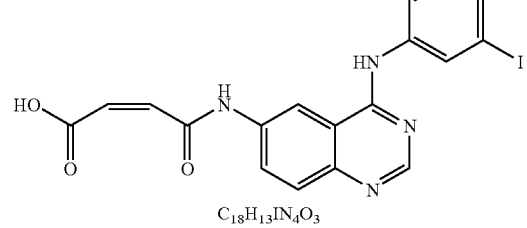<br>$C_{18}H_{13}IN_4O_3$<br>Exact Mass: 460.0032<br>Mol. Wt.: 460.2253 |

TABLE A-continued
| Name of the Compound | Structure and M.F. and Molecular Weight |
|---|---|
| APcK-101 | 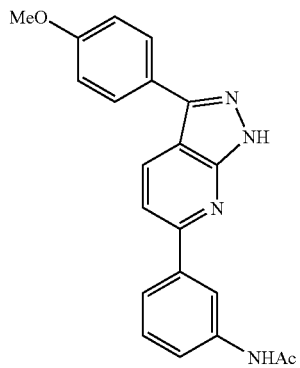$C_{21}H_{18}N_4O_2$<br>Exact Mass: 358.143<br>Mol. Wt.: 358.3932 |
| APcK-102 | 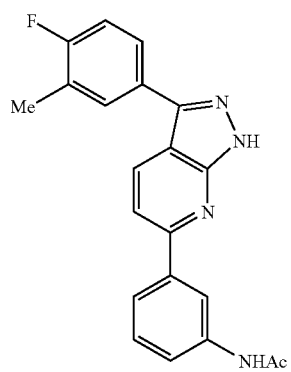$C_{21}H_{17}FN_4O$<br>Exact Mass: 360.1386<br>Mol. Wt.: 360.3843 |
| APcK-103 | 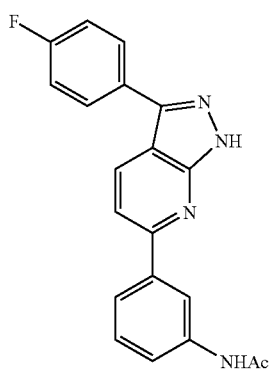$C_{20}H_{15}FN_4O$<br>Exact Mass: 346.123<br>Mol. Wt.: 346.3577 |

TABLE A-continued
| Name of the Compound | Structure and M.F. and Molecular Weight |
|---|---|
| APcK-104 | 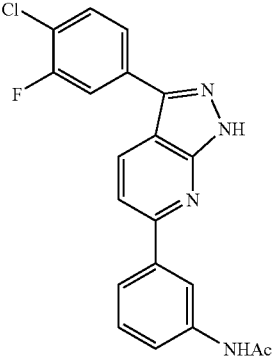<br>C$_{20}$H$_{14}$ClFN$_4$O<br>Exact Mass: 380.084<br>Mol. Wt.: 380.8028 |
| APcK-105 | 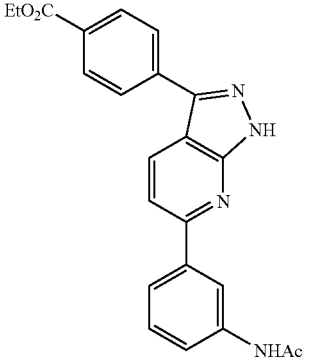<br>C$_{23}$H$_{20}$N$_4$O$_3$<br>Exact Mass: 400.1535<br>Mol. Wt.: 400.4299 |
| APcK-106 | 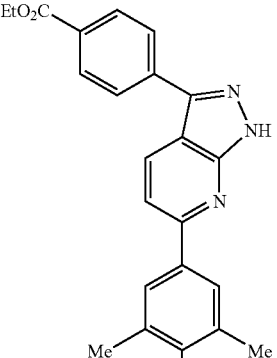<br>C$_{23}$H$_{21}$N$_3$O$_3$<br>Exact Mass: 387.1583<br>Mol. Wt.: 387.4311 |

TABLE A-continued
| Name of the Compound | Structure and M.F. and Molecular Weight |
|---|---|
| APcK-107 | 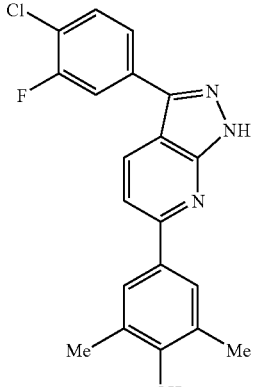<br>$C_{20}H_{15}ClFN_3O$<br>Exact Mass: 367.0888<br>Mol. Wt.: 367.804 |
| APcK-108 | 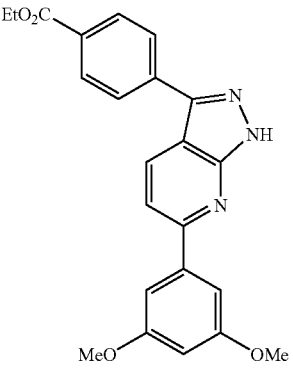<br>$C_{23}H_{21}N_3O_4$<br>Exact Mass: 403.1532<br>Mol. Wt.: 403.4305 |
| APcK-109 | 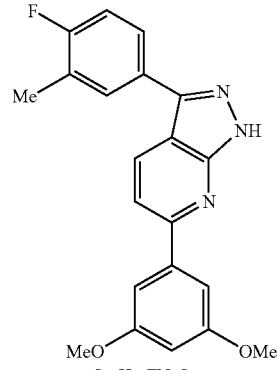<br>$C_{21}H_{18}FN_3O_2$<br>Exact Mass: 363.1383<br>Mol. Wt.: 363.3849 |

TABLE A-continued
| Name of the Compound | Structure and M.F. and Molecular Weight |
|---|---|
| APcK-110 | 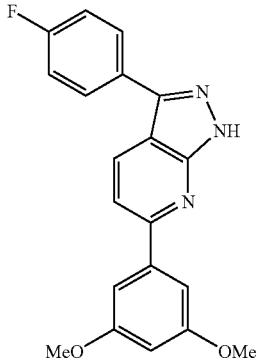<br>C₂₀H₁₆FN₃O₂<br>Exact Mass: 349.1227<br>Mol. Wt.: 349.3583 |
| APcK-111 | 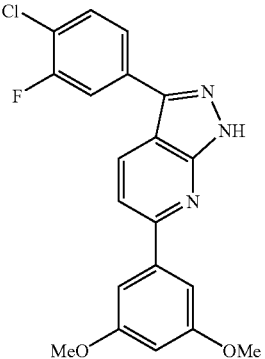<br>C₂₀H₁₅ClFN₃O₂<br>Exact Mass: 383.0837<br>Mol. Wt.: 383.8034 |
| APcK-112 | 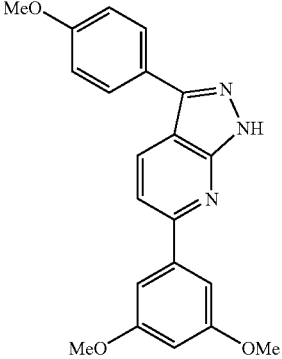<br>C₂₁H₁₉N₃O₃<br>Exact Mass: 361.1426<br>Mol. Wt.: 361.3939 |

TABLE A-continued
| Name of the Compound | Structure and M.F. and Molecular Weight |
|---|---|
| APcK-114 | 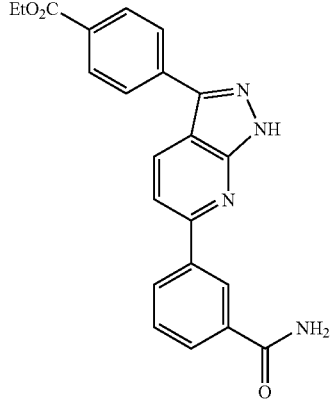
C$_{22}$H$_{18}$N$_4$O$_3$
Exact Mass: 386.1379
Mol. Wt.: 386.4033 |
| APcK-115 | 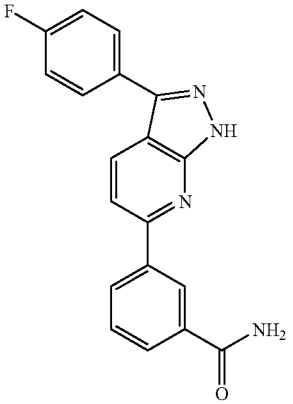
C$_{19}$H$_{13}$FN$_4$O
Exact Mass: 332.1073
Mol. Wt.: 332.3311 |
| APCK-116 | 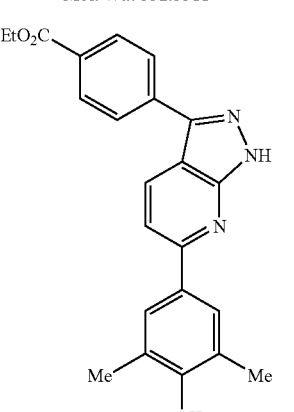
C$_{18}$H$_{11}$ClFN$_3$O
Exact Mass: 339.0575
Mol. Wt.: 339.7508 |

TABLE A-continued
| Name of the Compound | Structure and M.F. and Molecular Weight |
|---|---|
| APCK-17 | 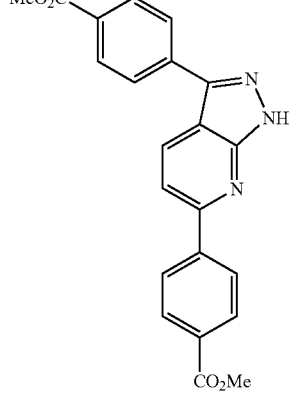<br>$C_{22}H_{17}N_3O_4$<br>Exact Mass: 387.12191<br>Mol. Wt.: 387.38808 |
| APCK-18 | 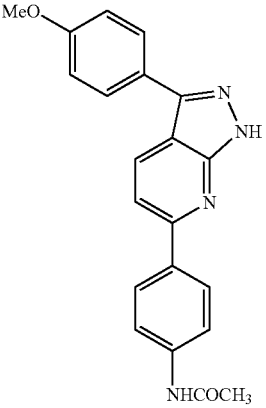<br>$C_{21}H_{18}N_4O_2$<br>Exact Mass: 358.14298<br>Mol. Wt.: 358.39322 |
| APCK-19 | 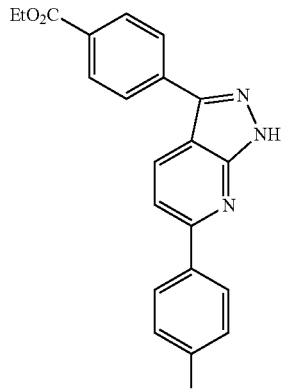<br>$C_{23}H_{20}N_4O_3$<br>Exact Mass: 400.1535<br>Mol. Wt.: 400.4299 |

TABLE A-continued
| Name of the Compound | Structure and M.F. and Molecular Weight |
|---|---|
| APCK-20 | 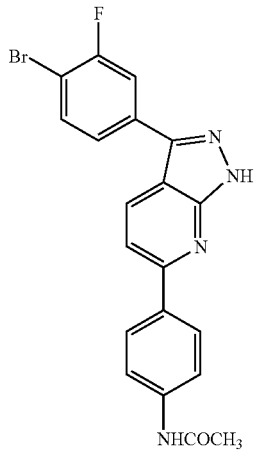<br>C₂₀H₁₄BrFN₄O<br>Exact Mass: 424.0335<br>Mol. Wt.: 425.2538 |
| APCK-21 | 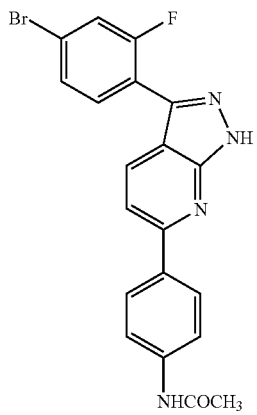<br>C₂₀H₁₄BrFN₄O<br>Exact Mass: 424.0335<br>Mol. Wt.: 425.2538 |
| APCK-22 | 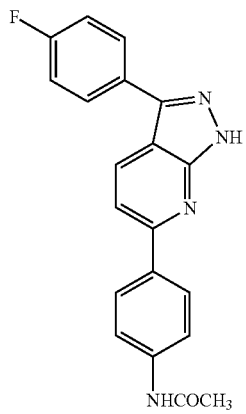<br>C₂₀H₁₅FN₄O<br>Exact Mass: 346.123<br>Mol. Wt.: 346.3577 |

TABLE A-continued
| Name of the Compound | Structure and M.F. and Molecular Weight |
|---|---|
| APCK-23 | 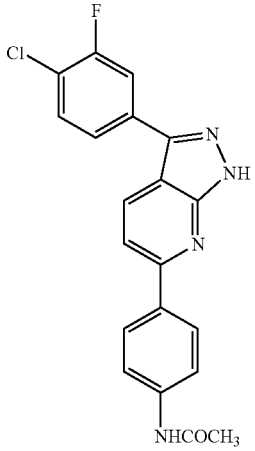<br>C$_{20}$H$_{14}$ClFN$_4$O<br>Exact Mass: 380.084<br>Mol. Wt.: 380.8028 |
| APCK-24 | 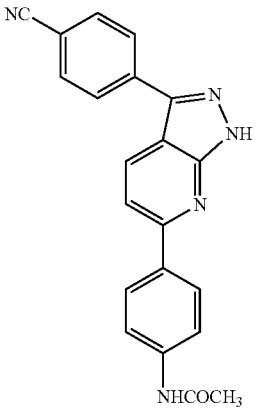<br>C$_{21}$H$_{15}$N$_5$O<br>Exact Mass: 353.1277<br>Mol. Wt.: 353.3767 |
| APCK-25 | 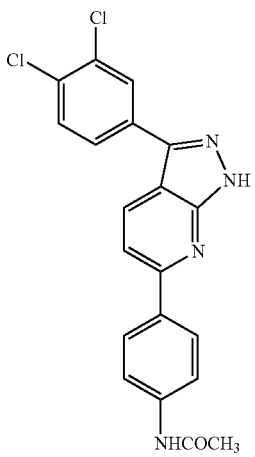<br>C$_{20}$H$_{14}$Cl$_2$N$_4$O<br>Exact Mass: 396.0545<br>Mol. Wt.: 397.2574 |

TABLE A-continued
| Name of the Compound | Structure and M.F. and Molecular Weight |
|---|---|
| APCK-26 | 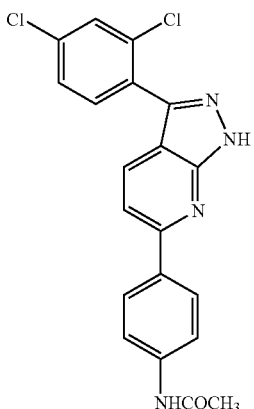<br>$C_{20}H_{14}Cl_2N_4O$<br>Exact Mass: 396.0545<br>Mol. Wt.: 397.2574 |
| APCK-27 | 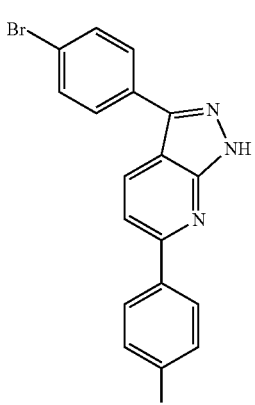<br>$C_{20}H_{15}BrN_4O$<br>Exact Mass: 406.0429<br>Mol. Wt.: 407.2633 |
| APCK-28 | 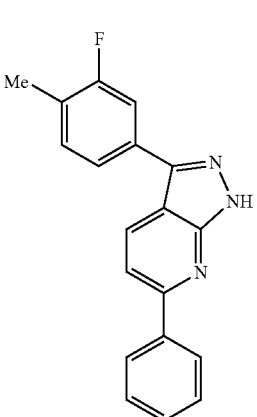<br>$C_{21}H_{17}FN_4O$<br>Exact Mass: 360.1386<br>Mol. Wt.: 360.3843 |

TABLE A-continued
| Name of the Compound | Structure and M.F. and Molecular Weight |
|---|---|
| APCK-29 | 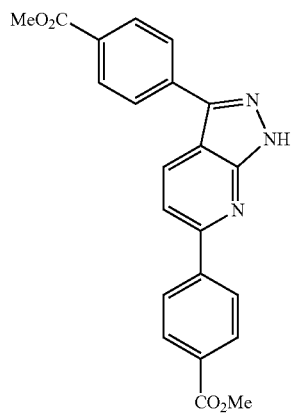<br>C$_{21}$H$_{18}$N$_4$O<br>Exact Mass: 342.1481<br>Mol. Wt.: 342.3938 |
| APCK-30 | 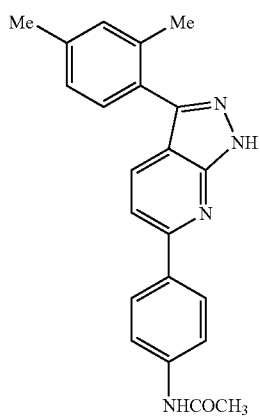<br>C$_{22}$H$_{20}$N$_4$O<br>Exact Mass: 356.1637<br>Mol. Wt.: 356.4204 |
| APCK-31 | 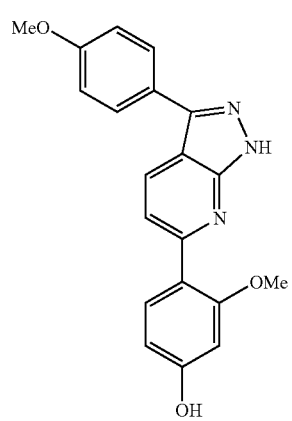<br>C$_{20}$H$_{17}$N$_3$O$_3$<br>Exact Mass: 347.12699<br>Mol. Wt.: 347.36728 |

TABLE A-continued
| Name of the Compound | Structure and M.F. and Molecular Weight |
|---|---|
| APCK-32 | 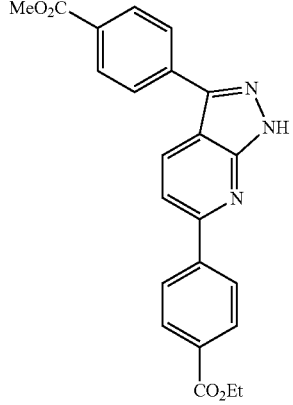<br>$C_{23}H_{19}N_3O_4$<br>Exact Mass: 401.13756<br>Mol. Wt.: 401.41466 |
| APCK-33 | 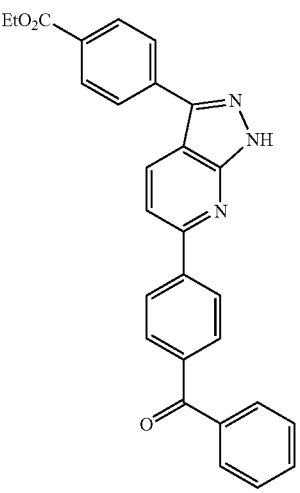<br>$C_{28}H_{21}N_3O_3$<br>Exact Mass: 447.15829<br>Mol. Wt.: 447.48464 |
| APCK-34 | 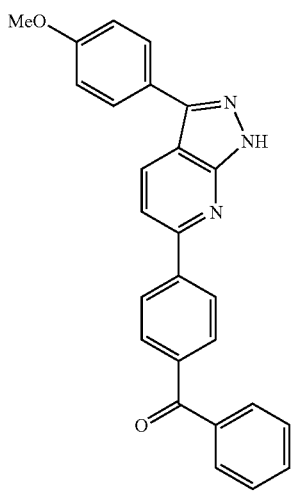<br>$C_{26}H_{19}N_3O_2$<br>Exact Mass: 405.14773<br>Mol. Wt.: 405.44796 |

TABLE A-continued
| Name of the Compound | Structure and M.F. and Molecular Weight |
|---|---|
| APCK-35 | 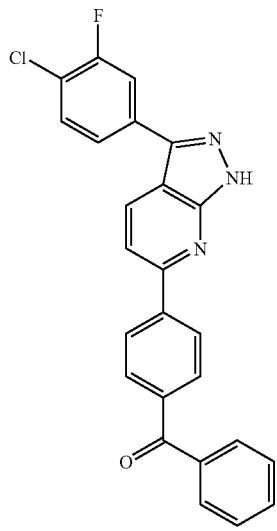<br>$C_{25}H_{15}ClFN_3O$<br>Exact Mass: 427.08877<br>Mol. Wt.: 427.8575 |
| APCK-36 | 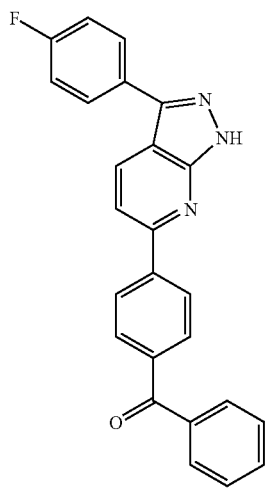<br>$C_{25}H_{16}FN_3O$<br>Exact Mass: 393.12774<br>Mol. Wt.: 393.41244 |

TABLE A-continued
| Name of the Compound | Structure and M.F. and Molecular Weight |
|---|---|
| APCK-37 | 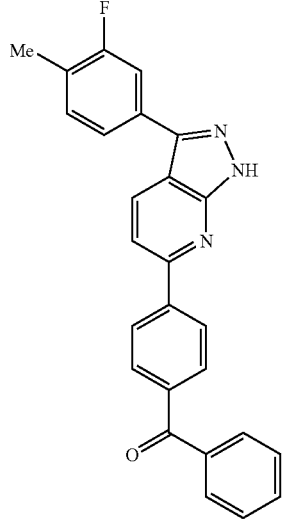<br>$C_{26}H_{18}FN_3O$<br>Exact Mass: 407.14339<br>Mol. Wt.: 407.43902 |
| APCK-38 | 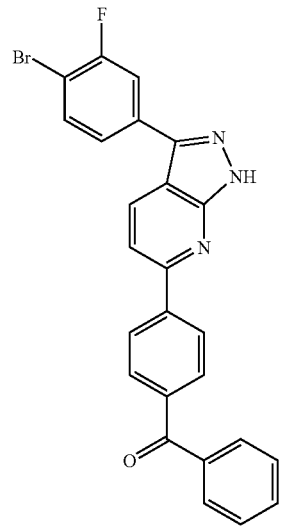<br>$C_{25}H_{15}BrFN_3O$<br>Exact Mass: 471.03825<br>Mol. Wt.: 472.3085 |

TABLE A-continued
| Name of the Compound | Structure and M.F. and Molecular Weight |
|---|---|
| APCK-39 | 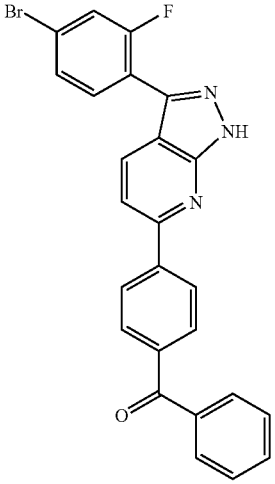<br>$C_{25}H_{15}BrFN_3O$<br>Exact Mass: 471.03825<br>Mol. Wt.: 472.3085 |
| APCK-40 | 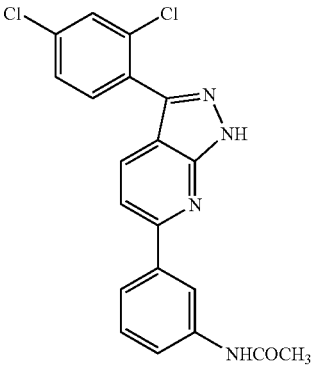<br>$C_{20}H_{14}Cl_2N_4O$<br>Exact Mass: 396.05447<br>Mol. Wt.: 397.25736 |
| APCK-41 | 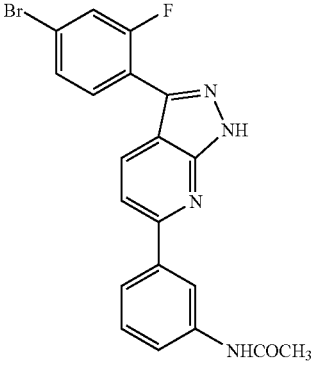<br>$C_{20}H_{14}BrFN_4O$<br>Exact Mass: 424.0335<br>Mol. Wt.: 425.25376 |

TABLE A-continued
| Name of the Compound | Structure and M.F. and Molecular Weight |
|---|---|
| APCK-42 | 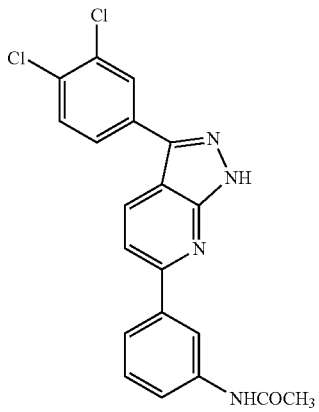<br>$C_{20}H_{14}Cl_2N_4O$<br>Exact Mass: 396.05447<br>Mol. Wt.: 397.25736 |
| APCK-43 | 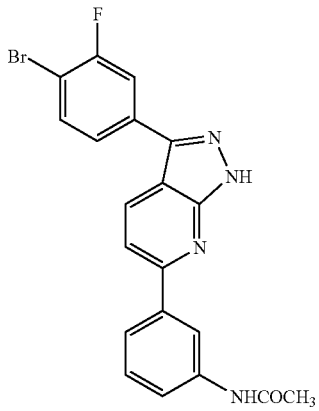<br>$C_{20}H_{14}BrFN_4O$<br>Exact Mass: 424.0335<br>Mol. Wt.: 425.25376 |
| APCK-44 | 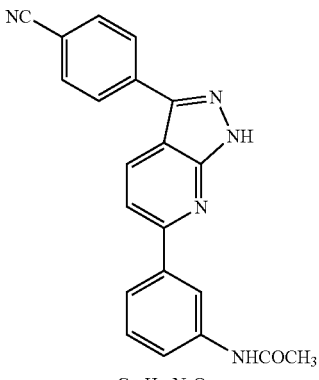<br>$C_{21}H_{15}N_5O$<br>Exact Mass: 353.12766<br>Mol. Wt.: 353.3767 |

TABLE A-continued
| Name of the Compound | Structure and M.F. and Molecular Weight |
|---|---|
| APCK-45 | 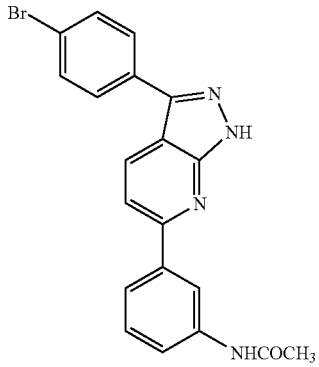<br>C₂₀H₁₅BrN₄O<br>Exact Mass: 406.04292<br>Mol. Wt.: 407.2633 |
| APCK-46 | 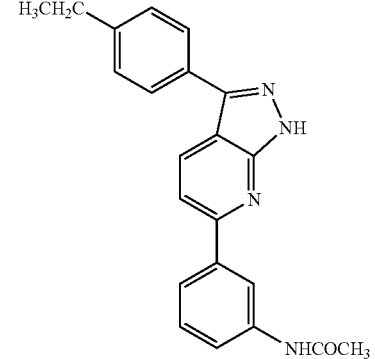<br>C₂₂H₂₀N₄O<br>Exact Mass: 356.16371<br>Mol. Wt.: 356.4204 |
| APCK-47 | 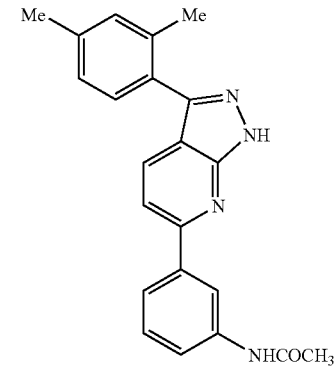<br>C₂₂H₂₀N₄O<br>Exact Mass: 356.16371<br>Mol. Wt.: 356.4204 |

TABLE A-continued
| Name of the Compound | Structure and M.F. and Molecular Weight |
|---|---|
| APcK-48 | 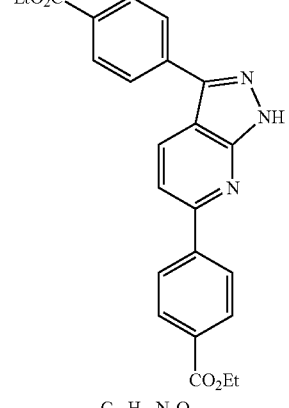<br>$C_{24}H_{21}N_3O_4$<br>Exact Mass: 415.15321<br>Mol. Wt.: 415.44124 |
| APcK-49 | 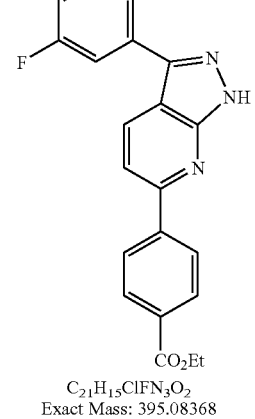<br>$C_{21}H_{15}ClFN_3O_2$<br>Exact Mass: 395.08368<br>Mol. Wt.: 395.8141 |
| APcK-50 | 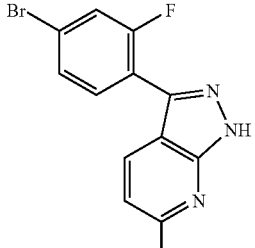<br>$C_{21}H_{15}BrFN_3O_2$<br>Exact Mass: 439.03317<br>Mol. Wt.: 440.2651 |

TABLE A-continued
| Name of the Compound | Structure and M.F. and Molecular Weight |
|---|---|
| APcK-51 | 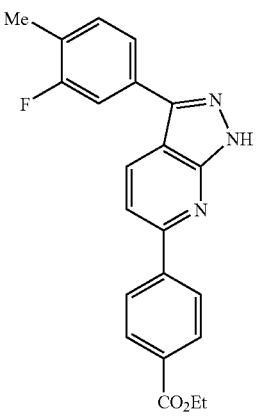<br>C₂₂H₁₈FN₃O₂<br>Exact Mass: 375.13831<br>Mol. Wt.: 375.39562 |
| APcK-53 | 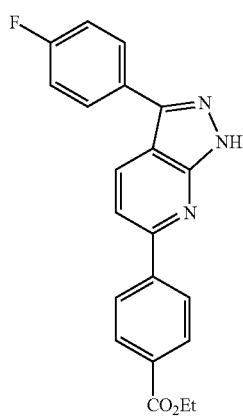<br>C₂₁H₁₆FN₃O₂<br>Exact Mass: 361.12265<br>Mol. Wt.: 361.36904 |
| APcK-54 | 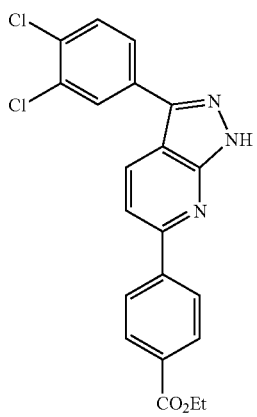<br>C₂₁H₁₅Cl₂N₃O₂<br>Exact Mass: 411.05413<br>Mol. Wt.: 412.2687 |

TABLE A-continued
| Name of the Compound | Structure and M.F. and Molecular Weight |
|---|---|
| APcK-55 | 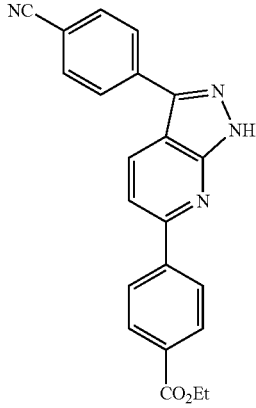<br>C$_{22}$H$_{16}$N$_4$O$_2$<br>Exact Mass: 368.12733<br>Mol. Wt.: 368.38804 |
| APcK-56 | 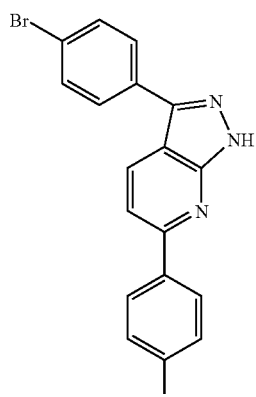<br>C$_{21}$H$_{16}$BrN$_3$O$_2$<br>Exact Mass: 421.04259<br>Mol. Wt.: 422.27464 |
| APcK-58 | 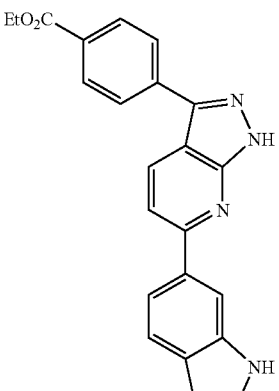<br>C$_{23}$H$_{18}$N$_4$O$_2$<br>Exact Mass: 382.14298<br>Mol. Wt.: 382.41462 |

TABLE A-continued
| Name of the Compound | Structure and M.F. and Molecular Weight |
|---|---|
| butyrolactones-1 | 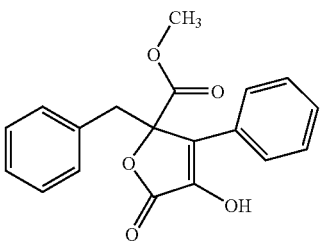<br>$C_{19}H_{16}O_5$<br>Exact Mass: 324.0998<br>Mol. Wt.: 324.3273 |
| butyrolactones-2 | 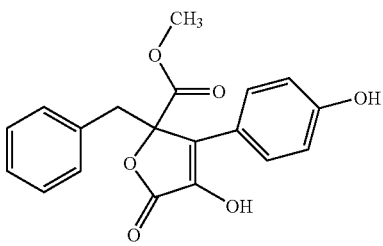<br>$C_{19}H_{16}O_6$<br>Exact Mass: 340.0947<br>Mol. Wt.: 340.3267 |
| butyrolactones-Bio | Biotinylated Compound<br>MW-583.3 MH$^+$<br>MW-583.3 MH$^+$ |
PD Compounds
| | |
|---|---|
| PD166326 | 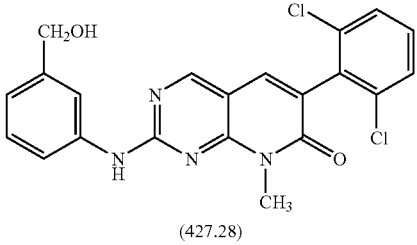<br>(427.28) |
| PD-Br | 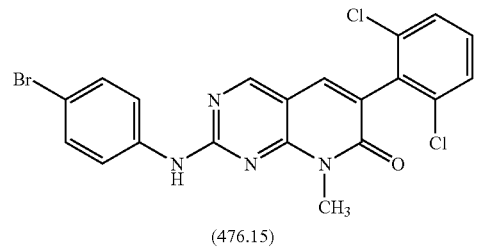<br>(476.15) |
| YYA26b | 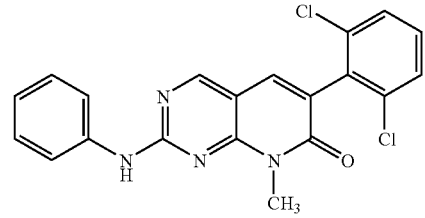<br>(397.26) |

TABLE A-continued
| Name of the Compound | Structure and M.F. and Molecular Weight |
|---|---|
| YYA103 | 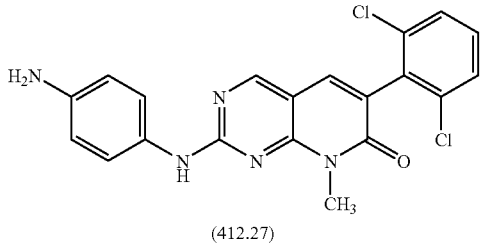 (412.27) |
| YYA104 | 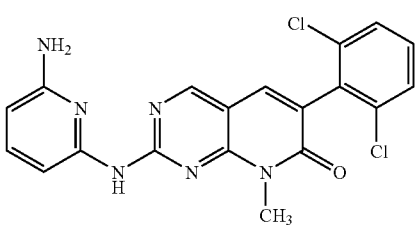 (413.26) |
| YYA105 | 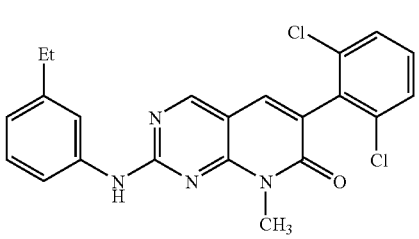 (425.31) |
| YYA187 | 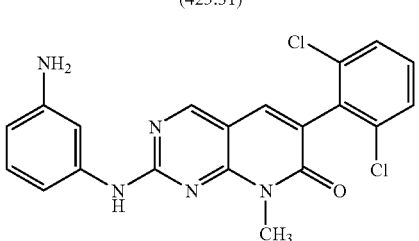 (412.27) |
| YYA188 | 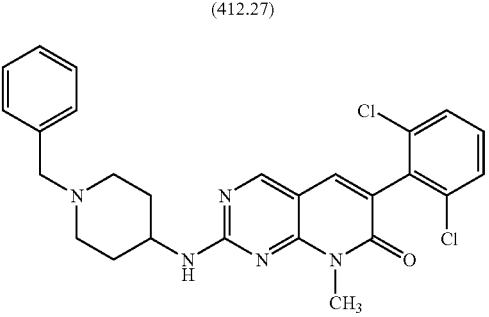 (494.42) |
| YYA190 | 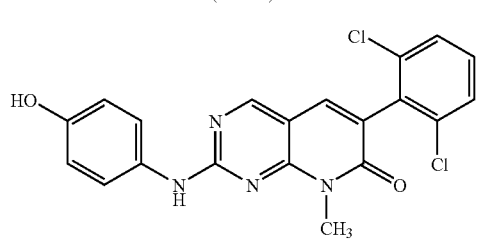 (413.26) |

TABLE A-continued
| Name of the Compound | Structure and M.F. and Molecular Weight |
|---|---|
| YYA194 | 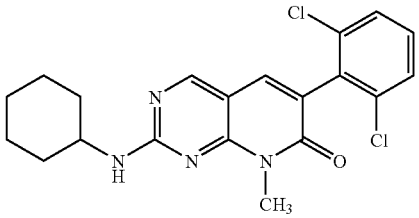<br>(403.3) |
| YYA195 | 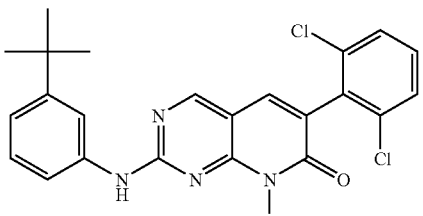<br>(453.36) |
C-Met Compounds
| | |
|---|---|
| YYA180 | 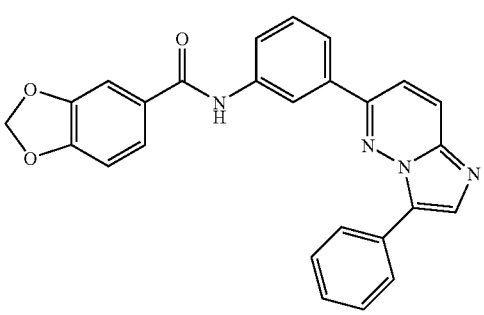<br>(435.43) |
| YYA181 | 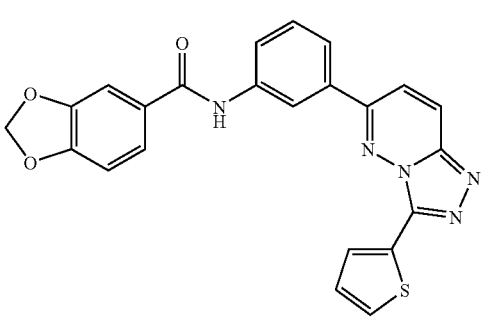<br>(441.46) |
| YYB19 | 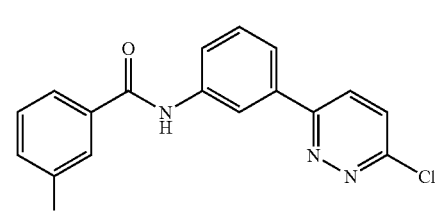<br>(354.75) |

TABLE A-continued
| Name of the Compound | Structure and M.F. and Molecular Weight |
|---|---|
| YYB20 | 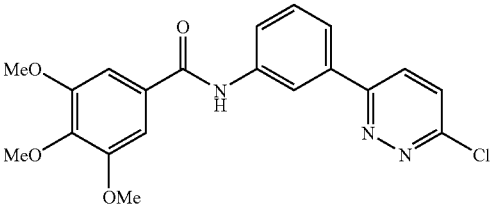<br>(399.83) |
| YYB21 | 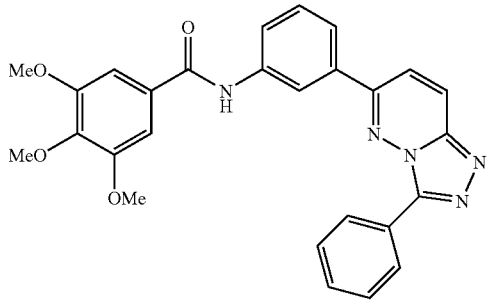<br>(481.5) |
| YYB22 | 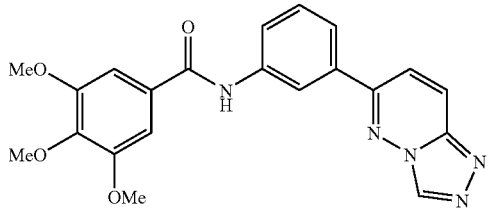<br>(405.41) |
| YYB23 | 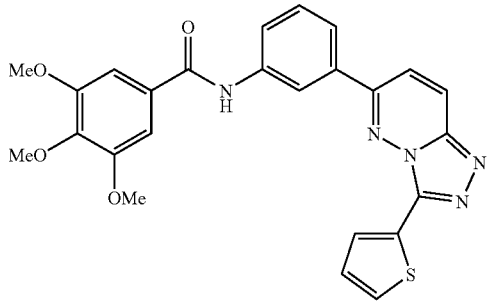<br>(487.53) |
| YYB24 | 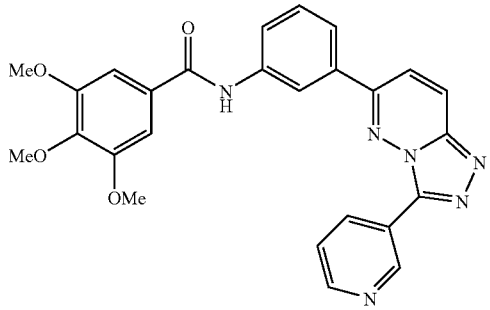<br>(482.49) |

TABLE A-continued
| Name of the Compound | Structure and M.F. and Molecular Weight |
|---|---|
| YYB25 | 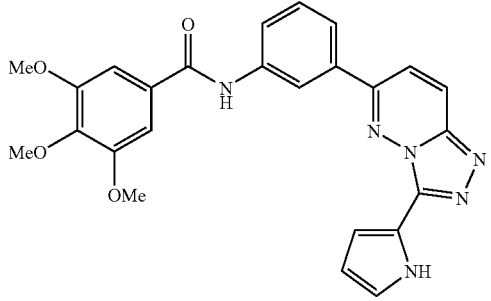<br>(470.48) |
| YYB28 | <br>(369.8) |
| YYB29 | 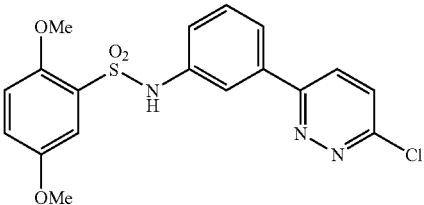<br>(405.86) |
| YYB30 | 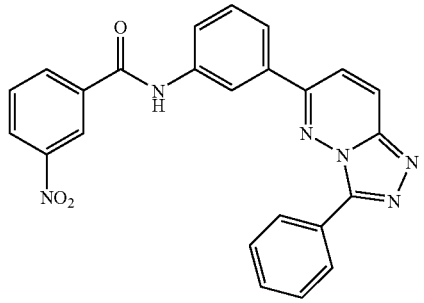<br>(436.42) |
| YYB31 | 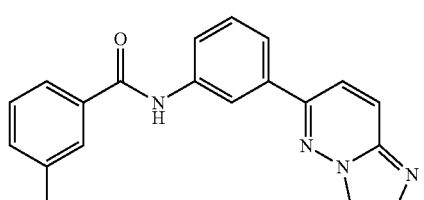<br>(360.33) |

TABLE A-continued
| Name of the Compound | Structure and M.F. and Molecular Weight |
|---|---|
| YYB32 | 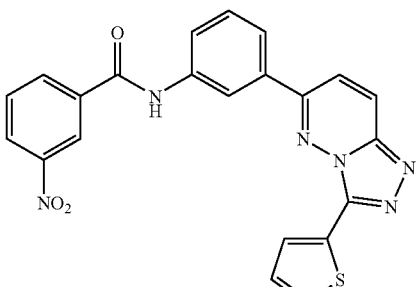<br>(442.45) |
| YYB33 | 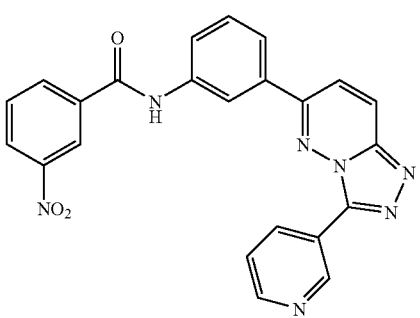<br>(437.41) |
| YYB34 | 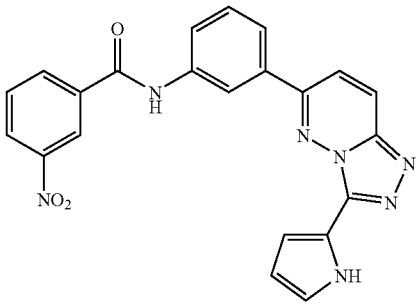<br>(425.4) |
| YYB36 | 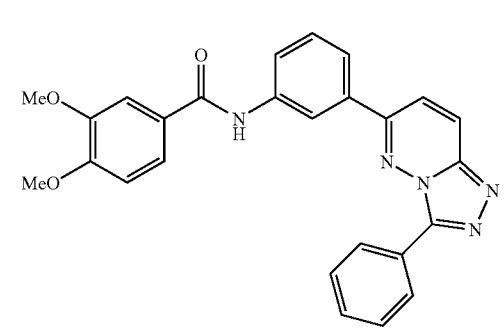<br>(451.48) |

TABLE A-continued
| Name of the Compound | Structure and M.F. and Molecular Weight |
|---|---|
| YYB37 | 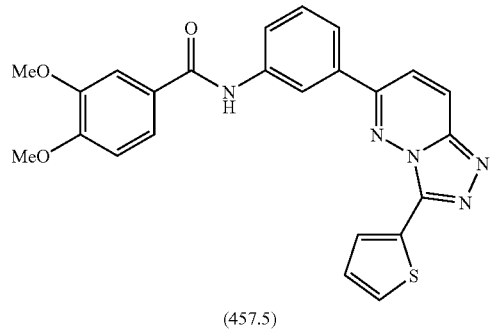<br>(457.5) |
| YYB38 | 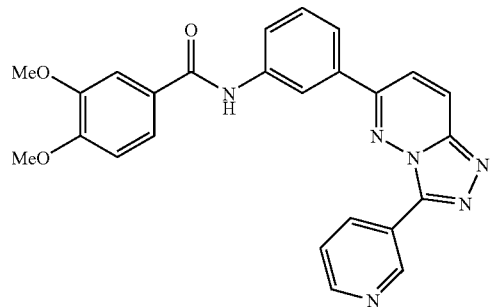<br>(452.46) |
| YYB39 | 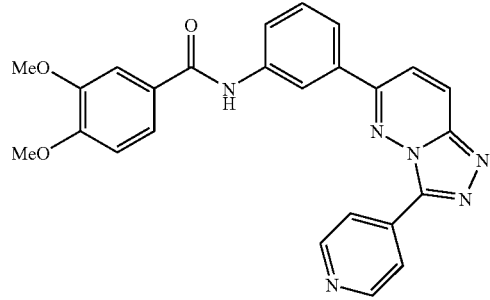<br>(452.46) |
| YYB40 | 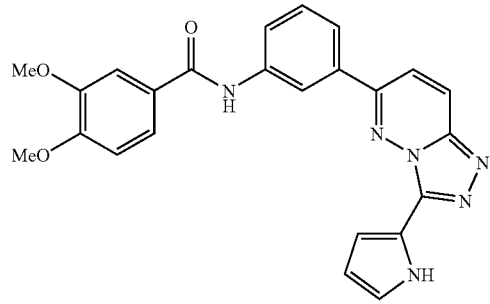<br>(440.45) |

TABLE A-continued
| Name of the Compound | Structure and M.F. and Molecular Weight |
|---|---|
| YYB41 | 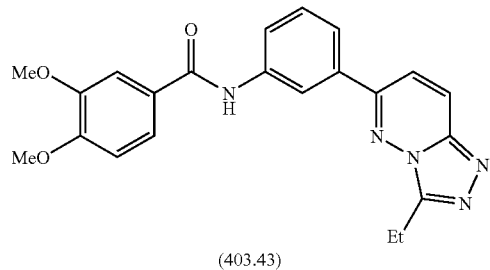<br>(403.43) |
| YYB42 | 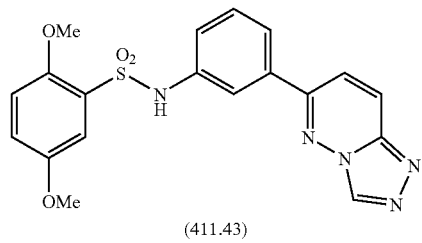<br>(411.43) |
| YYB44 | 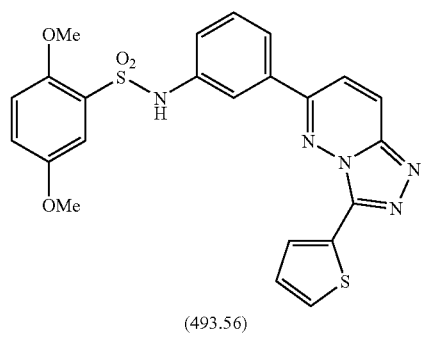<br>(493.56) |
Liwei Guo
| | |
|---|---|
| LG2-9 | 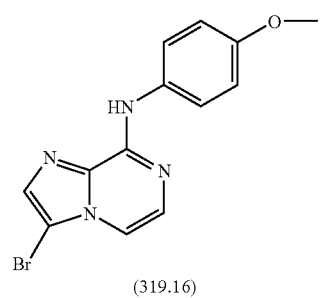<br>(319.16) |

TABLE A-continued
| Name of the Compound | Structure and M.F. and Molecular Weight |
|---|---|
| LG2-7 | 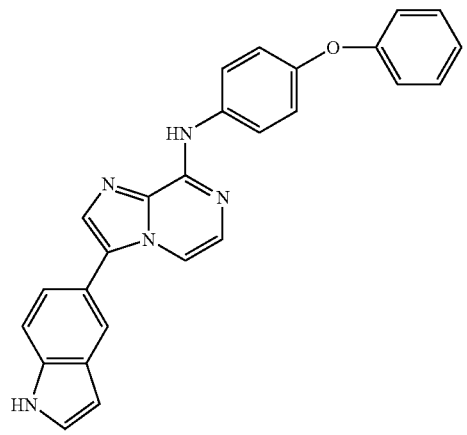 (417.46) |
| LG2-11 | 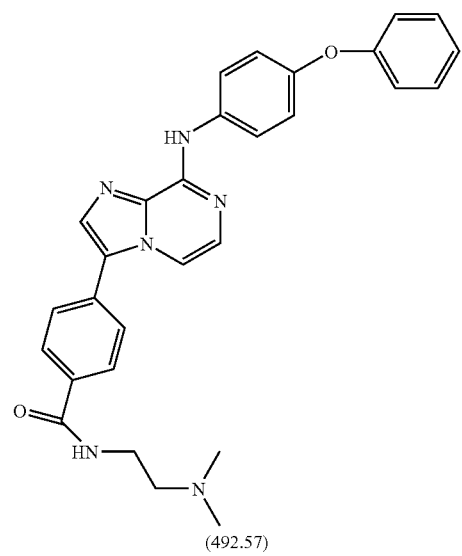 (492.57) |
| LG2-13 | 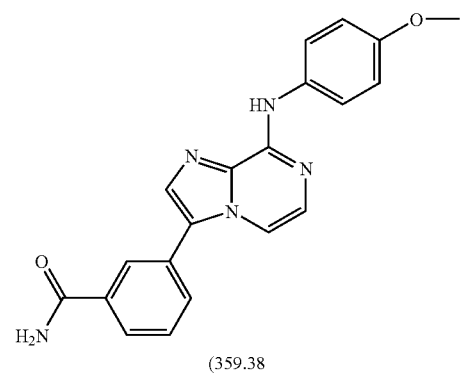 (359.38 |

TABLE A-continued

| Name of the Compound | Structure and M.F. and Molecular Weight |
|---|---|
| LG2-73 | (379.21) |
| LG2-87 | (328.17) |
| LG2-60 | (331.21) |
| LG2-55 | (289.13) |

US 8,268,809 B2
TABLE A-continued
| Name of the Compound | Structure and M.F. and Molecular Weight |
|---|---|
| LG2-77 | 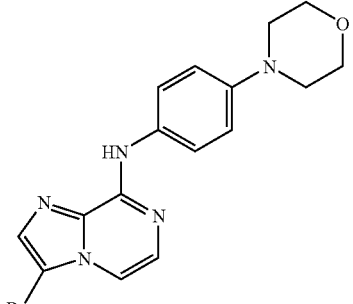<br>(374.24) |
| LG2-65 | 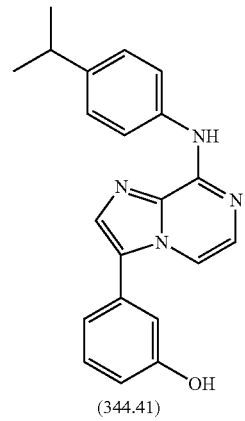<br>(344.41) |
| LG2-75 | 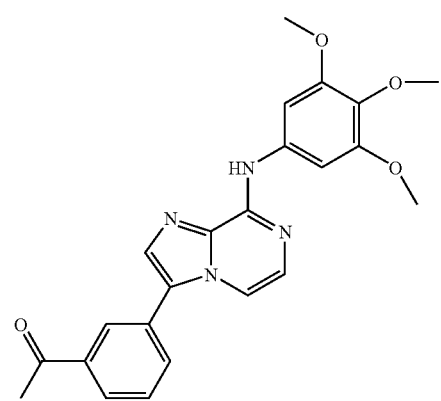<br>(418.45) |
| LG2-62 | 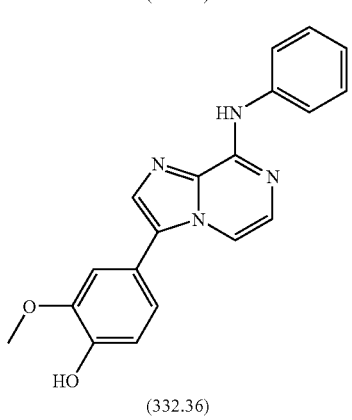<br>(332.36) |

TABLE A-continued
| Name of the Compound | Structure and M.F. and Molecular Weight |
|---|---|
| LG2-81 | 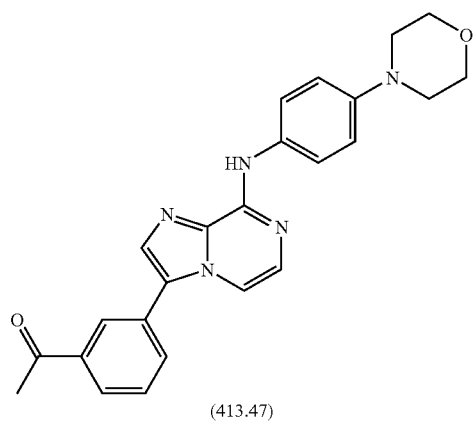<br>(413.47) |
| LG2-89 | 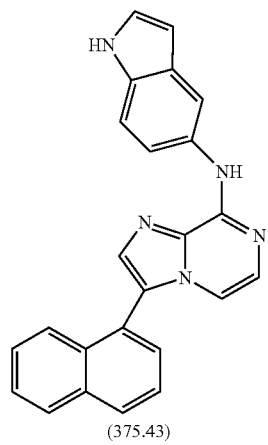<br>(375.43) |
| LG2-85 | 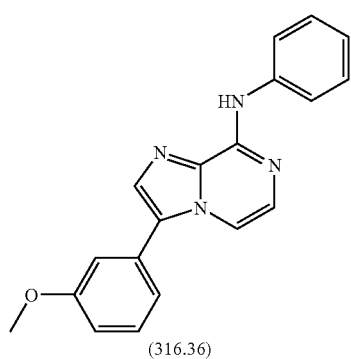<br>(316.36) |
| LG2-111 | 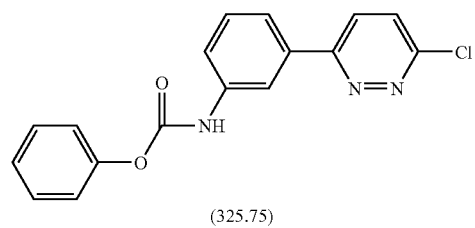<br>(325.75) |

TABLE A-continued
| Name of the Compound | Structure and M.F. and Molecular Weight |
|---|---|
| LG2-71 | 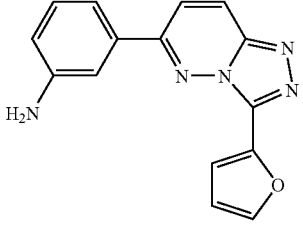<br>(277.28) |
| LG2-53 | 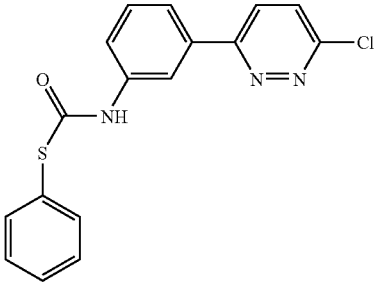<br>(341.82) |
| LG2-79 | 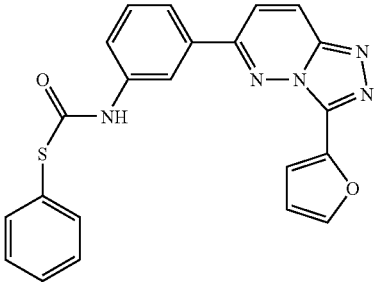<br>(413.45) |
| LG2-95 | 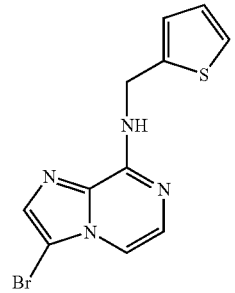<br>(309.19) |
| LG2-91 | 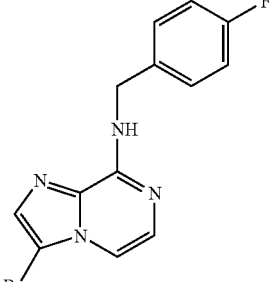<br>(321.15) |

TABLE A-continued
| Name of the Compound | Structure and M.F. and Molecular Weight |
|---|---|
| LG2-101 | 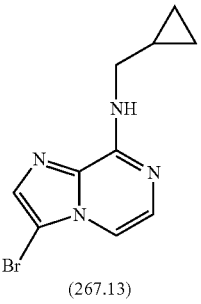<br>(267.13) |
| LG2-102 | 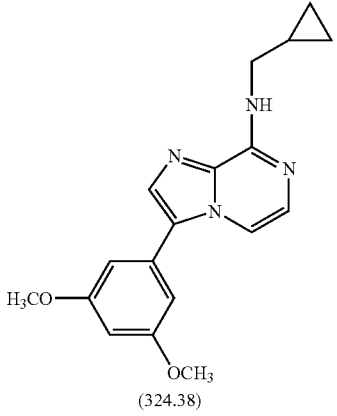<br>(324.38) |
| LG2-98 | 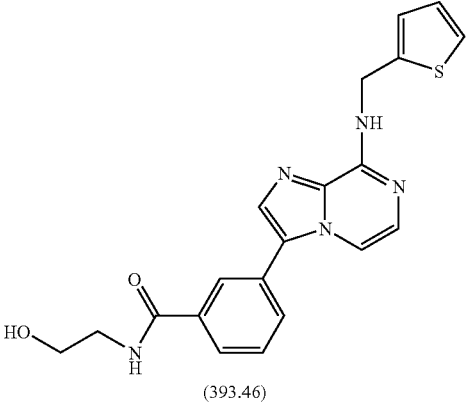<br>(393.46) |
| LG2-96 | 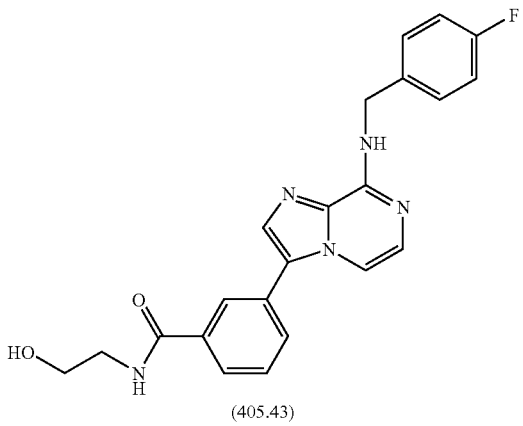<br>(405.43) |

TABLE A-continued
| Name of the Compound | Structure and M.F. and Molecular Weight |
|---|---|
| LG1-93 | 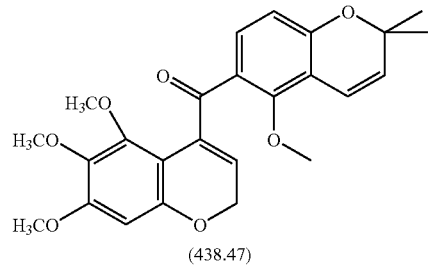<br>(438.47) |
| LG1-99 | 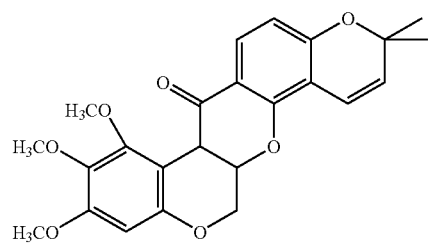<br>(424.44) |
| LG1-96 | 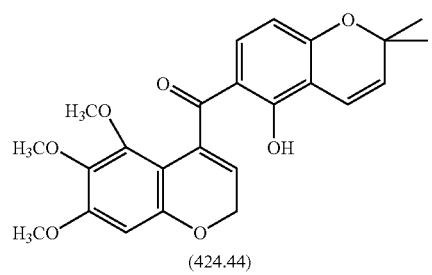<br>(424.44) |
| LG1-47 | 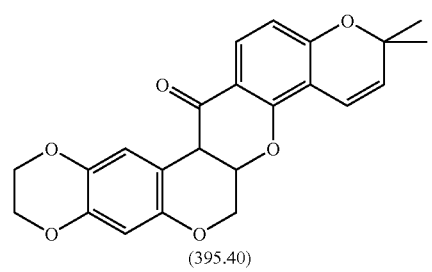<br>(395.40) |
| LG1-41 | 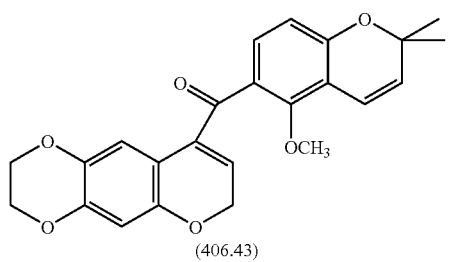<br>(406.43) |

TABLE A-continued
| Name of the Compound | Structure and M.F. and Molecular Weight |
|---|---|
| LG1-13 | 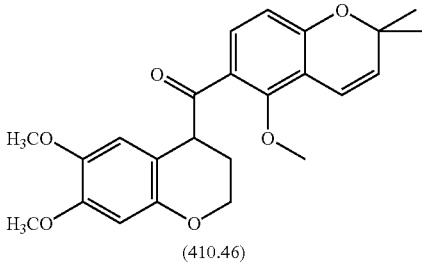 (410.46) |
| LG1-10 | 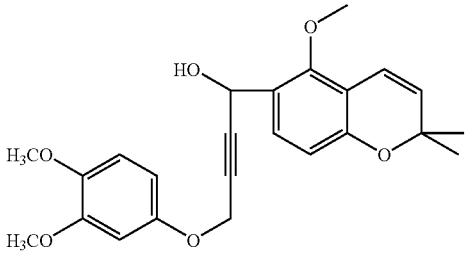 (410.46) |
| LG1-46 | 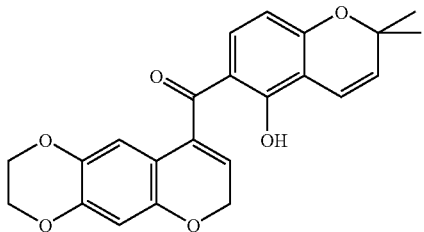 (392.40) |
| LG1-47 | 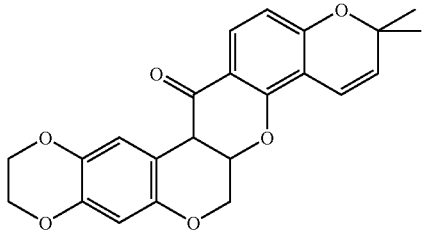 (392.40) |
| LG1-63 | 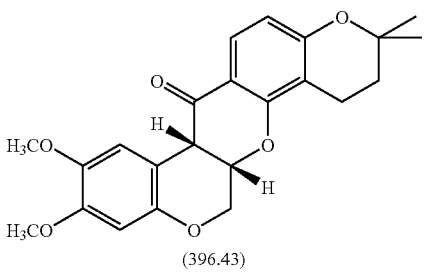 (396.43) |

TABLE A-continued

| Name of the Compound | Structure and M.F. and Molecular Weight |
|---|---|
| (−)-deguelin | (394.42) |
| LG1-68 | (392.44) |
| LG1-17 | (392.44) |
| LG1-36 | (408.44) |
| LG1-29 | (416.51) |

TABLE A-continued

| Name of the Compound | Structure and M.F. and Molecular Weight |
|---|---|
| LG1-28A | 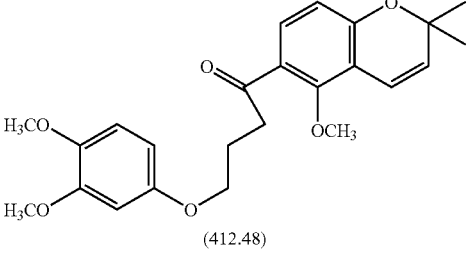<br>(412.48) |
| LG1-48 | 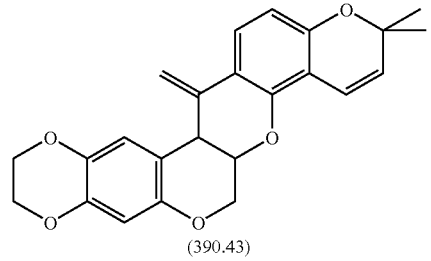<br>(390.43) |
| CR-4 | 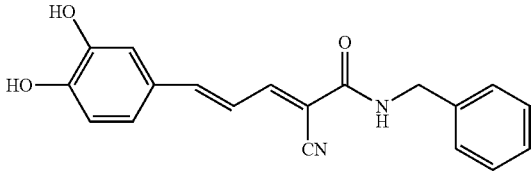<br>(320.34) |
| LG2-115 | 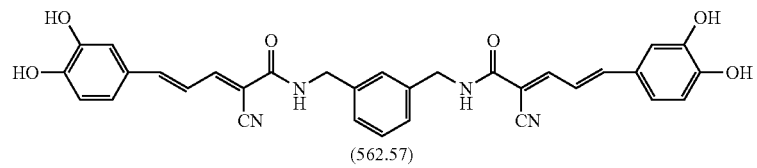<br>(562.57) |

One type of the kinase inhibitors listed above are inhibitors for tyrosine kinase that are involved in pathogen-host cell interactions associated with or cause pathogenic infection. It has been reported that diverse pathogens activate tyrosine kinases, particularly members of the Abl- and Src-families. Because Abl- and Src-family kinases are essential for the host, therapeutics must be dosed properly to minimize spread of the pathogen without harming the host. Because of the diverse numbers of pathogens that use Abl- and Src-family kinases (Reeves et al., 2005, Nat. Med. 11: 731-738), the development of "pan-therapeutics" that affect multiple pathogens is possible. Administration of tyrosine kinase inhibitors does not appear to interfere with acquisition of protective immunity (e.g. to poxviruses). Thus administration of therapeutics need continue only until an effective immune response has been mounted. Toxicity data from some tyrosine kinase inhibitors in cancer patients suggest that acute infections, where therapeutics could be administered for short periods of time (e.g. less than three weeks), would be ideal targets (Kerkela et al., 2006, Nat. Med. 12(8):908-16).

Diverse pathogens use kinases in a redundant fashion. Rather than utilize a single kinase pathway, pathogens appear to have developed molecular means to utilize several kinases within different subfamilies, perhaps as a means to increase their host range. Redundancy adds an element of complexity to the development of therapeutics. Because kinases that diverse pathogens utilize are dysregulated in a variety of human cancers, considerable effort has been made over the last two decades in developing compounds that inhibit these kinase activities. An inhibitor must be sufficiently non-specific to inhibit the class of kinases used by the pathogen, but within limits. Current efforts are also directed at identification of microbial and host molecules phosphorylated by kinases. Such molecules are also effective as therapeutic targets. It has also been found that some anti-cancer drugs have proven effective against a variety of pathogens (Reeves et al., 2005, Nat. Med. 11: 731-738).

The present invention further provides the use of the compositions comprising the compounds of the present invention to inhibit kinases involved in pathogen-host cell interactions that are associated with or cause pathogenic infection. In particular, the present invention provides the use of these kinase inhibitors to treat or prevent diseases associated with infection from microbial pathogens, including bacterial and viral pathogens such as *Escherichia coli* (enteropathogenic *Escherichia coli* (EPEC), enterohemorrhagic *Escherichia coli* (EHEC), uropathogenic *Escherichia coli* (UPEC), and enteroinvasive *Escherichia coli* (EIEC)), *Mycobacterium tuberculosis* (mTB), *Pseudomonas aeruginosa, Chlamydia trachomatis*, Pox viruses (including Vaccinia and variola viruses), polyoma viruses (including JC and BK viruses), human immunodeficiency viruses (for example, HIV-1), Herpes viruses (including Herpes Simplex virus, Epstein Barr virus, and Gamma Herpes virus), influenza virus, *Shigella flexneri*, Coxsackie virus, *Helicobacter pylori*, West Nile virus, *Listeria monocytogenes*, *Salmonella typhimurium*, cytomegalovirus (CMV), and other pathogens that are described in the literature. Particularly, these kinase inhibitors for use in the present invention include compounds listed in Table A above, or pharmaceutically acceptable salts, enantiomers, analogs, esters, amides, prodrugs, metabolites, or derivatives thereof.

The kinase inhibitors described herein can be used in the methods of the invention to treat or prevent any pathogenic infection that is associated with or caused by these kinase-mediated host-pathogen interactions, particularly microbial infection, and more particularly viral and bacterial infection. Without being bound by theory, it is believed that the kinase inhibitors described herein target host cell proteins and interfere with cellular mechanisms required for pathogenesis of the host cells by pathogens and in so doing prevent the pathogenic effects. Because cellular mechanisms regulating pathogen-host interactions are remarkably conserved, it is believed that the kinase inhibitors described herein can be applied to combat infection by a wide range of pathogens. Such pathogens include various microbes such as bacteria, protozoa, viruses, algae, and fungi. In a preferred embodiment of the present invention, the pathogens are bacteria and viruses. Advantageously, the therapeutic approach described herein targets the host, rather than the pathogen as is seen with antibiotics, and therefore decreases the likelihood of the development of pathogen drug resistance.

In one embodiment, the present invention provides the use of kinase inhibitors of the present invention to treat or prevent bacterial infections. Such infections include those caused by members of the following genera and species: *Agrobacterium tumefaciens, Aquaspirillum, Bacillus, Bacteroides, Bordetella pertussis, Borrelia burgdorferi, Brucella, Burkholderia, Campylobacter, Chlamydia, Clostridium, Corynebacterium diphtheriae, Coxiella burnetii, Deinococcus radiodurans, Enterococcus, Escherichia, Francisella tularensis, Geobacillus, Haemophilus influenzae, Helicobacter pylori, Lactobacillus, Listeria monocytogenes, Mycobacterium, Mycoplasma, Neisseria meningitidis, Pseudomonas, Rickettsia, Salmonella, Shigella, Staphylococcus, Streptococcus, Streptomyces coelicolor, Vibrio,* and *Yersinia*. In a preferred embodiment, such infections include those caused by *Escherichia coli, Helicobacter pylori, Listeria monocytogenes, Salmonella typhimurium, Shigella flexneri,* and *Mycobacterium tuberculosis* (TB). In an other embodiment, such infections include those caused by pathogenic and/or diarrheagenic *Escherichia coli* strains, including enteropathogenic *Escherichia coli* (EPEC), enterohemorrhagic *Escherichia coli* (EHEC), uropathogenic *Escherichia coli* (UPEC), and enteroinvasive *Escherichia coli* (EIEC).

In another embodiment, the present invention provides the use of kinase inhibitors of the present invention to treat or prevent viral infections. Such infections include those caused by members of the following virus families: Adenoviridae, Arenaviridae, Astroviridae, Bacteriophages, Baculoviridae, Bunyaviridae, Caliciviridae, Coronaviridae, Deltavirus, Filoviridae, Flaviviridae, Geminiviridae, Hepadnaviridae, Herpesviridae, Nodaviridae, Orthomyxoviridae, Papovaviridae, Paramyxoviridae, Parvoviridae, Phycodnaviridae, Picornaviridae, Poxyiridae, Reoviridae, Retroviridae, Rhabdoviridae, Tobamoviridae, and Togaviridae. In a preferred embodiment, such infections include those caused by Pox viruses including Vaccinia and variola viruses, polyoma viruses including JC and BK viruses, Herpes viruses, cytomegalovirus (CMV), and human immunodeficiency viruses (for example, HIV-1).

In accordance with the methods of the present invention, the kinase inhibitors of the present invention described herein may be administered in combination with one another, or with other compounds, particularly antipathogenic compounds. Such antipathogenic compounds include conventional antimicrobials. In other embodiments, one or more of the kinase inhibitors of the present invention described herein can be used in combination with other compounds such as cidofovir, for example, in cases related to smallpox, wherein the combination of these agents would provide for lower dosages of cidofovir to be administered, thereby decreasing the toxicity effects of this nucleoside analogue antiviral compound. Where the kinase inhibitors of the present invention are administered as part of a combination therapy to treat or prevent pathogenic infection, they may be administered concurrently or sequentially, in either order, with the additional compound(s).

In one embodiment, kinase inhibitors are administered to make vaccines more effective. For example, it is well known that immunization of neonates with live viruses does not contribute to acquired immunity because maternal antibodies neutralize the vaccine (Bot and Bona (2002) Microbes Infect. 4: 511). In one embodiment, administration of a kinase inhibitor of the present invention allows for safe administration of higher doses of virus to overcome antibody response and permit acquisition of cellular immunity. In another embodiment, kinase inhibitors of the present invention facilitate immune clearance of the pathogen. For some chronic viruses (e.g., HIV and polyoma), high viral loads have been found to compromise T cell function (Welsh (2001) J. Exp. Med. 193:F19). Thus, lowering the viral burden could permit recovery of T cell function and thereby facilitate clearance. In another embodiment, kinase inhibitors of the present invention permit immunocompromised individuals to be vaccinated.

The kinase inhibitors of the present invention are for administration in a living subject or patient, including a human being or an animal such as a laboratory monkey or mouse. It is to be understood that the present invention encompasses the use not only of the specific compounds described above, but also any pharmaceutically acceptable salts, enantiomers, analogs, esters, amides, prodrugs, metabolites, or derivatives thereof. Because some of the kinase inhibitors of the present invention are already the subject of drug development or are in use to treat certain cancers, data has established that they are well tolerated in humans even for extended periods (months), and are not toxic. The drugs can be ingested orally, are stable at room temperature, and are simple and inexpensive to manufacture.

In one embodiment of the present invention, a method of treating or preventing pathogenic infection, particularly microbial infection, comprises administering to a living subject in need of such treatment an effective amount of a pharmaceutical composition suitable for administration to the living subject where the pharmaceutical composition comprises: (a) at least one kinase inhibitor of the present invention in an amount effective for augmenting an inhibitable response from a host cell of the living subject responsive to at least one pathogen, particularly a microbe; and (b) a pharmaceutically acceptable carrier suitable for administration to the living subject. In another embodiment, the present invention provides pharmaceutical compositions suitable for administration to a living subject, comprising: (a) at least one kinase inhibitor in an amount effective for augmenting an inhibitable response from a host cell of the living subject responsive to at least one bacteria; and (b) a pharmaceutically acceptable carrier suitable for administration to a living subject. In another embodiment, the present invention provides pharmaceutical compositions suitable for administration to a living subject, comprising: (a) at least one kinase inhibitor in an amount effective for augmenting an inhibitable response from a host cell of the living subject responsive to at least one virus; and (b) a pharmaceutically acceptable carrier suitable for administration to a living subject. In yet another preferred embodiment, the kinase inhibitors of the present invention are tyrosine kinase inhibitors, preferably, the Abl- and/or Src-family tyrosine kinase inhibitors.

Depending upon the pathogenic infection to be treated or prevented, the pharmaceutical composition comprising a kinase inhibitor of the present invention described herein can be administered by any suitable route, including, but not limited to, orally, nasally, buccally, sublingually, intravenously, transmucosally, rectally, topically, transdermally, subcutaneously, by inhalation, or intrathecally administration.

In one of the preferred embodiments, these pharmaceutical compositions may be in the form of orally administrable suspensions, drinking solutions, or tablets; nasal sprays or nasal drops; or oleaginous suspensions or suppositories. When administered orally as a suspension, compositions of the present invention are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art. Components in the formulation of a mouthwash or rinse include antimicrobials, surfactants, cosurfactants, oils, water and other additives such as sweeteners/flavoring agents known in the art. When administered by a dribbling solution, the composition comprises one or more of the kinase inhibitors of the present invention described herein dissolved in drinking liquid such as water, with appropriate pH adjustment, and with carrier. The compound dissolved in the drinking liquid is an amount sufficient to give a concentration in the bloodstream on the order of 1 nM and above, preferably in an effective amount that is effective in vivo.

When administered nasally, these compositions are prepared according to techniques well known in the art of pharmaceutical formulation and may be prepared as solutions in saline, employing benzyl alcohol or other suitable preservatives, absorption promoters to enhance bioavailability, and/or other solubilizing or dispersing agents known in the art (see, for example, Ansel et al. (1999) Pharmaceutical Dosage Forms and Drug Delivery Systems (7th ed.). Preferably these compositions and formulations are prepared with suitable nontoxic pharmaceutically acceptable ingredients. These ingredients are known to those skilled in the preparation of nasal dosage forms and some of these can be found in Remington's Pharmaceutical Sciences (18th ed., Mack Publishing Company, Eaton, Pa.; 1990), a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present.

The formulations for the kinase inhibitors of the present invention may be varied to include: (1) other acids and bases to adjust the pH, (2) other tonicity-imparting agents such as sorbitol, glycerin, and dextrose; (3) other antimicrobial preservatives such as other parahydroxy benzoic acid esters, sorbate, benzoate, propionate, chlorbutanol, phenylethyl alcohol, benzalkonium chloride, and mercurials; (4) other viscosity imparting agents such as sodium carboxymethylcellulose, microcrystalline cellulose, polyvinylpyrrolidone, polyvinyl alcohol and other gums; (5) suitable absorption enhancers; (6) stabilizing agents such as antioxidants, like bisulfate and ascorbate, metal chelating agents such as sodium edentate, and drug solubility enhancers such as polyethylene glycols.

The above nasal formulations can be administered as drops, sprays, or by any other intranasal dosage form. Optionally, the delivery system can be a unit dose delivery system. The volume of solution or suspension delivered per dose can be anywhere from 5 to 500 microliters, and preferably 5 to 200 microliters. Delivery systems for these various dosage forms can be dropper bottles, plastic squeeze units, atomizers, and the like in either unit dose or multiple dose packages. Lozenges can be prepared according to U.S. Pat. No. 3,439,089, herein incorporated by reference for these purposes.

When rectally administered in the form of suppositories, these compositions may be prepared by mixing the kinase inhibitors of the present invention with a suitable non-irritating excipient, such as cocoa butter, synthetic glyceride esters, or polyethylene glycols, which are solid at ordinary temperatures, but liquify and/or dissolve in the rectal cavity to release the drug.

Dosage levels on the order of 1 mg/day or above may be useful in the treatment or prevention of pathogenic infections and related diseases within a host organism as noted herein above. In one embodiment of the present invention, a patient in need of treatment or prevention of pathogenic infection is administered a pharmaceutical composition comprising one or more kinase inhibitors of the present invention described herein in an effective amount of about 1 mg/day to about 1000 mg/day, for a patient having approximately 70 kg body weight. It will be understood, however, that the specific dose level and frequency of dosage for any particular patient may be varied and will depend upon a variety of factors including the activity of the specific salt or other form employed, the metabolic stability and length of action of that compound, the age, body weight, general health, sex, diet, mode and time of administration, rate of excretion, drug combination, the severity of the particular condition, and the host undergoing therapy. In one preferred regimen, such dosages can be administered to a subject in need thereof by either nasal spray or by oral lozenge.

The effectiveness of using the pharmaceutical compositions of the present invention to treat or prevent a specific pathogenic infection, particularly microbial infection, may vary, for example, depending on the infectious agent, stage of infection, severity of infection, age, weight, and sex of the patient, and the like.

As used herein, the term "treatment" is defined as the application or administration of one or more kinase inhibitors of the present invention described herein to a subject, where the subject has a pathogenic infection as noted elsewhere herein, a symptom associated with a pathogenic infection, or a predisposition toward development of a pathogenic infection, where the purpose is to cure, heal, alleviate, relieve, alter, remedy, ameliorate, improve, or affect the pathogenic infection, any associated symptoms of the pathogenic infection, or the predisposition toward the development of the pathogenic infection. The term "treatment" is also defined as an intended application or administration of a pharmaceutical composition comprising one or more kinase inhibitors of the present invention described herein to a subject, where the subject has a pathogenic infection as noted elsewhere herein, a symptom associated with a pathogenic infection, or a predisposition toward development of a pathogenic infection, where the purpose is to cure, heal, alleviate, relieve, alter, remedy, ameliorate, improve, or affect the pathogenic infection, any associated symptoms of the pathogenic infection, or the predisposition toward the development of the pathogenic infection.

The kinase inhibitors, particularly the tyrosine kinase inhibitors, of the present invention described herein are useful in treating or preventing pathogenic infections as noted herein above. Treatment or prevention of pathogenic infection in the manner set forth herein is also useful for transplant patients, for example, kidney transplant patients, where emergence of pathogens, particularly polyoma viruses, for example, JC and BK, and pathogenic infection can diminish function of the transplanted organ. In like manner, HIV infection can destroy oligodendrocytes in the brain, leading to AIDS-related dementia. Thus, in addition to treating or preventing pathogenic infections as noted elsewhere herein, the kinase inhibitors, particularly the tyrosine kinase inhibitors, of the present invention described herein can be used to control secondary infection in HIV-positive and AIDS patients and in patients receiving transplants, for example, kidney transplants, and to control AIDS-related dementia. Further, the kinase inhibitors, particularly, the tyrosine kinase inhibitors, can be used prophylactically to prevent spread of infectious virions, for example, associated with Vaccinia infections, in immunocompromised individuals, including HIV-positive and AIDS patients and in patients receiving transplants.

The present invention provides the use of kinase inhibitors to treat or prevent microbal infections caused by bacterial and/or viral pathogens. One of the bacterial pathogens is pathogenic *E. coli*, including enteropathogenic *E. coli* (EPEC) and enterohemorrhagic *E. coli* (EHEC), which contaminates water and food supplies and causes infantile diarrhea. EPEC and EHEC are classified by NIAID as category B pathogens. In developing nations, EPEC causes sickness in some 20 million per year, killing 500,000 (Goosney et al. (2000) Annul Rev. Cell Dev. Biol., 16: 173). EHEC, causative agent of "raw hamburger disease," contaminates food and is associated with diarrhea and an often fatal consequence, hemolytic-uremic syndrome. EHEC possess two Shiga toxins, which cause the symptoms associated with hemolytic-uremic syndrome (Perna et al. (2001) Nature, 409(6819): 529-33).

EPEC, EHEC, and *Citrobacter* (C) *rodentium* (mouse EPEC) form actin-filled membrane protrusions or "pedestals" beneath themselves on the surface of epithelial cells (Knutton et al. (1989) Lancet 2: 218; McDaniel et al. (1997) Mol. Microbiol., 23: 399). Pedestals prevent phagocytosis, allow colonization of the host, and are required for subsequent development of disease (Goosney et al. (1999) Infect. Immun, 67: 490; Jerse et al. (1990) Proc. Natl. Acad. Sci. USA, 87: 7839). The mechanisms by which pedestals form have been extensively investigated (Kalman et al. (1999) Nat. Cell Biol., 1: 389). The development of both pedestals and diarrhea are critically dependent on the activation of a host tyrosine kinase beneath the bacterium, which phosphorylates a bacterial protein secreted into the host cell called Tir (Kenny et al. (1997) Cell, 91: 511; Kenny (1999) Mol. Microbiol., 31: 1229). Upon binding of the bacterial ligand intimin, a host signal transduction cascade is initiated that leads to pedestal formation.

The watershed event in EPEC pathogenesis is the phosphorylation of EPEC Tir (Kenny (1999) Mol. Microbiol., 31: 1229). Once phosphorylated, EPEC Tir facilitates recruitment and activation of host cell proteins, including Nck, N-WASP, and Arp2/3 complex, that initiate actin polymerization to construct and brace the pedestal (Kalman et al. (1999) Nat. Cell Biol., 1: 389; Lommel et al. (2001) EMBO Rep., 2: 850; Gruenheid et al. (2001) Nat. Cell Biol., 3: 85619; Rohatgi et al. (1999) Cell, 97: 221).

One of the viral pathogens described herein are vaccinia virus (VV) and variola viruses that are members of the Poxyiridae family that are 95% identical in sequence (Esposito et al. (1990) Poxviruses, in Fields Virology, D. M. Knipe, Editor, Raven Press: New York. p. 2336; Moss (1990) *Poxyiridae: The Viruses and Their Replication*, in *Fields Virology*, D. M. Knipe, Editor. Raven Press: New York. p. 2336). VV western reserve (WR) strain serves as a vaccinating agent for variola major, the cause of smallpox. VV and variola enter mammalian cells, establish extranuclear replication "factories," and produce enveloped virions (Moss (1990) Poxyiridae: The Viruses and Their Replication, in Fields Virology, D. M. Knipe, Editor. Raven Press: New York. p. 2336). These virions travel to the cell surface using microtubule motors and transit into apposing cells by polymerizing actin (Ploubidou et al. (2000) EMBO J., 19(15): p. 3932-44; Rietdorf et al. (2001) Nat. Cell Biol., 3(11): p. 992-1000; Ward and Moss (2001) J. Virol., 75(23): p. 11651-63; Ward and Moss (2001) J. Virol., 75(10): p. 4802-13; Cudmore et al. (1996) J; Cell Sci., 109 (Pt 7): p. 1739-47; Cudmore et al. (1997) Trends Microbiol., 5(4): p. 142-8). There virions polymerize actin to propel themselves through the host cell cytoplasm and towards the plasma membrane, where they exit the cell and enter apposing cells. Formation of actin "comets" is considered critical for vaccinia to spread from cell to cell. For actin-based motility, vaccinia relies on the recruitment of host cell molecules to the surface of the particle, including tyrosine kinases. Ultimately, the host cell undergoes cytolysis thereby releasing additional infectious particles.

Tyrosine and serine/threonine kinases are important for several aspects of viral infection. Actin-based motility depends on the activity of the host cell tyrosine kinases related to c-Src and Abl, and replication at least in part depends on a viral kinase, though the precise mechanism is less well understood (Frischknecht et al. (1999) Nature 401 (6756):926-929; Rempel et al. (1992) J. Virol. 66(7):4413-4426; Traktman et al. (1995) J; Virol. 69(10):6581-6587; Traktman et al. (1989) J. Biol. Chem. 264(36):21458-21461).

Upon entry of the pox virus into host cells, the virion moves to a juxtanuclear location where it replicates up to $10^4$ concatemeric genomes (Moss (1990) *Poxyiridae: The Viruses and Their Replication*, in *Fields Virology*, D. M. Knipe, Editor. Raven Press: New York, p. 2336). The concatemers ultimately form individual enveloped particles (called intracellular mature virions (IMVs), some of which are packaged in additional membranes to form intracellular enveloped virions (IEVs; Smith et al. (2003) Annul Rev. Microbiol., pp. 323-342). Cytolysis releases IMVs from the cell. Prior to cytolysis, however, IEVs travel towards the host cell periphery via a kinesin/microtubule transport system (Carter et al. (2003) J. Gen. Virol., pp. 2443-2458; Hollinshead et al. (2001) J. Cell Biol., pp. 389-402; Rietdorf et al. (2001) Nat. Cell Biol., pp. 992-1000; Ward and Moss (2001) J. Virol., pp., 11651-11663).

To exit the cell, the intracellular enveloped virus (IEV) particle fuses with the plasma membrane of the host cell to form a cell-associated enveloped virus (CEV), leaving behind one of its two outer membranes (Smith et al. (2003) Ann. Rev. Microbiol., pp., 323-342; Smith et al. (2002) J; Gen. Virol., pp. 2915-2931). CEVs either detach directly, or initiate actin polymerization to propel the particle on an actin-filled membrane protuberance towards an apposing cell and then detach (Smith et al. (2003) Ann. Rev. Microbiol., pp., 323-342). Actin motility depends on Abl and Src family kinases whereas detachment of CEVs to form extracellular enveloped virus (EEV) depends on Abl family kinases (Smith et al. (2003) Ann. Rev. Microbiol., pp., 323-342).

It is known that the protein encoded by the VV A36R gene (called A36R), located in the membrane surrounding the CEV, is required for actin polymerization; and virulence (Wolffe et al. (1998) Virology pp. 20-26; Parkinson and Smith (1994) Virology pp. 376-390). The watershed event in actin polymerization and cell-to-cell spread is the phosphorylation of A36R tyrosine residues by a host cell tyrosine kinase (Newsome et al. (2004) Science 306:124-128; Frischknecht et al. (1999) Nature 401(6756):926-929). There is a remarkable homology between the EPEC Tir protein described above and the VV protein A36R, therefore using similar but not identical host signaling factors as EPEC to polymerize actin and exit from the host cell (Frischknecht and Way (2001) Trends Cell Biol. 11(1):30-38).

Previous reports suggest that the mammalian tyrosine kinase c-Src localizes to virions (Frischknecht et al. (1999) Nature 401(6756):926-929). Moreover, the release of virions from microtubules and nucleation of actin to form actin tails depends on phosphorylation of A36R by Src or other kinases (Newsome et al. (2004) Science 306:124-128; Frischknecht et al. (1999) Nature 401(6756):926-929; Kalman et al. (1999) Nat. Cell. Bio. 1:389-391). Once phosphorylated, A36R facilitates detachment of kinesin and recruitment and activation of host cell proteins, including Nck, Grb2, N-WASP, and the Arp2/3 complex, which initiate actin polymerization beneath the particle (Frischknecht and Way (2001) Trends Cell Biol. 11(1):30-38; Moreau et al. (2000) Nat. Cell Biol., pp. 441-448; Scaplehorn et al. (2002) Curr. Biol., pp. 740 745). Indeed vaccinia uses mechanisms similar to those used by *Shigella flexneri* to propel itself through the host cytoplasm. For example, both *Shigella* and *Vaccinia* recruit and activate N-WASP and the Arp2/3 complex as a means of polymerizing actin (Frischknecht and Way (2001) Trends Cell Biol. 11(1):30-38).

These and many other variations and embodiments of the invention will be apparent to one of skill in the art upon a review of the appended description and examples.

EXAMPLES

Example 1

Drug Screening Using Microscopy Assays

The present invention provides drug screening assays for microbal pathogens. In one of the preferred embodiments, the present invention provides drug screening assays for viral pathogens, preferably, the poxviruses. Two exemplary drug screening assays: the microscopy assay and the Plaque Assay, are provided herein. The purpose of microscopy assays is to screen compounds in a high throughput format for their effects on the formation of actin protein filled membranous protrusions caused by vaccinia virus egressing from an infected cell (or "tails"). The microscopy assays also reveal, albeit indirectly effects on replication or viral maturation.

To do the microscopy assays, cultured 3T3 cells were added at a low density to collagen/PDL-coated glass microscopy slips or on 96 well optical tissue culture plates. The cells were allowed to adhere to these slips overnight. The next day, the media was removed from these cells and replaced with low-serum media. Approximately $10^6$ vaccinia virus virions were added directly to the low-serum media and infection was allowed to continue for 1 hour at 37° C. to permit adsorption of virus to the cells. After 1 hour, the compounds of the present inventions were added at a 1:10 dilution directly to the infected cells. Infection was allowed to continue for another 16 hours. After this period the media was removed and the cells fixed and stained. Actin protein was visualized with fluor-conjugated phalloidin and DNA (viral and cellular) was visualized by staining with DAPI, as described (see Reeves et al., 2005, Nat. Med. 11: 731-738). Cells were imaged on a multiwavelength fluorescence microscope for the presence of cytopathic effect, viral infection and actin protein tail formation.

Figure 3:
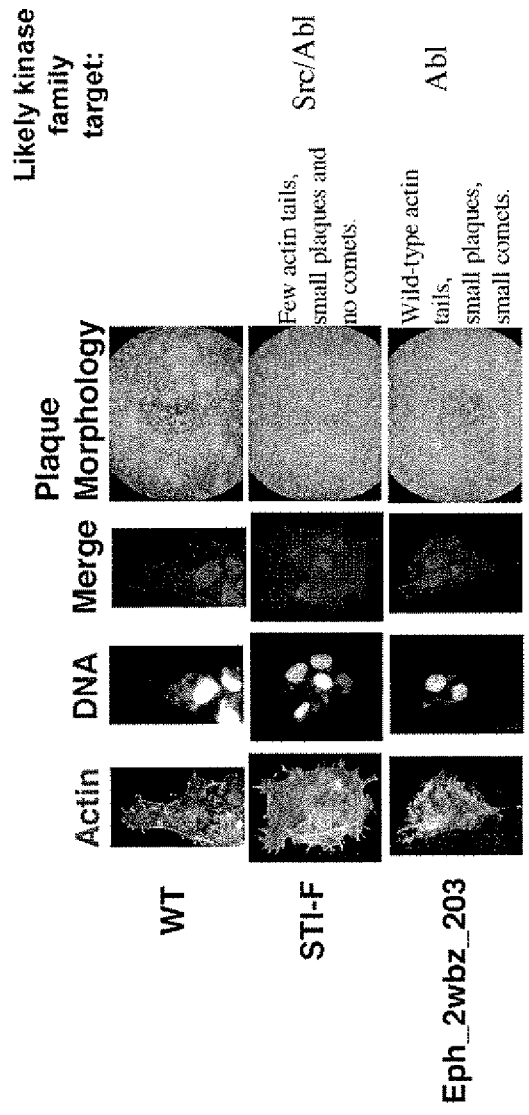
FIG. 3 illustrates actin protein tail and plaque formations from microscopy and plaque vaccinia assays for wild type (WT, with virus only) (top row) and with compounds STI-F (middle row) and Eph_2wbz_203 (bottom row), and their likely kinase family targets.

FIG. 3 illustrates actin protein tails from microscopy assays for wide type (WT, virus infection with no drug treatment) (top row) and with compounds STI-F (middle row) and Eph_2wbz_203 (bottom row), and their likely kinase family targets. The results presented that compound STI-F induced few actin tails, whereas compound Eph_2wbz_203 induced wild-type actin protein tails, suggesting that these compounds may target tyrosine kinase to inhibit viral infections.

Example 2

Drug Screening Using Plaque Assays

The purpose of the plaque assays is to screen compounds for their effect on vaccinia virus plaque size, and on the formation of "comet" plaques, an archipelago of smaller plaques that form adjacent to a large plaque. Large plaques form as virus from an infected cell egresses, by means of actin protein tails, and infects an apposing cell. An infected cell eventually dies leaving a hole in the monolayer. Comet plaques occur when a form of the virus (called EEV) is released into the supernatant and settles adjacent to a large plaque. Comets are generally smaller than large plaques because the initial infection is derived from virus produced by an adjacent large plaque, not by the initial inoculum. To a small extent, the size of the large plaques is determined by EEV as well. Formation of actin protein tails (and thus the size of large plaques) depends on Src- and Abl-family kinases (Reeves et al., 2005, Nature Medicine. 11: 731-738), whereas the formation of EEV (and hence comets) depends on Abl-family kinases. Inhibitors of Abl- and Src-family kinases result in "pinpoint" plaques (e.g. PD166326), whereas inhibitors of Abl-family kinases cause somewhat reduced plaque size and loss of comets (e.g. Gleevec® or STI-571). The Src and Abl family tyrosine kinases have been found to participate in vaccine virus (VV) action motility and release of infectious virions, and inhibitors of these tyrosine kinases block formation of action tails. See WO 2205/072826, the entire publication is incorporated by reference herein.

To do the plaque assay, cultured BSC40 cells were added to 12-well tissue culture dishes at a high density. These cells were allowed to adhere overnight and reach confluency. The media covering the monolayers was removed and replaced with low serum media (2% FBS). Approximately $1 \times 10^3$ PFU of vaccinia virus was added to the monolayers and allowed to adsorb to the cells for 1 hour. Following adsorption, the low serum media was removed and replaced with complete media (10% FBS). Compounds of the present invention were added to complete media for a final concentration of 100 μM. Monolayers were allowed to incubate for approximately 3 days at 37° C. undisturbed. After this period, the media is removed and cells are fixed and stained with a Crystal Violet solution, and scored for plaque size or the presence of comets.

Figure 2:
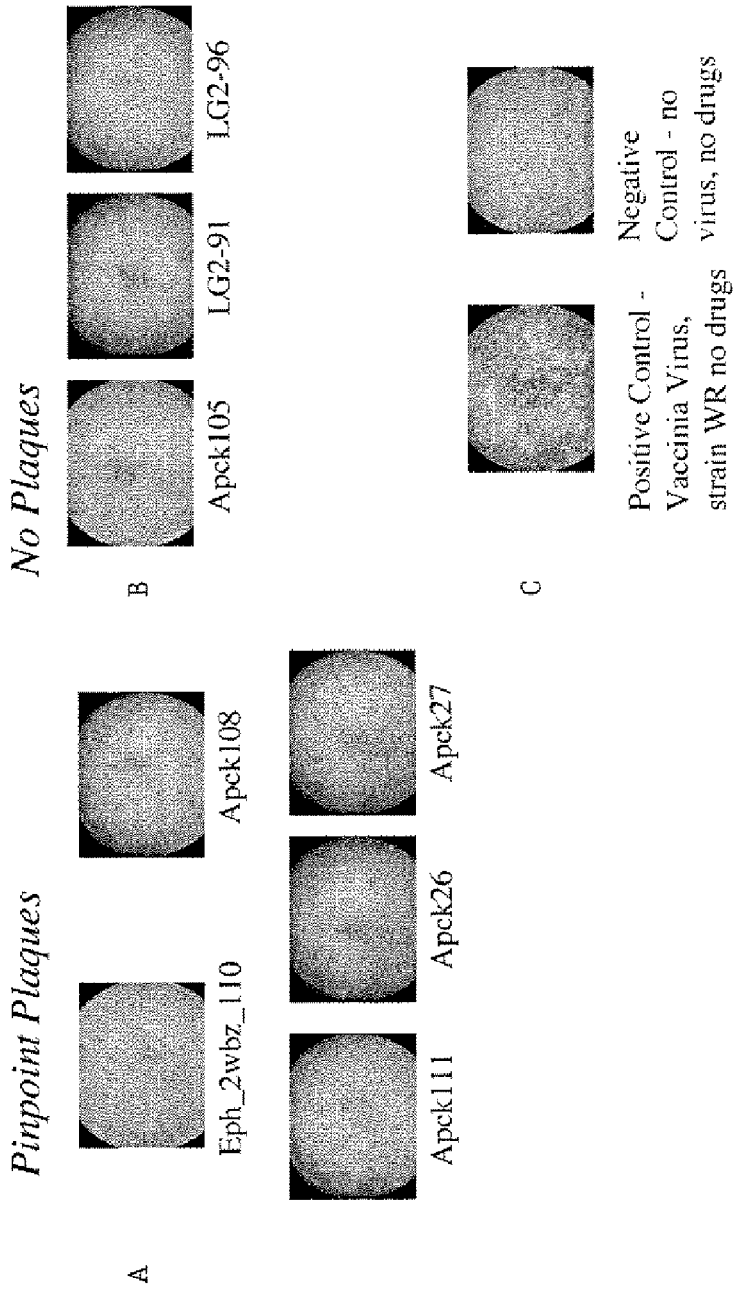
FIGS. 2A-C illustrate pinpoint plaque formations due to drug treatment in Plaque Assays.

Compounds as disclosed in Summary Table B (See Table B) have been identified that have activity against poxvirus and specifically vaccinia virus (VV) based on the plaque assays. For instance, FIG. 1 shows compounds Eph_2wbz_105, Eph_2wbz_203, Eph_2wbz_206 and LG2-71 produce small plaques with comets (FIG. 1B), whereas compounds DM-I-187 and DM-I-196 produce smaller (pinpoint) plaques with no comets (FIG. 1C). Compounds Eph_2wbz_110, Apck108, Apck111, Apck26, and Apck27 produce pinpoint plaques (FIG. 2A), whereas compounds Apck105, LG2-91 and LG2-96 produce no plaques (FIG. 2B). Moreover, FIG. 4 illustrates additional phenotypes: such as small plaques with large comets produced by compounds Apck34 and Apck32 (FIG. 4A); more plaques than WT were produced by treated with compounds JGAP-13 and Butyeolactones-1 (FIG. 4B); and damaged monolayer was produced by treated with compounds Apck101 and YYB21 (FIG. 4C).

Based on the results with inhibitors of Src- and Abl-family kinases, (e.g. PD166326 and BMS354825), we chose to score the infected monolayers for three categories: (Class I) no difference from untreated cells; (Class II) small plaques without evidence of comets, indicative of an inhibitor of Abl-family kinases and EEV release; and (Class III) pinpoint plaques or absence of plaques, and absence of comets, indicative of an inhibitor of Src- and Abl-family kinases, a block in actin tails and release of EEV. Compounds belong to Class II category include, but are not limited to Eph2_wbz 107; WBZ-4; Eph2-wbz206; Eph2-wbz 211; APcK-107; APcK109; APcK110; YYB41; YYB44; LG2-62; LG2-79; JAK2F (See Table B below). Compounds belong to Class III category include, but are not limited to Eph2_wbz 102; Eph2_wbz 103; Eph2_wbz 104; Eph2_wbz 105; Eph2_wbz 106; Eph2_wbz 110; Eph2-wbz 112; Eph2-wbz 117; STI-OH; STI-F; STLL3; StiAF3_Ue; STLF2; Eph2_wbz202; Eph2-wbz203; Eph2_wbz216, AS605091; AS604850; AS605240; APcK-102; APcK-103; APcK104; APcK-105; APcK-106; APcK108; APcK111; APcK-26; APcK27; APcK35; APcK40; APcK43; APcK44; APcK48; dm-1-187; dm-1-193; dm-1-196; dm-1-203; PD166326; PD-Br; YYA104; YYA188; YYA194; YYA195; YYB19; YYB31; YYB32; LG2-9; LG2-11; LG2-13; LG2-85; LG2-71; LG2-95; LG2-91; LG2-101; LG2-102; LG2-98; LG2-96 (See Table B below).

Some of the compounds tested herewith, e.g., ApCK103, Apck-43, LG2-55, and LG2-71 had effects in both the Herpes and Vaccinia assays (see also below, and Table B below). Others (e.g. PD166326 and related compounds described in previous applications) had effects in both vaccinia assays and assays with pathogenic *E. coli* (Swimm et al., 2004, Molecular Biology of the Cell. 2004. 15:3520-3529). Some of the Class II and III compounds were also tested in microscopy assays as described above. The results showed that Class II compounds tested in that assay did not affect the number of actin tails, whereas Class III compounds tested in that assay reduced or eliminated actin tails (See FIG. 3). As described above, FIG. 3 illustrates actin protein tail and plaque formations from microscopy and plaque vaccinia assays for wide type (WT, with only the vaccinia virus infection) (top row) and with compounds STI-F (middle row) and Eph_2wbz_203 (bottom row), and their likely kinase family targets.

Based on the characterization of the kinase-dependence of actin motility, these data indicate that Class II compounds likely inhibit Abl-family kinases and Class III compounds likely inhibit both Abl- and Src-family kinases, though there might be a possibility that other kinases are also inhibited.

The results provided herewith also provide implications for a treatment of poxyiral infections. Because the phenotypes caused by Gleevec®, an inhibitor used for the treatment of poxyiral infections, are consistent with the phenotypes caused by the Classes II and III compounds described herewith, it suggests that both Class II and Class III compounds will likely block EEV release. Because EEV mediate dissemination of the virus in vivo, these compounds will likely confine the infection to a particular locale (e.g. lungs). Furthermore, because Gleevec® does not interfere with the acquisition of protective immunity, immunosuppressive effects of the Class II or Class III compounds provided herewith would not be expected.

Example 3

Drug Screening Assays for Herpes Virus

All herpes viruses share the property of establishing life-long infection in their host. Notably, the gamma-herpes viruses are all associated with the development of lymphomas and other cancers. To determine whether tyrosine kinases participate in gamma-herpes virus infections, confluent monolayers of 3T3 cells were exposed and plated in optical 96 well dishes to the library of compounds of the present invention described herein for 1 hour. The cells were then infected with a gamma-herpes variant that expresses GFP under a CMV promoter (GHV-Bac-GFP), and replaced the compounds of the present invention at final concentration of 10 μM.

After 7 days, control cells that were left untreated exhibited marked cytopathic effects, an effect attributed to the spread of the initial infection throughout the monolayer, and subsequent lysis of infected cells. Amongst compound treated cells, three phenotypes were evident: (i) compound treated cells showed evidence of cytopathic effects to the same extent as controls. Because compound treated cells left uninfected showed little evidence of cytopathic effects this phenotype indicates that compounds causing this phenotype did not affect viral entry, egress from an infected cell, spread within the monolayer, or lysis; (ii) Monolayers of cells remained intact after treated with this group of compounds, and examination of the GFP fluorescence indicated foci of fluorescence that did not spread throughout the monolayer. This phenotype indicates that the compounds causing this phenotype likely block virus entry or egress. Exemplary compounds include, but are not limited to CGP-2 (Gleevec®), StiAF3-iAR, and LG2-71 compounds of the present invention (See Table B below); and (iii) Monolayers of cells also remained intact after treated with this group of compounds, but examination of the GFP fluorescence indicated fluorescence throughout the monolayer. This phenotype indicates that the compounds causing this phenotype did not block viral entry or egress but may inhibit cellular lysis. Exemplary compounds include, but are not limited to CGP51148WBZ-4, Apck103, Apck21, APck25, APcK36, ApcK 42, APCK50, APCK51, APCK53, LG2-55, LG2-77, and LG2-81 (See Table B below). Together these data suggest that compounds in groups (ii) and (iii) affect aspects of viral growth, and limit production of new virus, and are further expected to be useful for treating and preventing pathogenic infections.

Although these compounds provided herewith are designed to inhibit tyrosine kinases, there is no evidence in the literature for the involvement of tyrosine kinases in gamma Herpes pathogenesis, and off-site effects of these compounds on cellular or viral targets would not be ruled out. Nevertheless, the compounds identified herewith may prove effective in treating infections caused by Herpes virus and related virus, including, but not limited to Epstein Barr virus and Herpes Simplex virus.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not be limited to the specific embodiments disclosed and that modifications and other embodiments are intended to be included within the scope of the appended claims. Although specific terms are employed herein, they are used in a generic and descriptive sense only and not for purpose of limitation. Further, it must be noted that as used in this specification and the appended embodiments, the singular forms "a," "an," and "the" include plural references unless the context clearly dictates otherwise.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

TABLE B

| COM-POUND | STRUCTURE | VAC-CINIA Plaque Assay | VAC-CINIA PLAQUE ASSAY 2 | HERPES |
|---|---|---|---|---|
| Eph2_wbz 101 | 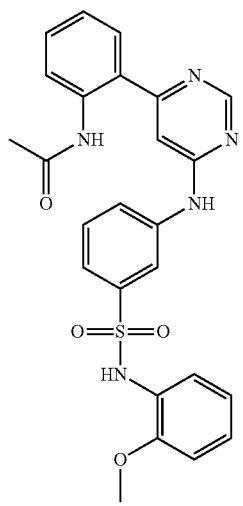 | WT | Not screened | WT |
| Eph2_wbz 102 | 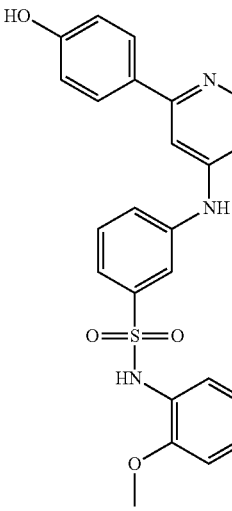 | NO PLAQUES | no plaques | WT |

TABLE B-continued
| COMPOUND | STRUCTURE | VACCINIA Plaque Assay | VACCINIA PLAQUE ASSAY 2 | HERPES |
|---|---|---|---|---|
| Eph2_wbz 103 | 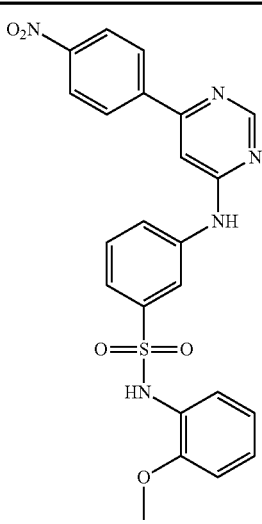 | NO PLAQUES | PINPOINT | WT |
| Eph2_wbz 104 | 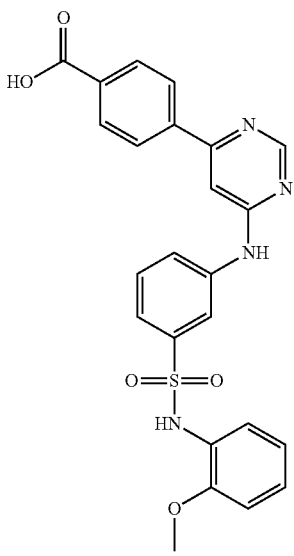 | NO PLAQUES | SLIGHTLY SMALLER PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| Eph2_wbz 105 | 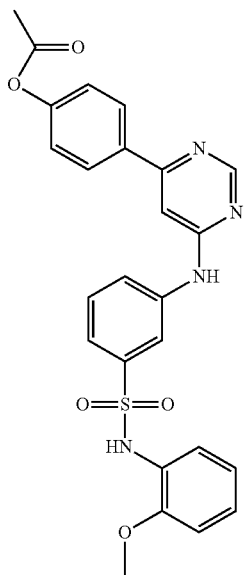 | SMALLER PLAQUES THAN WT | NO PLAQUES | WT |
| Eph2_wbz 106 | 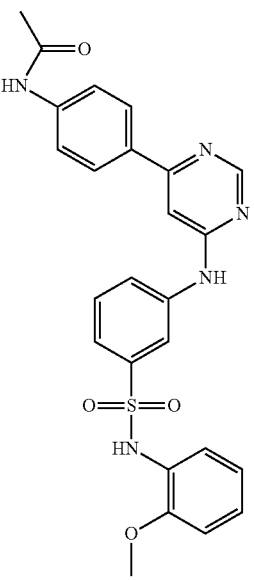 | NO PLAQUES | SMALLER PLAQUES THAN WT | WT |

TABLE B-continued

| COMPOUND | STRUCTURE | VACCINIA Plaque Assay | VACCINIA PLAQUE ASSAY 2 | HERPES |
|---|---|---|---|---|
| Eph2_wbz 107 | 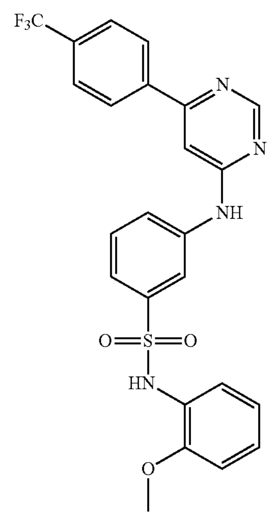 | SMALLER PLAQUES THAN WT | SMALLER PLAQUES THAN WT | WT |
| Eph2_wbz 110 | 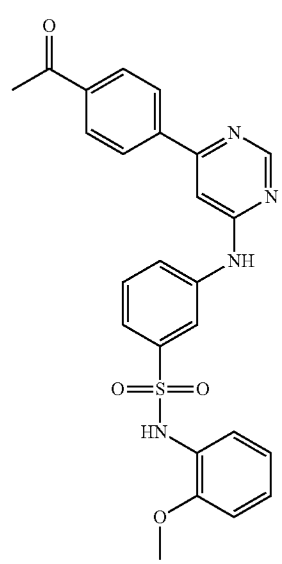 | PINPOINT PLAQUES | PINPOINT | WT |

TABLE B-continued
| COMPOUND | STRUCTURE | VACCINIA Plaque Assay | VACCINIA PLAQUE ASSAY 2 | HERPES |
|---|---|---|---|---|
| Eph2_wbz 112 | 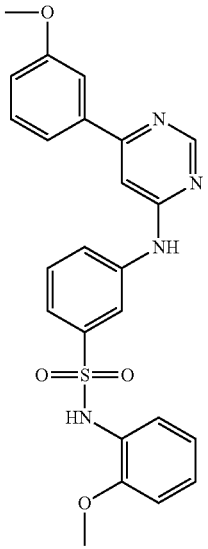 | SMALL PLAQUES | PINPOINT | WT |
| Eph2_wbz 115 | 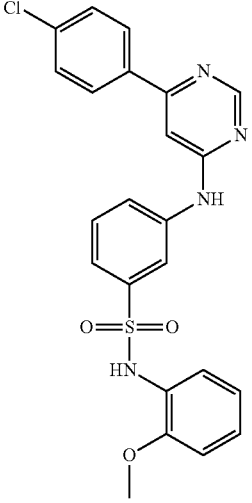 | WT | | DELAYED CPE |

TABLE B-continued

| COMPOUND | STRUCTURE | VACCINIA Plaque Assay | VACCINIA PLAQUE ASSAY 2 | HERPES |
|---|---|---|---|---|
| Eph2_wbz 116 | 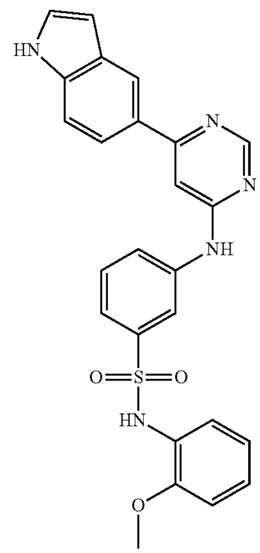 | CPE | | WT |
| Eph2_wbz 117 | 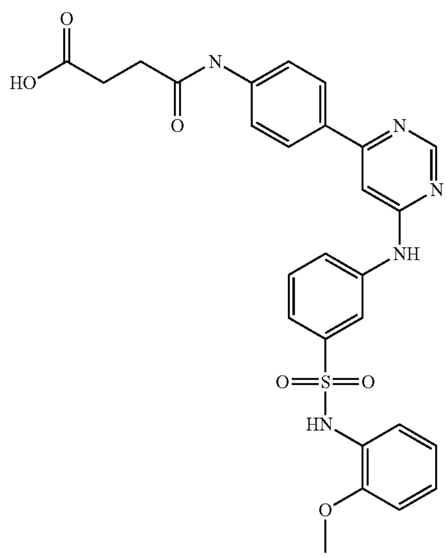 | NO PLAQUES | SMALL PLAQUES; COMETS? | WT |
| WBZ-6 | $C_{34}H_{34}N_8O$<br>Exact Mass: 570.29<br>Zhenghong Peng WBZ_6 | CPE | | DELAYED CPE |

TABLE B-continued

| COMPOUND | STRUCTURE | VACCINIA Plaque Assay | VACCINIA PLAQUE ASSAY 2 | HERPES |
|---|---|---|---|---|
| STI-OH | STI-OH<br>C$_{30}$H$_{33}$N$_7$O$_2$<br>Mol. Wt.: 523.63 | PINPOINT PLAQUES | SMALL PLAQUES | WT |
| STI-F | STI_F_1<br>C$_{35}$H$_{34}$FN$_7$O<br>Exact Mass: 587.28 | PINPOINT PLAQUES | NO PLAQUES | WT |
| STLL3 | STI_I_3<br>C$_{35}$H$_{34}$IN$_7$O<br>Exact Mass: 695.19 | PINPOINT PLAQUES | NO PLAQUES | WT |
| StiAF3-iAR | C$_{34}$H$_{34}$N$_8$O<br>Exact Mass: 570.29<br>Zhenghong Peng WBZ_6 | CPE | | ENTRY OR EGRESS INHIBITOR |

TABLE B-continued
| COMPOUND | STRUCTURE | VACCINIA Plaque Assay | VACCINIA PLAQUE ASSAY 2 | HERPES |
|---|---|---|---|---|
| StiAF3_Ue | 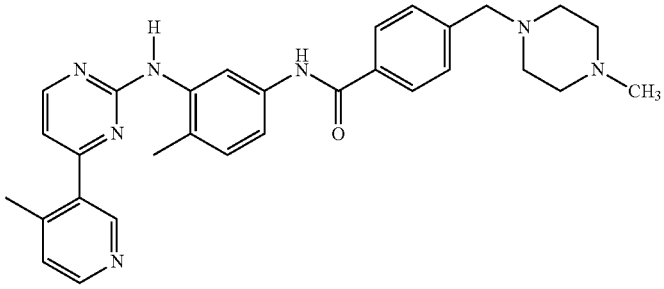<br>$C_{30}H_{33}N_7O$<br>Exact Mass: 507.27<br>WBZ1 Zhenghong Peng | NO PLAQUES | NO PLAQUES | WT |
| STLF2 | 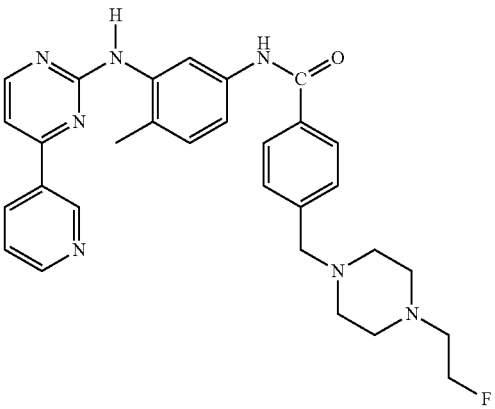<br>STI_F2<br>$C_{30}H_{32}FN_7O$<br>Mol. Wt.: 525.62<br>Zhenghong Peng | PIN POINT PLAQUES | NO PLAQUES | WT |
| WBZ-4 | 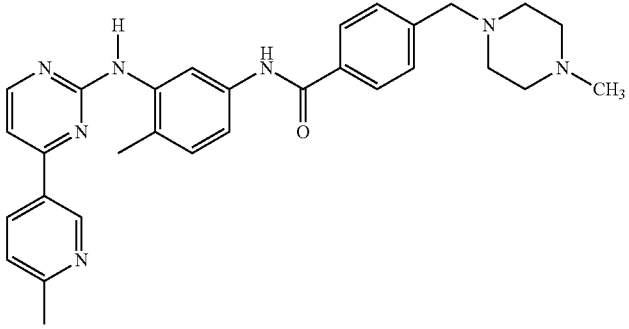<br>$C_{30}H_{33}N_7O$<br>Exact Mass: 507.27<br>Zhenghong Peng WBZ_4 | SMALL PLAQUES | SMALL PLAQUES | WT |

TABLE B-continued

| COMPOUND | STRUCTURE | VACCINIA Plaque Assay | VACCINIA PLAQUE ASSAY 2 | HERPES |
|---|---|---|---|---|
| Eph2_wbz 202 | 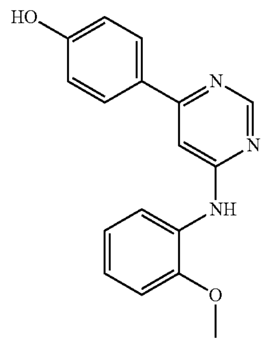 | PLAQUES SMALLER THAN WT, STILL SEE COMETS | PINPOINT PLAQUES | WT |
| Eph2_wbz 203 | 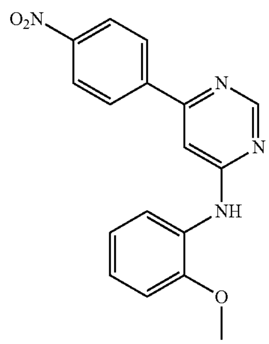 | SMALL PLAQUES, STILL SEE COMETS | SMALL PLAQUES | WT |
| Eph2_wbz 206 | 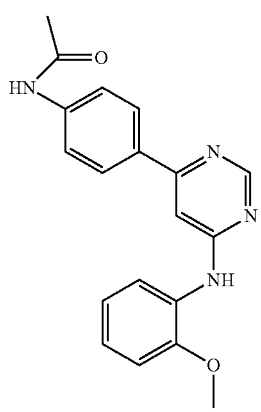 | SMALL PLAQUES, COMETS? | SMALL PLAQUES | WT |
| Eph2_wbz 211 | 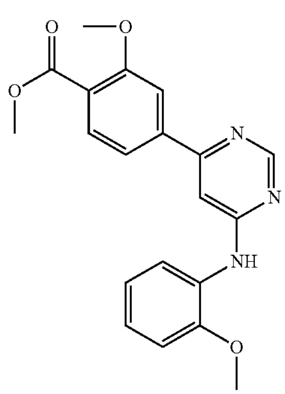 | SMALL PLAQUES Comets? | SLIGHTLY SMALLER PLAQUES | WT |

TABLE B-continued

| COMPOUND | STRUCTURE | VACCINIA Plaque Assay | VACCINIA PLAQUE ASSAY 2 | HERPES |
|---|---|---|---|---|
| Eph2_wbz 216 | 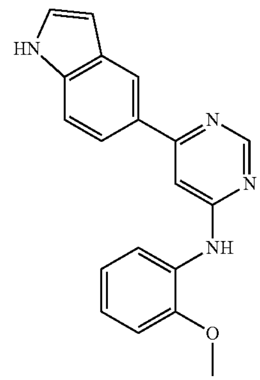 | SLIGHTLY SMALLER PLAQUES | NO PLAQUES | WT |
| Eph2_wbz 217 | 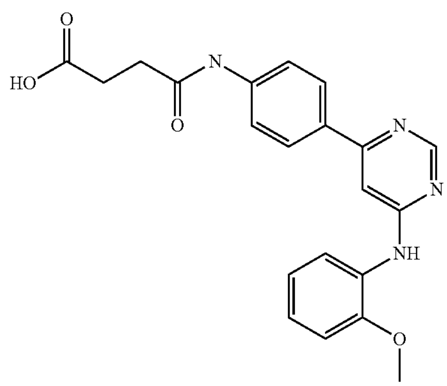 | SLIGHTLY SMALLER PLAQUES | WT | WT |
| AS-605091 | $C_{13}H_{12}N_2O_3S$<br>Exact Mass: 276.0569<br>Mol. Wt.: 276.311 | SMALL PLAQUES | PINPOINT PLAQUES | WT |
| AS-604850 | $C_{11}H_5F_2NO_4S$<br>Exact Mass: 284.9907<br>Mol. Wt.: 285.2235 | NO PLAQUES | NO PLAQUES | WT |
| AS-604240 | $C_{12}H_7N_3O_2S$<br>Exact Mass: 257.0259<br>Mol. Wt.: 257.2679 | PINPOINT PLAQUES | PINPOINT PLAQUES | WT |

TABLE B-continued

| COMPOUND | STRUCTURE | VACCINIA Plaque Assay | VACCINIA PLAQUE ASSAY 2 | HERPES |
|---|---|---|---|---|
| APcK-101 | $C_{21}H_{18}N_4O_2$<br>Exact Mass: 358.143<br>Mol. Wt.: 358.3932 | CPE | | WT |
| APcK-102 | $C_{21}H_{17}FN_4O$<br>Exact Mass: 360.1386<br>Mol. Wt.: 360.3843 | SMALLER PLAQUES THAN WT | NO PLAQUES | WT |
| APcK-103 | $C_{20}H_{15}FN_4O$<br>Exact Mass: 346.123<br>Mol. Wt.: 346.3577 | NO PLAQUES | NO PLAQUES | DELAYED CPE |

TABLE B-continued
| COMPOUND | STRUCTURE | VACCINIA Plaque Assay | VACCINIA PLAQUE ASSAY 2 | HERPES |
|---|---|---|---|---|
| APcK-104 | 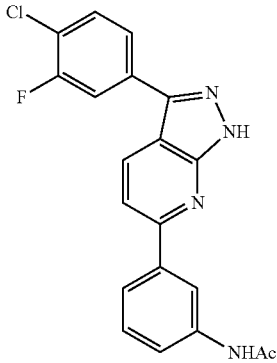<br>C₂₀H₁₄ClFN₄O<br>Exact Mass: 380.084<br>Mol. Wt.: 380.8028 | SMALLER PLAQUES THAN WT. NO COMETS | PINPOINT PLAQUES | WT |
| APcK-105 | 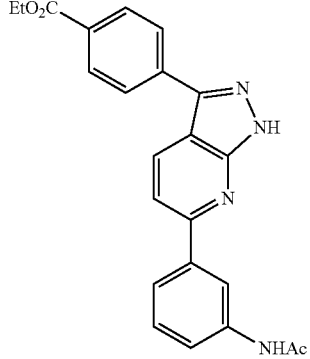<br>C₂₃H₂₀N₄O₃<br>Exact Mass: 400.1535<br>Mol. Wt.: 400.4299 | NO PLAQUES | PINPOINT PLAQUES | WT |
| APcK-106 | 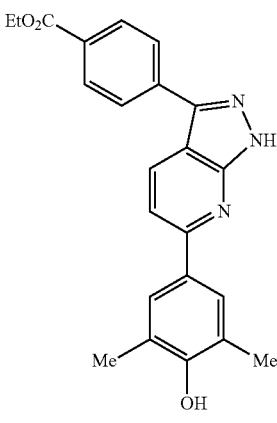<br>C₂₃H₂₁N₃O₃<br>Exact Mass: 387.1583<br>Mol. Wt.: 387.4311 | SMALLER PLAQUES THAN WT | PINPOINT PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| APcK-107 | 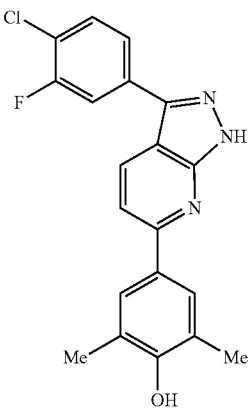<br>$C_{20}H_{15}ClFN_3O$<br>Exact Mass: 367.0888<br>Mol. Wt.: 367.804 | SMALLER PLAQUES THAN WT | SMALLER PLAQUES THAN WT | WT |
| APcK-108 | 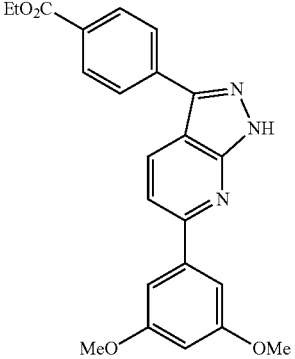<br>$C_{23}H_{21}N_3O_4$<br>Exact Mass: 403.1532<br>Mol. Wt.: 403.4305 | PINPOINT PLAQUES | SMALL PLAQUES | WT |
| APcK-109 | 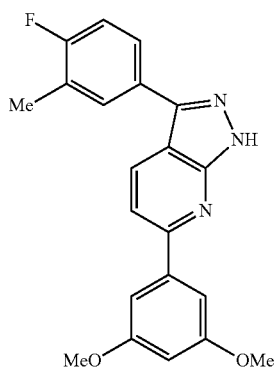<br>$C_{21}H_{18}FN_3O_2$<br>Exact Mass: 363.1383<br>Mol. Wt.: 363.3849 | SLIGHTLY SMALLER PLAQUES | SMALL PLAQUES, LARGE TAILS | WT |

TABLE B-continued
| COMPOUND | STRUCTURE | VACCINIA Plaque Assay | VACCINIA PLAQUE ASSAY 2 | HERPES |
|---|---|---|---|---|
| APcK-110 | 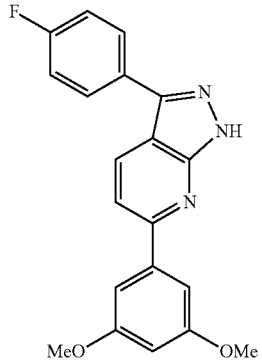<br>$C_{20}H_{16}FN_3O_2$<br>Exact Mass: 349.1227<br>Mol. Wt.: 349.3583 | SMALL PLAQUES, SEE LOTS OF SATELLITE PLAQUES | SMALL PLAQUES | WT |
| APcK-111 | 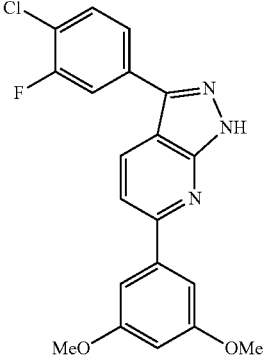<br>$C_{20}H_{15}ClFN_3O_2$<br>Exact Mass: 383.0837<br>Mol. Wt.: 383.8034 | PINPOINT PLAQUES | PINPOINT PLAQUES | WT |
| APcK-115 | 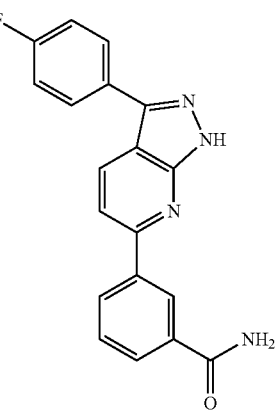<br>$C_{19}H_{13}FN_4O$<br>Exact Mass: 332.1073<br>Mol. Wt.: 332.3311 | WT | SMALL PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| APcK-19 | 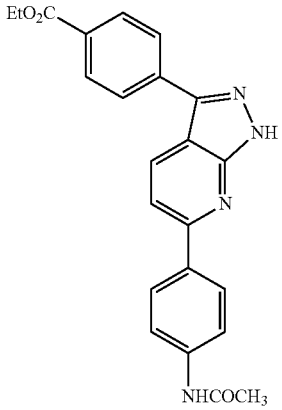<br>C₂₃H₂₀N₄O₃<br>Exact Mass: 400.1535<br>Mol. Wt.: 400.4299 | WT | SMALL PLAQUES | WT |
| APcK-20 | 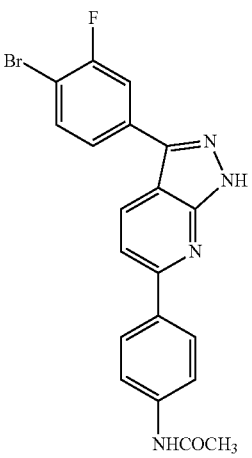<br>C₂₀H₁₄BrFN₄O<br>Exact Mass: 424.0335<br>Mol. Wt.: 425.2538 | WT | NO PLAQUES | WT |
| APcK-21 | 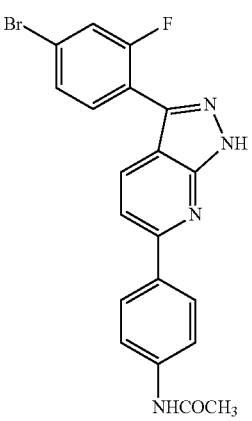<br>C₂₀H₁₄BrFN₄O<br>Exact Mass: 424.0335<br>Mol. Wt.: 425.2538 | WT | | DELAYED CPE |

| COM-POUND | STRUCTURE | VACCINIA Plaque Assay | VACCINIA PLAQUE ASSAY 2 | HERPES |
|---|---|---|---|---|
| APcK-25 | 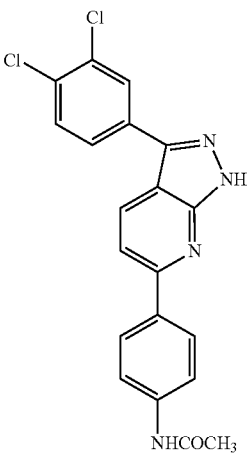<br>$C_{20}H_{14}Cl_2N_4O$<br>Exact Mass: 396.0545<br>Mol. Wt.: 397.2574 | WT | | DELAYED CPE |
| APcK-26 | 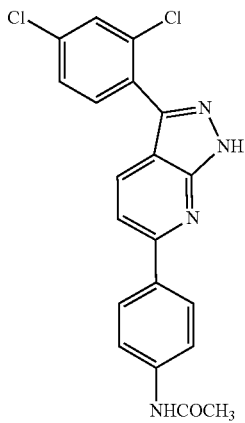<br>$C_{20}H_{14}Cl_2N_4O$<br>Exact Mass: 396.0545<br>Mol. Wt.: 397.2574 | PINPOINT PLAQUES | SMALL PLAQUES | WT |
| APcK-27 | 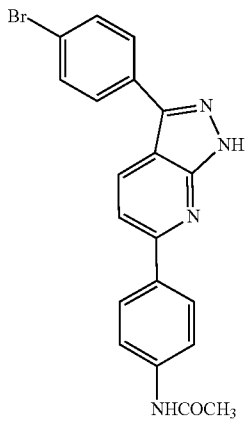<br>$C_{20}H_{15}BrN_4O$<br>Exact Mass: 406.0429<br>Mol. Wt.: 407.2633 | PINPOINT PLAQUES | SMALL PLAQUES | WT |

US 8,268,809 B2
TABLE B-continued
| COMPOUND | STRUCTURE | VACCINIA Plaque Assay | VACCINIA PLAQUE ASSAY 2 | HERPES |
|---|---|---|---|---|
| APcK-28 | 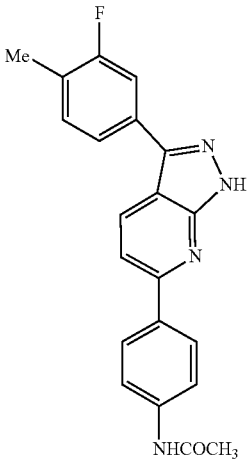<br>$C_{21}H_{17}FN_4O$<br>Exact Mass: 360.1386<br>Mol. Wt.: 360.3843 | WT | SMALL PLAQUES | WT |
| APcK-29 | 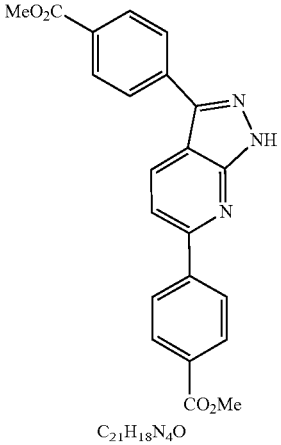<br>$C_{21}H_{18}N_4O$<br>Exact Mass: 342.1481<br>Mol. Wt.: 342.3938 | WT | SMALL PLAQUES | WT |
| APcK-31 | 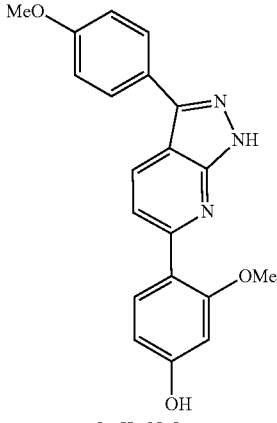<br>$C_{20}H_{17}N_3O_3$<br>Exact Mass: 347.12699<br>Mol. Wt.: 347.36728 | WT | SMALL PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| APcK-32 | 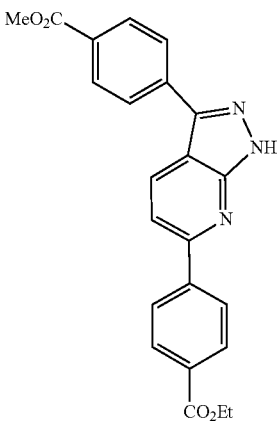<br>$C_{23}H_{19}N_3O_4$<br>Exact Mass: 401.13756<br>Mol. Wt.: 401.41466 | | LARGE COMETS | WT |
| APcK-34 | 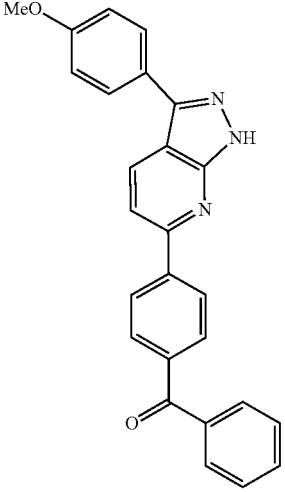<br>$C_{26}H_{19}N_3O_2$<br>Exact Mass: 405.14773<br>Mol. Wt.: 405.44796 | | SMALL PLAQUES, LARGE COMETS | WT |

TABLE B-continued
| COMPOUND | STRUCTURE | VACCINIA Plaque Assay | VACCINIA PLAQUE ASSAY 2 | HERPES |
|---|---|---|---|---|
| APcK-35 | 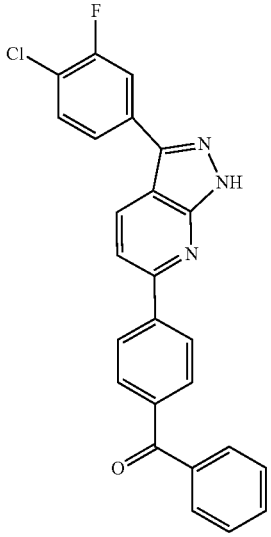<br>$C_{25}H_{15}ClFN_3O$<br>Exact Mass: 427.08877<br>Mol. Wt.: 427.8575 | SMALL PLAQUES, NO COMETS | NO PLAQUES | WT |
| APcK-36 | 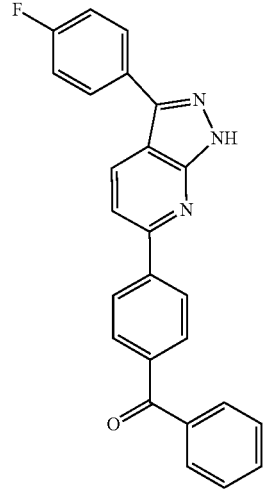<br>$C_{25}H_{16}FN_3O$<br>Exact Mass: 393.12774<br>Mol. Wt.: 393.41244 | WT | | DELAYED CPE |

TABLE B-continued

| COMPOUND | STRUCTURE | VACCINIA Plaque Assay | VACCINIA PLAQUE ASSAY 2 | HERPES |
|---|---|---|---|---|
| APcK-37 | $C_{26}H_{18}FN_3O$<br>Exact Mass: 407.14339<br>Mol. Wt.: 407.43902 | WT | SMALL PLAQUES | WT |
| APcK-38 | $C_{25}H_{15}BrFN_3O$<br>Exact Mass: 471.03825<br>Mol. Wt.: 472.3085 | WT | NO PLAQUES | WT |

TABLE B-continued
| COM- POUND | STRUCTURE | VACCINIA Plaque Assay | VACCINIA PLAQUE ASSAY 2 | HERPES |
|---|---|---|---|---|
| APcK-39 | 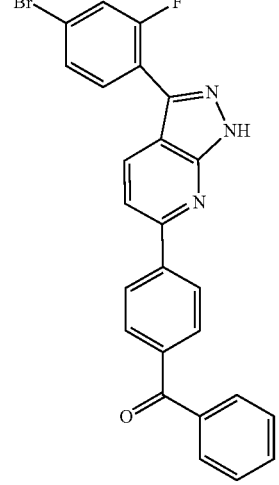<br>$C_{25}H_{15}BrFN_3O$<br>Exact Mass: 471.03825<br>Mol. Wt.: 472.3085 | WT | NO PLAQUES | WT |
| APcK-40 | 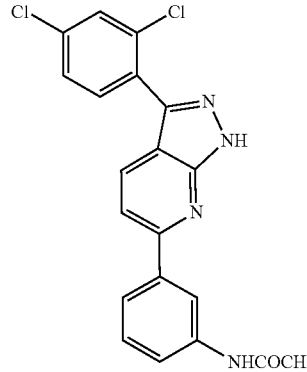<br>$C_{20}H_{14}Cl_2N_4O$<br>Exact Mass: 396.05447<br>Mol. Wt.: 397.25736 | SLIGHTLY SMALLER PLAQUES | PINPOINT PLAQUES | WT |
| APcK-41 | 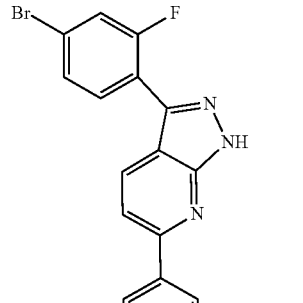<br>$C_{20}H_{14}BrFN_4O$<br>Exact Mass: 424.0335<br>Mol. Wt.: 425.25376 | WT | NO PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| APcK-42 | 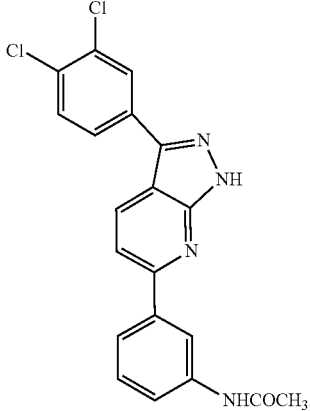<br>$C_{20}H_{14}Cl_2N_4O$<br>Exact Mass: 396.05447<br>Mol. Wt.: 397.25736 | WT | | DELAYED CPE |
| APcK-43 | 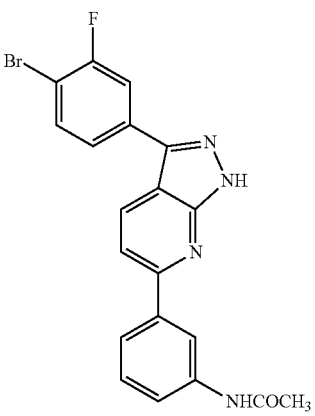<br>$C_{20}H_{14}BrFN_4O$<br>Exact Mass: 424.0335<br>Mol. Wt.: 425.25376 | NO PLAQUES | NO PLAQUES | DELAYED CPE |
| APcK-44 | 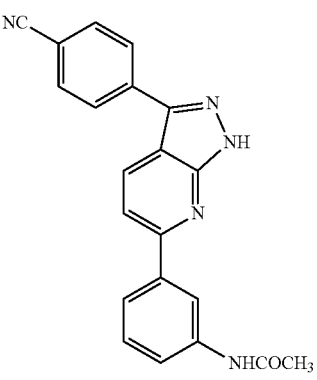<br>$C_{21}H_{15}N_5O$<br>Exact Mass: 353.12766<br>Mol. Wt.: 353.3767 | SMALL PLAQUES WITH COMETS | PINPOINT PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| APcK-48 | 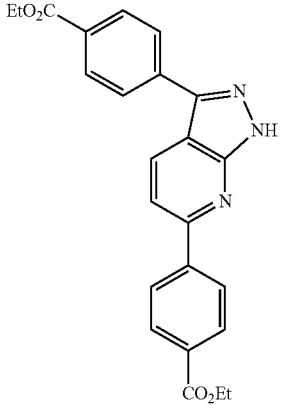<br>$C_{24}H_{21}N_3O_4$<br>Exact Mass: 415.15321<br>Mol. Wt.: 415.44124 | PINPOINT PLAQUES | SMALL PLAQUES | WT |
| APcK-49 | 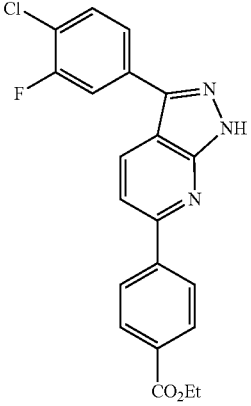<br>$C_{21}H_{15}ClFN_3O_2$<br>Exact Mass: 395.08368<br>Mol. Wt.: 395.8141 | WT | SMALL PLAQUES | WT |
| APcK-50 | 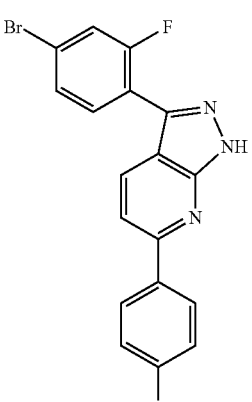<br>$C_{21}H_{15}BrFN_3O_2$<br>Exact Mass: 439.03317<br>Mol. Wt.: 440.2651 | WT | | DELAYED CPE |

TABLE B-continued

| COMPOUND | STRUCTURE | VACCINIA Plaque Assay | VACCINIA PLAQUE ASSAY 2 | HERPES |
|---|---|---|---|---|
| APcK-51 | 3-fluoro-4-methylphenyl substituted pyrazolopyridine with 4-(CO₂Et)phenyl group<br>$C_{22}H_{18}FN_3O_2$<br>Exact Mass: 375.13831<br>Mol. Wt.: 375.39562 | WT | | DELAYED CPE |
| APcK-53 | 4-fluorophenyl substituted pyrazolopyridine with 4-(CO₂Et)phenyl group<br>$C_{21}H_{16}FN_3O_2$<br>Exact Mass: 361.12265<br>Mol. Wt.: 361.36904 | WT | | DELAYED CPE |
| APcK-55 | 4-cyanophenyl substituted pyrazolopyridine with 4-(CO₂Et)phenyl group<br>$C_{22}H_{16}N_4O_2$<br>Exact Mass: 368.12733<br>Mol. Wt.: 368.38804 | WT | NO PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| APcK-58 | 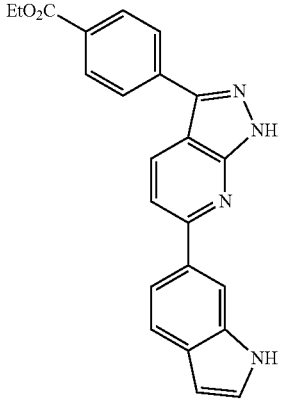<br>$C_{23}H_{18}N_4O_2$<br>Exact Mass: 382.14298<br>Mol. Wt.: 382.41462 | WT | NO PLAQUES | WT |
| butyrolactones-1 | 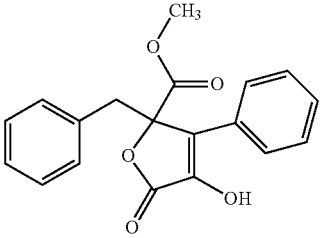<br>$C_{19}H_{16}O_5$<br>Exact Mass: 324.0998<br>Mol. Wt.: 324.3273 | SMALL PLAQUES WITH LARGE TAILS OR CPE | | WT |
| dm-I-180 | 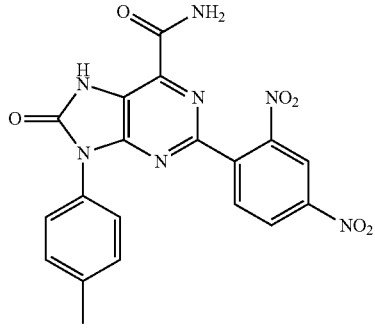<br>$C_{19}H_{13}N_7O_6$<br>Exact Mass: 435.0927<br>Mol. Wt.: 435.3498 | LARGE TAILS | | WT |

TABLE B-continued

| COMPOUND | STRUCTURE | VACCINIA Plaque Assay | VACCINIA PLAQUE ASSAY 2 | HERPES |
|---|---|---|---|---|
| dm-I-183 | C$_{23}$H$_{17}$N$_5$O$_2$S<br>Exact Mass: 427.1103<br>Mol. Wt.: 427.4784 | CPE | | WT |
| dm-I-184 | C$_{21}$H$_{15}$N$_5$O$_2$S$_2$<br>Exact Mass: 433.0667<br>Mol. Wt.: 433.5061 | WT | SLIGHTLY SMALLER PLAQUES | WT |
| dm-I-187 | C$_{19}$H$_{12}$ClF$_2$N$_5$O$_2$<br>Exact Mass: 415.0648<br>Mol. Wt.: 415.7807 | SMALL PLAQUES | NO PLAQUES | WT |

TABLE B-continued
| COMPOUND | STRUCTURE | VACCINIA Plaque Assay | VACCINIA PLAQUE ASSAY 2 | HERPES |
|---|---|---|---|---|
| dm-I-193 | 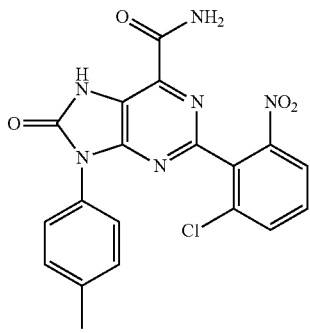<br>$C_{19}H_{13}ClN_6O_4$<br>Exact Mass: 424.0687<br>Mol. Wt.: 424.7973 | SMALL PLAQUES | NO PLAQUES | WT |
| dm-I-196 | 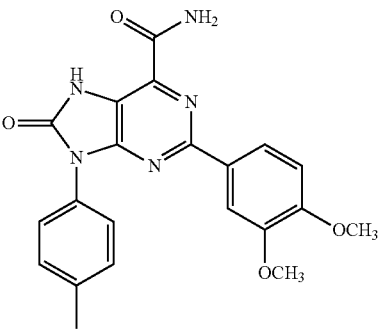<br>$C_{21}H_{19}N_5O_4$<br>Exact Mass: 405.1437<br>Mol. Wt.: 405.4067 | SMALL PLAQUES, NO TAILS | PINPOINTS | WT |
| dm-I-203 | 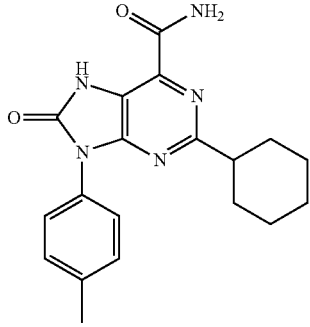<br>$C_{19}H_{21}N_5O_2$<br>Exact Mass: 351.1695<br>Mol. Wt.: 351.4023 | SMALL PLAQUES | PINPOINTS | WT |

TABLE B-continued

| COMPOUND | STRUCTURE | VACCINIA Plaque Assay | VACCINIA PLAQUE ASSAY 2 | HERPES |
|---|---|---|---|---|
| PD166326 | 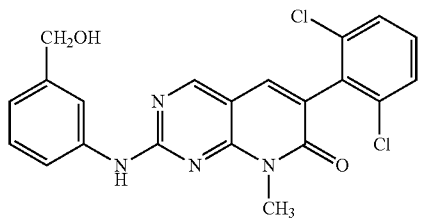 | CPE | NO PLAQUES | WT |
| PD-Br | 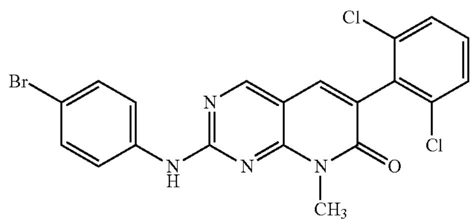 | SMALL PLAQUES, CPE | NO PLAQUES | WT |
| YYA26b | 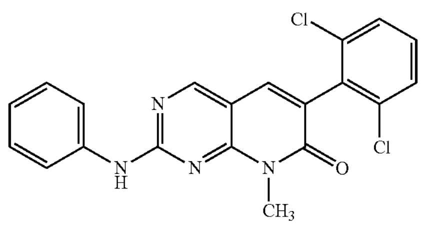 | CPE | | WT |
| YYA103 | 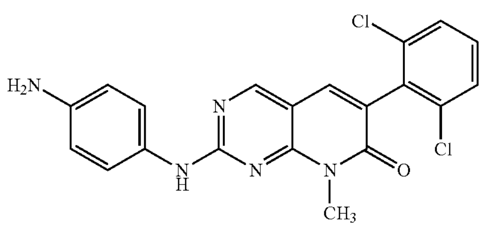 | CPE | | WT |
| YYA104 | 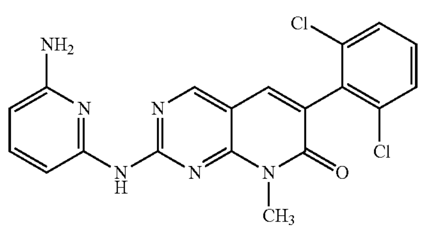 | PINPOINT PLAQUES | NO PLAQUES | WT |
| YYA105 | 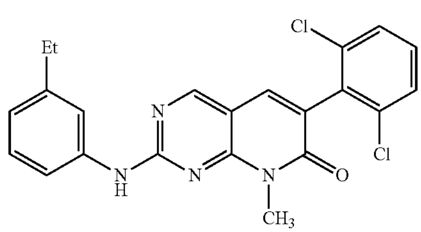 | CPE | | WT |

TABLE B-continued
| COMPOUND | STRUCTURE | VACCINIA Plaque Assay | VACCINIA PLAQUE ASSAY 2 | HERPES |
|---|---|---|---|---|
| YYA187 | 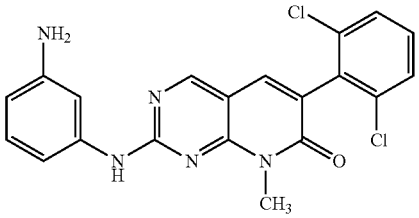 | CPE | | WT |
| YYA188 | 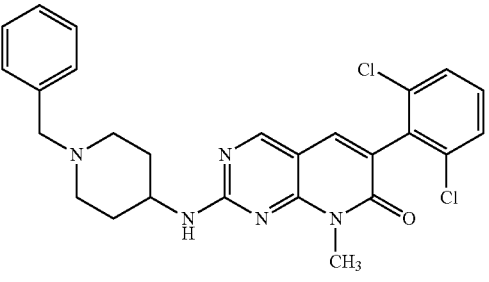 | NO PLAQUES | NO PLAQUES | WT |
| YYA190 | 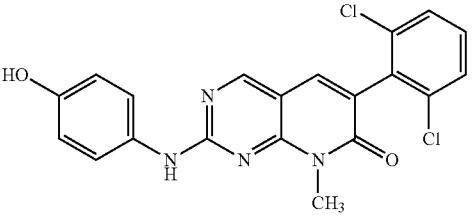 | CPE (MONOLAYER NOT INFECTED WITH VV; DRUG DESTROYED MONOLAYER, THOUGH) | | WT |
| YYA194 | 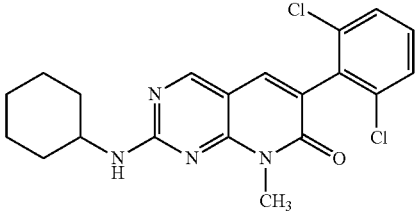 | PINPOINT PLAQUES | NO PLAQUES | WT |
| YYA195 | 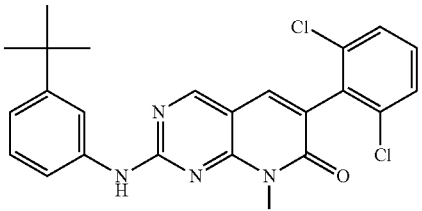 | NO PLAQUES | NO PLAQUES | WT |
| YYB19 | 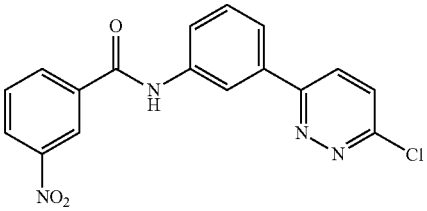 | PINPOINT PLAQUES | NO PLAQUES | WT |

TABLE B-continued

| COMPOUND | STRUCTURE | VACCINIA Plaque Assay | VACCINIA PLAQUE ASSAY 2 | HERPES |
|---|---|---|---|---|
| YYB21 | 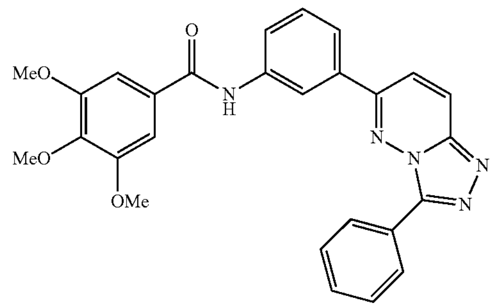 | CPE | | WT |
| YYB23 | 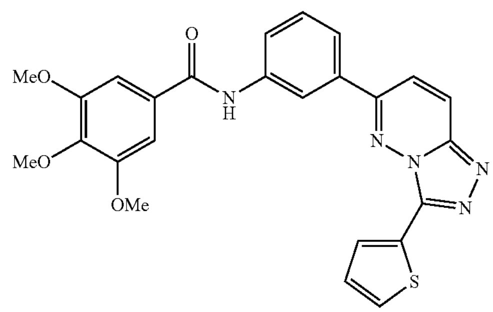 | CPE | | WT |
| YYB31 | 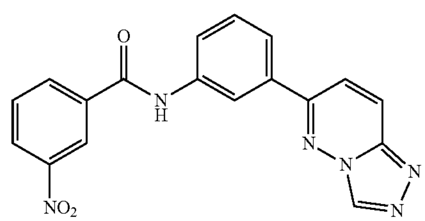 | FEW COMETS | PINPOINTS | WT |
| YYB32 | 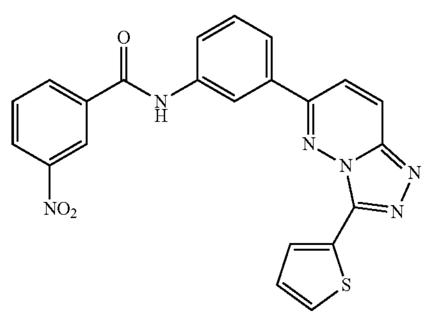 | SMALLER PLAQUES | SMALL PLAQUES | WT |
| YYB34 | 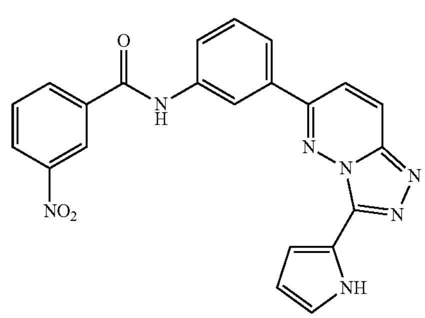 | LARGE COMETS | | WT |

| COMPOUND | STRUCTURE | VACCINIA Plaque Assay | VACCINIA PLAQUE ASSAY 2 | HERPES |
|---|---|---|---|---|
| YYB41 | 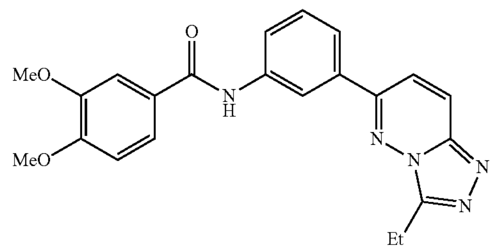 | SMALL PLAQUES | SMALL PLAQUES | WT |
| YYB44 | 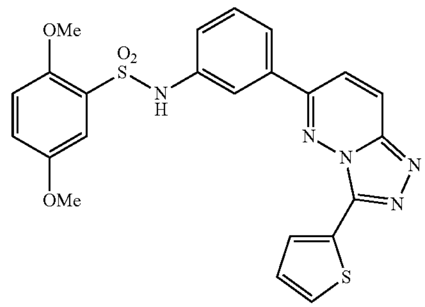 | MEDIUM PLAQUES | SMALL PLAQUES | WT |
| LG2-9 | 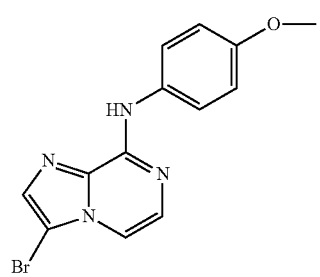 | SLIGHTLY SMALLER PLAQUES | PINPOINTS | WT |
| LG2-11 | 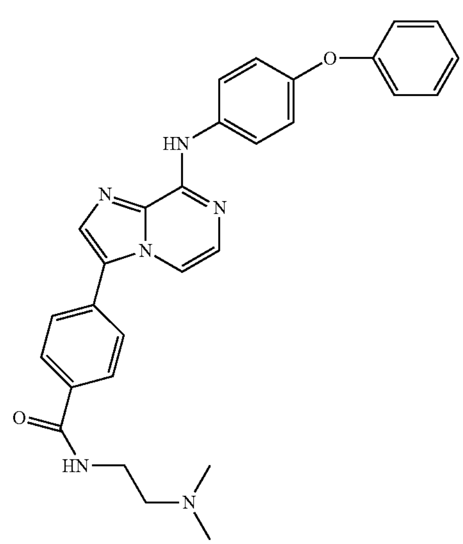 | CPE, PINPOINT PLAQUES | NO PLAQUES | WT |

TABLE B-continued

| COMPOUND | STRUCTURE | VACCINIA Plaque Assay | VACCINIA PLAQUE ASSAY 2 | HERPES |
|---|---|---|---|---|
| LG2-13 | 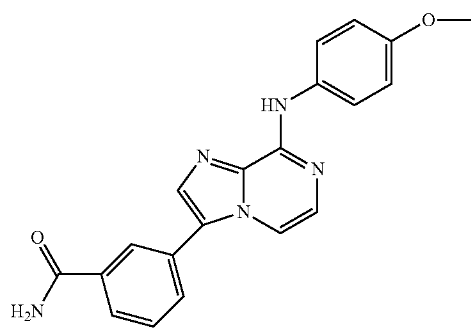 | PINPOINT PLAQUES | SLIGHTLY SMALLER PLAQUES | WT |
| LG2-60 | 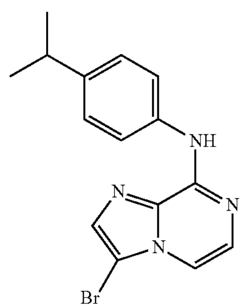 | WT | NO PLAQUES | WT |
| LG2-55 | 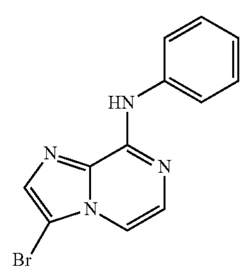 | PINPOINT PLAQUES | WT | DELAYED CPE |
| LG2-77 | 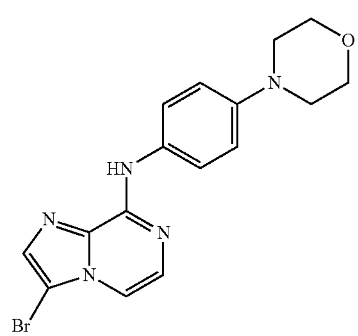 | WT | WT | DELAYED CPE |

TABLE B-continued

| COMPOUND | STRUCTURE | VACCINIA Plaque Assay | VACCINIA PLAQUE ASSAY 2 | HERPES |
|---|---|---|---|---|
| LG2-62 | 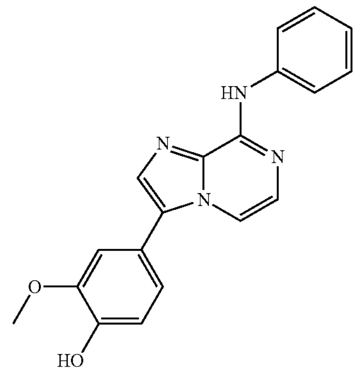 | SMALLER PLAQUES THAN WT | SMALL PLAQUES | WT |
| LG2-81 | 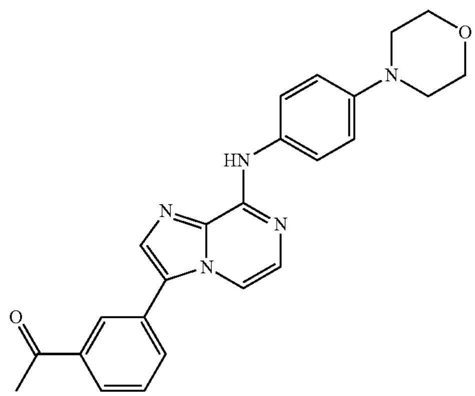 | WT | | DELAYED CPE |
| LG2-85 | 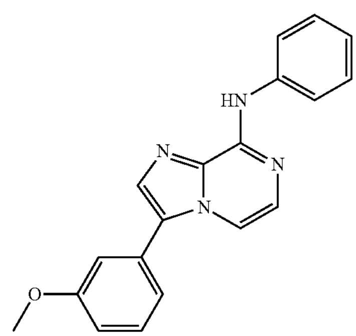 | PINPOINT PLAQUES | NO PLAQUES | WT |
| LG2-111 | 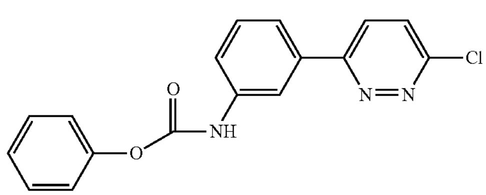 | PINPOINT PLAQUES | WT | WT |
| LG2-71 | 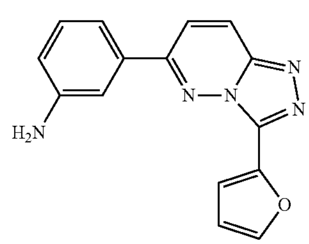 | SMALL PLAQUES, WITH COMETS | PINPOINTS | ENTRY OR EGRESS INHIBITOR |

TABLE B-continued

| COM-POUND | STRUCTURE | VACCINIA Plaque Assay | VACCINIA PLAQUE ASSAY 2 | HERPES |
|---|---|---|---|---|
| LG2-79 | 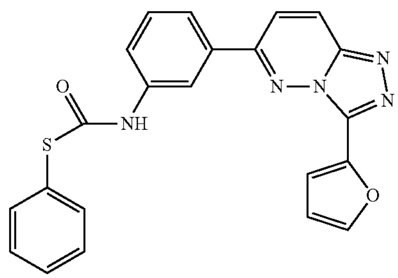 | SMALLER PLAQUES, COMETS? | SMALL PLAQUES | WT |
| LG2-95 | 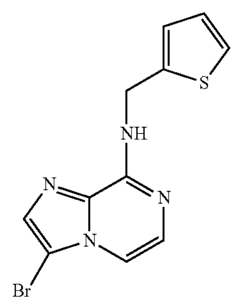 | PINPOINT PLAQUES | NO PLAQUES | WT |
| LG2-91 | 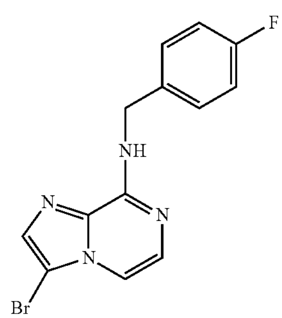 | NO PLAQUES | NO PLAQUES | WT |
| LG2-101 | 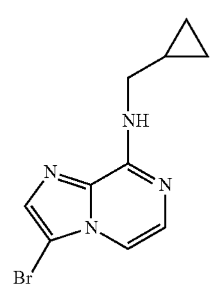 | SMALL PLAQUES, WITH TAILS | PINPOINTS | WT |

TABLE B-continued

| COMPOUND | STRUCTURE | VACCINIA Plaque Assay | VACCINIA PLAQUE ASSAY 2 | HERPES |
|---|---|---|---|---|
| LG2-102 | 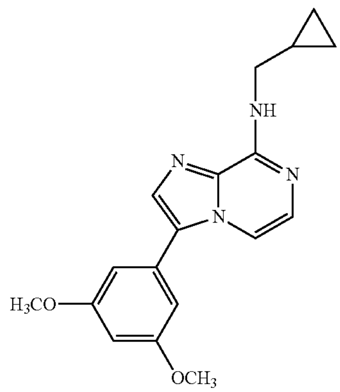 | NO PLAQUES | NO PLAQUES | WT |
| LG2-98 | 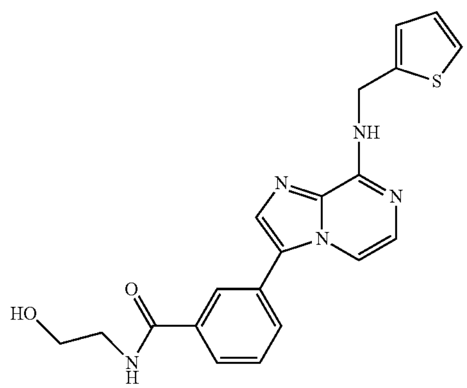 | SMALL PLAQUES, WITH TAILS | PINPOINTS | WT |
| LG2-96 | 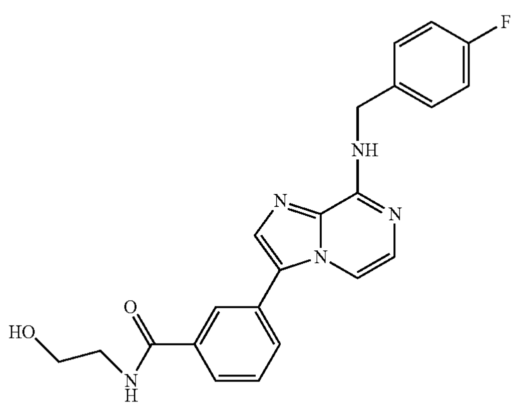 | NO PLAQUES | NO PLAQUES | WT |
| JGAP-11 | $C_{24}H_{27}IN_6O_2$<br>Exact Mass: 558.124<br>Mol. Wt.: 558.4146 | MORE PLAQUES THAN WT | | WT |

TABLE B-continued
| COMPOUND | STRUCTURE | VACCINIA Plaque Assay | VACCINIA PLAQUE ASSAY 2 | HERPES |
|---|---|---|---|---|
| JGAP-13 | 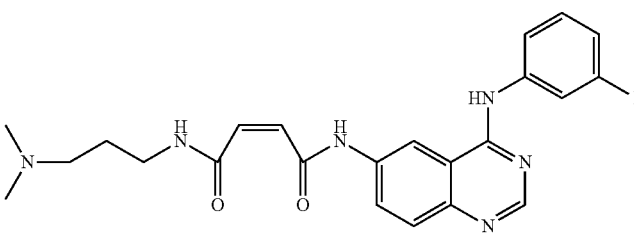<br>C₂₃H₂₅IN₆O₂<br>Exact Mass: 544.1084<br>Mol. Wt.: 544.3881 | MORE PLAQUES THAN WT | | WT |
| JGAP-5 | 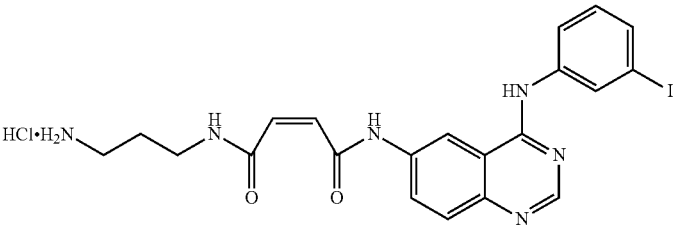<br>C₂₁H₂₂ClIN₆O₂<br>Exact Mass: 552.0537<br>Mol. Wt.: 552.7958 | MASSIVE COMETS | | WT |
| CGP-2 | 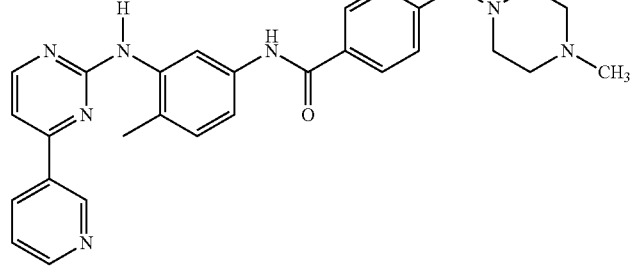<br>C₂₉H₃₁N₇O<br>Mol. Wt.: 493.6 | CPE | | ENTRY OR EGRESS INHIBITOR |
| CGP51148 WBZ-4 | 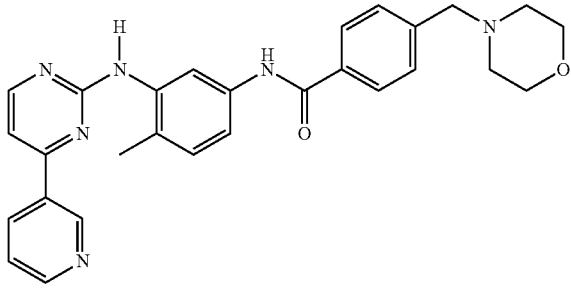<br>C₂₈H₂₈N₆O₂<br>Mol. Wt.: 480.56 | CPE | | DELAYED CPE |

TABLE B-continued

| COMPOUND | STRUCTURE | VACCINIA Plaque Assay | VACCINIA PLAQUE ASSAY 2 | HERPES |
|---|---|---|---|---|
| AMN107 | | CPE | | WT |
| JAK2F | 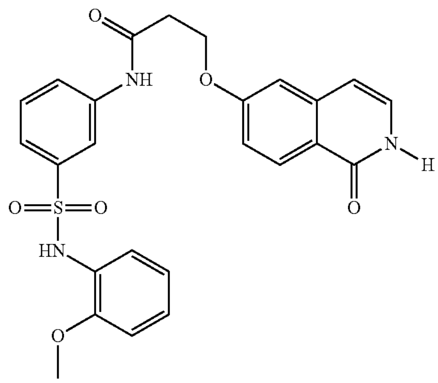 | SMALL PLAQUES | SLIGHTLY SMALLER PLAQUES | WT |

HERPES - WT IS OBLITERATED MONOLAYER
VACCINIA VIRUS - WT, PLAQUE ASSAY IS NORMAL SIZED PLAQUES AND COMET TAILS
CPE—CYTOPATHIC EFFECTS

What is claimed is:

1. A method of preventing or treating pathogenic infection comprising administering a therapeutically effective amount of compositions comprising a tyrosine kinase inhibitor as set forth below to a patient in need thereof for preventing or treating infection caused by an array of pathogens:

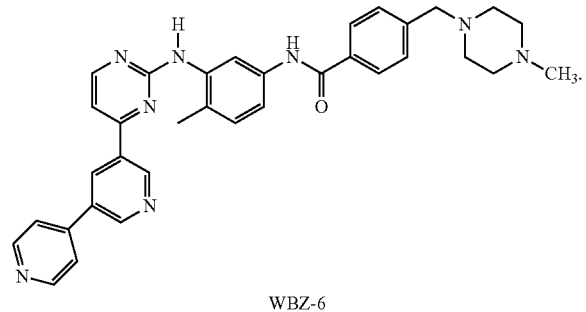

WBZ-6

2. The method of claim 1, wherein said tyrosine kinase inhibitors are Ab 1- or Src-family tyrosine kinase inhibitors.

3. The method of claim 1, wherein said pathogenic infection is caused by viral pathogens.

4. The method of claim 3, wherein said viral pathogens are selected from the group consisting of Adenoviridae, Arenaviridae, Astroviridae, Bacteriophages, Baculoviridae, Bunyaviridae, Caliciviridae, Coronaviridae, Delta virus, Filoviridae, Flaviviridae, Geminiviridae, Hepadnaviridae, Herpesviridae, Nodaviridae, Orthomyxoviridae, Papovaviridae, Paramyxoviridae, Parvoviridae, Phycodnaviridae, Picornaviridae, Poxyiridae, Reoviridae, Retroviridae, Rhabdoviridae, Tobamoviridae, and Togaviridae, Poxviruses including Vaccinia and variola viruses, polyoma viruses including JC and BK viruses, Herpes viruses including Herpes Simplex virus, Epstein Barr virus, and Gamma Herpes virus, cytomegalovirus (CMV), and human immunodeficiency viruses (HIV-1).

5. The method of claim 3, wherein said pathogenic infection is caused by poxvirus.

6. The method of claim 5, wherein said pathogenic infection is caused by vaccinia viruses.

7. The method of claim 3, wherein pathogenic infection is caused by Herpes viruses including Herpes Simplex virus, Epstein Barr virus, and Gamma Herpes virus.

8. The method of claim 1, wherein said kinase inhibitor is

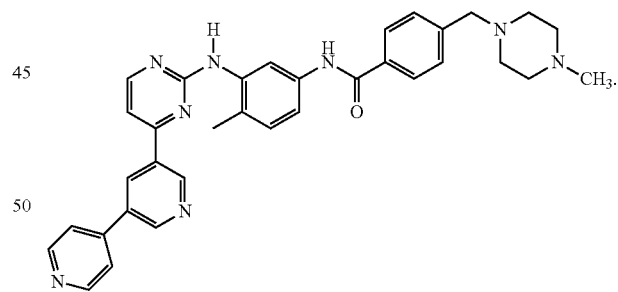

WBZ-6

9. The method of claim 1, wherein said pathogenic infection is an acute infection.

10. The method of claim 9, wherein said acute infection is treated for less than three weeks.

* * * * *